(12) United States Patent
Nassef et al.

(10) Patent No.: US 9,103,825 B2
(45) Date of Patent: Aug. 11, 2015

(54) MICROFLUIDIC ASSAY DEVICES AND METHODS

(75) Inventors: Hany Ramez Nassef, San Mateo, CA (US); Hou-Pu Chou, Sunnyvale, CA (US); Michael Lucero, South San Francisco, CA (US); Andrew May, San Francisco, CA (US); Kathy Yokobata, Sunnyvale, CA (US)

(73) Assignee: FLUIDIGM CORPORATION, South San Francisco, CA (US)

( * ) Notice: Subject to any disclaimer, the term of this patent is extended or adjusted under 35 U.S.C. 154(b) by 141 days.

(21) Appl. No.: 12/764,819

(22) Filed: Apr. 21, 2010

(65) Prior Publication Data
US 2011/0020918 A1 Jan. 27, 2011

Related U.S. Application Data

(63) Continuation of application No. 11/522,815, filed on Sep. 13, 2006, now abandoned.

(60) Provisional application No. 60/716,823, filed on Sep. 13, 2005.

(51) Int. Cl.
*B01L 3/00* (2006.01)
*G01N 33/543* (2006.01)
(Continued)

(52) U.S. Cl.
CPC .... *G01N 33/54366* (2013.01); *B01L 3/502738* (2013.01); *F16K 99/0001* (2013.01); *F16K 99/0015* (2013.01); *F16K 99/0051* (2013.01); *F16K 99/0059* (2013.01); *G01N 33/5302* (2013.01); *B01J 2219/00286* (2013.01); *B01J 2219/00317* (2013.01); *B01J 2219/00389* (2013.01); *B01J 2219/00398* (2013.01); *B01L 3/5025* (2013.01); *B01L 3/502715* (2013.01);
(Continued)

(58) Field of Classification Search
CPC ............... G01N 33/54366; G01N 33/5302; B01L 3/5025; B01L 3/502715; B01L 3/502738; B01J 2219/00286; B01J 2219/00317; B01J 2219/00389; B01J 2219/00398; F16K 99/0001; F16K 99/0015; F16K 99/0051; F16K 99/0059; F16K 2099/0074; F16K 2099/008; F16K 2099/0084
USPC ....................................................... 422/100
See application file for complete search history.

(56) References Cited

U.S. PATENT DOCUMENTS 6,540,895 B1 4/2003 Spence et al.
6,885,982 B2 4/2005 Harris et al.
(Continued)

FOREIGN PATENT DOCUMENTS

DE 10041853 2/2002
WO WO 01/07889 A2 2/2001
(Continued)

OTHER PUBLICATIONS

International Search Report for PCT/US2006/036365. Date: Mar. 13, 2008. Ten pages.*

*Primary Examiner* — Lyle Alexander
*Assistant Examiner* — Robert Eom
(74) *Attorney, Agent, or Firm* — Kilpatrick Townsend & Stockton LLP

(57) ABSTRACT

A microfluidic device adapted to perform many simultaneous binding assays including but not limited to immunological experiments, such as ELISA assays, with minimal cross-talk between primary and secondary antibodies.

15 Claims, 24 Drawing Sheets

(51) Int. Cl.
*F16K 99/00* (2006.01)
*G01N 33/53* (2006.01)

(52) U.S. Cl.
CPC .. *B01L 2300/0816* (2013.01); *B01L 2300/0874* (2013.01); *B01L 2300/123* (2013.01); *B01L 2400/0487* (2013.01); *B01L 2400/0655* (2013.01); *F16K 2099/008* (2013.01); *F16K 2099/0074* (2013.01); *F16K 2099/0084* (2013.01)

(56) References Cited

U.S. PATENT DOCUMENTS

| | | | |
|---|---|---|---|
| 6,951,632 | B2 | 10/2005 | Unger et al. |
| 7,042,649 | B2 | 5/2006 | Quake et al. |
| 7,059,348 | B2 | 6/2006 | Nat |
| 7,062,418 | B2 | 6/2006 | Lee et al. |
| 7,097,809 | B2 | 8/2006 | Dam et al. |
| 7,160,687 | B1 * | 1/2007 | Kapur et al. .................. 435/7.2 |
| 7,161,736 | B2 | 1/2007 | Legrand et al. |
| 7,192,629 | B2 | 3/2007 | Lammertink et al. |
| 7,217,367 | B2 | 5/2007 | Huang et al. |
| 7,232,109 | B2 | 6/2007 | Driggs et al. |
| 7,248,413 | B2 | 7/2007 | Quake et al. |
| 7,262,923 | B2 | 8/2007 | Quake et al. |
| 7,279,146 | B2 | 10/2007 | Nassef |
| 7,291,512 | B2 | 11/2007 | Unger |
| 7,294,503 | B2 | 11/2007 | Quake et al. |
| 7,361,314 | B1 * | 4/2008 | Stahler et al. ................. 422/502 |
| 7,368,163 | B2 | 5/2008 | Huang et al. |
| 7,442,556 | B2 | 10/2008 | Manger et al. |
| 7,476,363 | B2 | 1/2009 | Unger et al. |
| 7,526,741 | B2 | 4/2009 | Lee et al. |
| 7,604,965 | B2 | 10/2009 | McBride et al. |
| 7,666,361 | B2 | 2/2010 | McBride et al. |
| 7,678,547 | B2 | 3/2010 | Eyal et al. |
| 7,691,333 | B2 | 4/2010 | McBride et al. |
| 7,749,737 | B2 | 7/2010 | McBride et al. |
| 7,792,345 | B2 | 9/2010 | Taylor et al. |
| 7,815,868 | B1 | 10/2010 | Jones et al. |
| 7,820,427 | B2 | 10/2010 | Unger et al. |
| 7,833,708 | B2 | 11/2010 | Enzelberger et al. |
| 7,837,946 | B2 | 11/2010 | McBride et al. |
| 2004/0112442 | A1 * | 6/2004 | Maerkl et al. ................. 137/597 |
| 2004/0180377 | A1 | 9/2004 | Manger et al. |
| 2005/0047967 | A1 | 3/2005 | Chuang et al. |
| 2005/0053952 | A1 | 3/2005 | Hong et al. |
| 2005/0129581 | A1 | 6/2005 | McBride et al. |
| 2006/0172408 | A1 | 8/2006 | Quake et al. |
| 2006/0233674 | A1 | 10/2006 | Nelson |
| 2006/0281183 | A1 | 12/2006 | Sun et al. |
| 2007/0134807 | A1 | 6/2007 | Bao et al. |
| 2007/0224617 | A1 | 9/2007 | Quake et al. |
| 2007/0248971 | A1 | 10/2007 | Maerkl et al. |
| 2008/0050283 | A1 | 2/2008 | Chou et al. |
| 2008/0075380 | A1 | 3/2008 | Dube et al. |
| 2008/0108063 | A1 | 5/2008 | Lucero et al. |
| 2008/0129736 | A1 | 6/2008 | Sun et al. |
| 2008/0176211 | A1 | 7/2008 | Spence et al. |
| 2008/0223721 | A1 | 9/2008 | Cohen et al. |
| 2008/0230387 | A1 | 9/2008 | McBride et al. |
| 2008/0264863 | A1 | 10/2008 | Quake et al. |
| 2008/0274493 | A1 | 11/2008 | Quake et al. |
| 2008/0281090 | A1 | 11/2008 | Lee et al. |
| 2008/0292504 | A1 | 11/2008 | Goodsaid et al. |
| 2009/0018195 | A1 | 1/2009 | Balagadde |
| 2009/0069194 | A1 | 3/2009 | Ramakrishnan |
| 2009/0142236 | A1 | 6/2009 | Unger et al. |
| 2009/0147918 | A1 | 6/2009 | Fowler et al. |
| 2009/0168066 | A1 | 7/2009 | Hansen et al. |
| 2009/0239308 | A1 | 9/2009 | Dube et al. |
| 2009/0291435 | A1 | 11/2009 | Unger et al. |
| 2010/0104477 | A1 | 4/2010 | Liu et al. |
| 2010/0120018 | A1 | 5/2010 | Quake et al. |
| 2010/0120077 | A1 | 5/2010 | Daridon |
| 2010/0154890 | A1 | 6/2010 | Maerkl et al. |
| 2010/0166608 | A1 | 7/2010 | Quan et al. |
| 2010/0171954 | A1 | 7/2010 | Quake et al. |
| 2010/0183481 | A1 | 7/2010 | Facer et al. |
| 2010/0184202 | A1 | 7/2010 | McBride et al. |
| 2010/0187105 | A1 | 7/2010 | Unger et al. |
| 2010/0196892 | A1 | 8/2010 | Quake et al. |
| 2010/0197522 | A1 | 8/2010 | Liu et al. |
| 2010/0200782 | A1 | 8/2010 | Unger et al. |
| 2010/0230613 | A1 | 9/2010 | Pieprzyk et al. |
| 2010/0263732 | A1 | 10/2010 | Hansen et al. |
| 2010/0263757 | A1 | 10/2010 | Fernandes et al. |
| 2010/0311060 | A1 | 12/2010 | Facer et al. |
| 2010/0320364 | A1 | 12/2010 | Unger et al. |

FOREIGN PATENT DOCUMENTS

| | | | |
|---|---|---|---|
| WO | WO 01/08799 A1 | 2/2001 | |
| WO | WO 0108799 A1 * | 2/2001 | ............ B01L 3/00 |
| WO | WO 01/67369 A2 | 9/2001 | |
| WO | WO 2007/033385 A2 | 3/2007 | |
| WO | WO 2007033385 A2 * | 3/2007 | ............ B01L 3/00 |
| WO | WO 2007/044091 A2 | 4/2007 | |
| WO | WO 2008/043046 A2 | 4/2008 | |
| WO | WO 2009/100449 A1 | 8/2009 | |
| WO | WO 2010/011852 A1 | 1/2010 | |
| WO | WO 2010/017210 A1 | 2/2010 | |
| WO | WO 2010/077618 A1 | 7/2010 | |

* cited by examiner

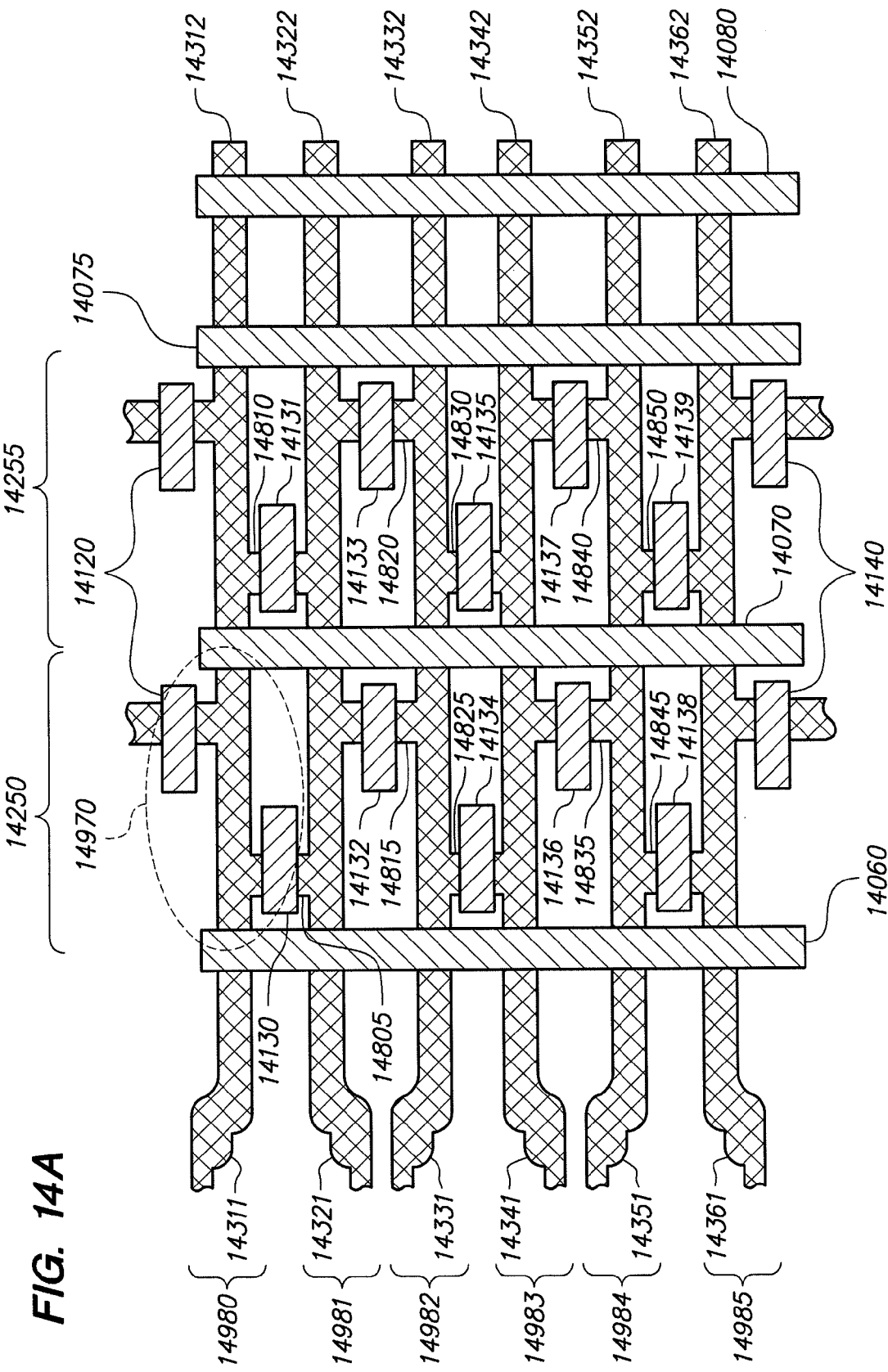

MICROFLUIDIC ASSAY DEVICES AND METHODS

This application is a continuation of U.S. patent application Ser. No. 11/522,815 filed Sep. 13, 2006, titled "Microfluidic Assay Devices and Methods" (now abandoned), which claims priority to U.S. Provisional Patent Application Ser. No. 60/716,823 filed on Sep. 13, 2005. The entire disclosure of both U.S. Patent Applications are hereby incorporated by reference, for all purposes, as if fully set forth herein.

BACKGROUND

A number of patents and published applications disclose microfluidic devices that may be used to perform various chemical and biochemical analyses and syntheses. These disclosures include the following publications, all of which are incorporated by reference in their entirety for all purposes: U.S. Pat. No. 6,767,706 ("Integrated Active Flux Microfluidic Devices and Methods"), US20020127736A1 ("Microfluidic Devices And Methods Of Use"), US20020109114A1 ("Electrostatic Valves For Microfluidic Devices"), US20050145496A1 ("Thermal Reaction Device And Method For Using The Same"), and U.S. Pat. No. 6,729,352 ("Microfluidic Synthesis Devices And Methods").

Additionally, the following applications and patents disclose relevant information pertinent to the present invention: U.S. non-provisional patent application Ser. No. 10/819,088, filed on Apr. 5, 2004 which claims priority to U.S. provisional patent application Ser. No. 60/460,634, filed on Apr. 3, 2003, both of which are incorporated by reference in their entirety for all purposes; U.S. Non-Provisional application Ser. No. 10/306,798, filed on Nov. 27, 2002, which claims priority under 35 U.S.C. §119(e) to U.S. Provisional Application No. 60/391,529, filed Jun. 24, 2002, and of U.S. Provisional Application No. 60/335,292, filed Nov. 30, 2001, each of which is incorporated by reference in their entirety for all purposes.

The general benefits of using microfluidic systems include a substantial reduction in time, cost and the space requirements for the devices utilized to conduct the analysis or synthesis.

Immunological methods are well known, and are performed routinely for diagnostic and research purposes. The problems with immunological methods are also well known, and are generally focused around increasing sensitivity while maintaining a high degree of specificity. Increasing sensitivity may be done by increasing the concentration of binding or target species, but increased concentration of reagents leads to an increased amount of non-specific binding of cross-reactive antibodies, leading to false positives. So there is a constant tension between the requirements for specificity and sensitivity.

Enzyme-linked Immunosorbent Assays (ELISAs) combine the specificity of antibodies with the sensitivity of simple enzyme assays, by using antibodies or antigens coupled to an easily-assayed enzyme. ELISAs can provide a useful measurement of antigen or antibody concentration. There are two main variations on this method: The ELISA can be used to detect the presence of antigens that are recognized by an antibody or it can be used to test for antibodies that recognize an antigen. An ELISA is generally a five-step procedure: 1) coat the microtiter plate wells with antigen; 2) block all unbound sites to prevent false positive results; 3) add antibody to the wells; 4) add anti-mouse IgG conjugated to an enzyme; 5) reaction of a substrate with the enzyme to produce a colored product, thus indicating a positive reaction. There are many different types of ELISAs.

One of the most useful of the immunoassays is the two antibody "sandwich" ELISA. This assay is used to determine the antigen concentration in unknown samples. If a purified antigen standard is available, the assay can determine the absolute amount of antigen in an unknown sample. The sandwich ELISA requires two antibodies that bind to epitopes that do not overlap on the antigen. This can be accomplished with either two monoclonal antibodies that recognize discrete sites or one batch of affinity-purified polyclonal antibodies. One antibody (the "capture" antibody) is purified and bound to a solid phase typically attached to the bottom of a plate well. Antigen is then added and allowed to complex with the bound antibody. Unbound products are then removed with a wash, and a labeled second antibody (the "detection" antibody) is allowed to bind to the antigen, thus completing the "sandwich". The assay is then quantitated by measuring the amount of labeled second antibody bound to the matrix, through the use of a colorimetric substrate. Major advantages of this technique are that the antigen does not need to be purified prior to use, and that these assays are very specific. However, one disadvantage is that not all antibodies can be used. Monoclonal antibody combinations must be qualified as "matched pairs", meaning that they can recognize separate epitopes on the antigen so they do not hinder each other's binding.

Unlike Western blots, which use precipitating substrates, ELISA procedures utilize substrates that produce soluble products. Ideally the enzyme substrates should be stable, safe and inexpensive. Popular enzymes are those that convert a colorless substrate to a colored product, e.g., p-nitrophenylphosphate (pNPP), which is converted to the yellow p-nitrophenol by alkaline phosphatase. Substrates used with peroxidase include 2,2'-azo-bis(3-ethylbenzothiazoline-6-sulfonic acid) (ABTS), o-phenylenediamine (OPD) and 3,3'5,5'-tetramethylbenzidine base (TMB), which yield green, orange and blue colors, respectively.

The sensitivity of the sandwich ELISA is dependent on four factors: (1) The number of molecules of the first antibody that are bound to the solid phase. (2) The avidity of the first antibody for the antigen. (3) The avidity of the second antibody for the antigen. (4) The specific activity of the second antibody.

When two "matched pair" antibodies are not available for a target, another option is the competitive ELISA. Another advantage to the competitive ELISA is that non-purified primary antibodies may be used. In order to utilize a competitive ELISA, one reagent must be conjugated to a detection enzyme, such as horseradish peroxidase. The enzyme may be linked to either the immunogen or the primary antibody. A labeled immunogen is commonly used as the competitor.

In use, an unlabeled purified primary antibody is coated onto the wells of a 96 well microtiter plate. This primary antibody is then incubated with unlabeled standards and unknowns. After this reaction is allowed to go to equilibrium, conjugated immunogen is added. This conjugate will bind to the primary antibody wherever its binding sites are not already occupied by unlabeled immunogen. Thus, the more immunogen in the sample or standard, the lower the amount of conjugated immunogen bound. The plate is then developed with substrate and color change is measured.

Conventional ELISAs generally provide a plate with a number of reaction wells onto which a number of primary antibodies have been pre-spotted. The wells are then flooded with the antigen to be detected which binds via a first epitope to the primary antibody. The secondary labeled antibody is then flooded onto the plate and binds specifically to a second epitope of the antigen. A signal is then produced and detected by use of a colorimetric substrate.

A major problem with current antibody systems is caused by cross-talk between the antibodies. This problem is inherent in a system that requires exposure of the primary antibody to a cocktail of polyclonal secondary antibodies, some of which may bind non-specifically not to the bound antigen, but to the primary antibody, creating false positives.

SUMMARY

The present invention provides microfluidic devices usable to conduct immunological experiments and assays. In particular, the invention provides microfluidic devices that can be used to perform qualitative and quantitative immunological assays including ELISA reactions.

In particular the present invention provides microfluidic devices with the ability to conduct many simultaneous experiments with no cross-talk between the antibodies. Cross-talk is eliminated by physically isolating each primary and secondary antibody in the panel. Each primary antibody is delivered through a separate primary delivery channel, into a reaction chamber. These reaction chambers are then flowed through with a sample containing the target antigen, and then flowed through with a second antibody which is also separate and delivered via a second inlet.

The isolation and separate delivery of the secondary antibody to the reception chambers is fundamental to eliminating potential cross-talk between all antibodies in the panel. Current systems combine the secondary antibodies into a single cocktail which is used to flood the assay cambers. This cocktail may contain antibodies that will cross-talk with other antibodies (e.g. secondary antibodies may bind non-specifically with primary antibodies). This cross-talk problem requires users to employ the very laborious process of screening individual pairs of antibodies against one another to determine cross-talk and therefore identify the "poor quality" antibodies that produce the false positives.

The devices of the invention, for example, may be used as an analytical tool to determine whether a particular target protein or peptide of interest is present or absent in a sample. Such devices may also be used to detect the presence or amount of antibodies in a sample.

The devices may be utilized to test for the presence or quantity of particular pathogen, or for the presence or quantity of proteins, peptides or antibodies associated with such pathogens (e.g., viruses, bacteria or fungi). Such applications would provide a quick, efficient, accurate, sensitive and inexpensive screening method useful in public health and counter-bio-terrorism applications.

The invention may also be used to detect protein and non-protein agents, poisons and toxins (such as abrin, ricin and modeccin etc), and nerve agents, e.g., the "G" agents (such as tabun, soman, sarin, and cyclosarin) and the "V" agents, such as VX.

Such devices could also be used for identification purposes (e.g., paternity and forensic applications). Such devices could also be utilized to detect or characterize specific proteins or antibodies correlated with particular diseases or genetic disorders such as diabetes, cancer etc.

Alternatively, the devices can be used to perform combinatorial synthetic chemistry or immunology, preparing a large number of combinations simultaneously.

A variety of devices and methods for conducting microfluidic analyses are provided herein, including microfluidic chips that can be used to perform "multiplexed" ELISA reactions without cross-reactivity problems. The present devices and methods employ very small volumes and provide superior sensitivity in the picoliter per milliliter range. Another advantage of the current invention is that the methods may be automated to improve processing speed and reduce cost. The devices differ from conventional microfluidic devices in that they include elastomeric components; in some instances, much or the entire device is composed of elastomeric materials.

Some of the devices include blind flow channels which include a region that functions as a reaction chamber (also sometimes called a reaction site). Blind flow (also called "blind fill") refers to the filling of a dead-end tube or lumen with a liquid wherein a head of gas is pushed in front of the liquid bolus, and wherein that head of gas is vented or otherwise released from the lumen, allowing the dead-end lumen to fill fully with the liquid. In the present invention, PDMS (Poly Dimethyl Siloxane, a type of silicone) is often used. PDMS is sufficiently gas permeable that liquid pressurized at a few psi drives the gas out of the channels, leaving them completely filled with liquid. See Hansen et al, *PNAS* 99, 16531-16536 (2002).

Certain such devices include a flow channel formed within an elastomeric material, and a plurality of blind flow channels in fluid communication with the flow channel, with a region of each blind flow channel defining a reaction chamber. The devices can also include one or more control channels overlaying and intersecting each of the blind flow channels, wherein an elastomeric membrane separates the one or more control channels from the blind flow channels at each intersection. The elastomeric membrane in such devices is disposed to be deflected into or withdrawn from the blind flow channel in response to an actuation force. The devices can optionally further include a plurality of guard channels formed within the elastomeric material and overlaying the flow channel and/or one or more of the reaction chambers. The guard channels are designed to have fluid flow therethrough to reduce evaporation from the flow channels and reaction chambers of the device. Additionally, the devices can optionally include one or more reagents deposited within each of the reaction chambers.

In certain devices, the flow channel is one of a plurality of flow channels, each of the flow channels in fluid communication with multiple blind flow channels which branch therefrom. Of devices of this design, in some instances the plurality of flow channels are interconnected with one another such that fluid can be introduced into each of the reaction chambers via a single inlet. In other devices, however, the plurality of flow channels are isolated from each other such that fluid introduced into one flow channel cannot flow to another flow channel, and each flow channel comprises an inlet at one or both ends into which fluid can be introduced.

Other devices include an array of reaction chambers having a density of at least 50 sites/cm$^2$, with the reaction chambers typically formed within an elastomeric material. Other devices have even higher densities such as at least 250, 500 or 1000 sites/cm$^2$, for example.

Still other devices include a reaction chamber formed within an elastomeric substrate, at which a reagent for conducting a reaction is non-covalently immobilized. The reagent can be one or more reagents for conducting essentially any type of reaction. Thus, in some devices the reagent comprises one or more antibodies, proteins or peptides.

A variety of matrix or array-based devices are also provided. Certain of these devices include: (i) a first plurality of flow channels formed in an elastomeric substrate, (ii) a second plurality of flow channels formed in the elastomeric substrate that intersect the first plurality of flow channels to define an array of reaction chambers, (iii) a plurality of isolation valves disposed within the first and second plurality of flow channels that can be actuated to isolate solution within each of the reaction chambers from solution at other reaction chambers, and (iv) a plurality of guard channels overlaying one or more of the flow channels and/or one or more of the reaction chambers to prevent evaporation of solution therefrom.

The foregoing devices can be utilized to conduct a number of different types of reaction, including various detection reactions, ELISA reactions and combinatorial chemical and immunochemical reactions.

Methods conducted with certain blind channel type devices involve providing a microfluidic device that comprises a flow channel formed within an elastomeric material; and a plurality of blind flow channels in fluid communication with the flow channel, with an end region of each blind flow channel defining a reaction chamber. At least one reagent is introduced into each of the reaction chambers, and then a reaction is detected at one or more of the reaction chambers. The method can optionally include detection of a reaction or bound substrate using fluorescent or colour Other methods involve providing a microfluidic device comprising one or more reaction chambers, each reaction chamber comprising a first reagent for conducting an analysis that is non-covalently deposited on an elastomeric substrate. A second reagent is then introduced into the one or more reaction chambers, whereby the first and second reagents mix to form a reaction mixture. A reaction between the first and second reagents at one or more of the reaction chambers is subsequently detected.

Still other methods involve providing a microfluidic device comprising an array of reaction chambers formed within a substrate and having a density of at least 50 sites/cm$^2$. At least one reagent is introduced into each of the reaction chambers. A reaction at one or more of the reaction chambers is then detected.

Yet other methods involve providing a microfluidic device comprising at least one reaction chamber which is formed within an elastomeric substrate and a plurality of guard channels also formed within the elastomeric substrate. At least one reagent is introduced into each of the reaction chambers and then heated within the reaction chambers. A fluid is flowed through the guard channels before or during heating to reduce evaporation from the at least one reaction chamber. A reaction within the at least one reaction chamber is subsequently detected.

Additional devices designed to reduce evaporation of fluid from the device are also provided. In general, such devices comprise a cavity that is part of a microfluidic network formed in an elastomeric substrate; and a plurality of guard channels overlaying the cavity and separated from the cavity by an elastomeric membrane. The guard channel in such devices is sized (i) to allow solution flow therethrough, and (ii) such that there is not a substantial reduction in solution flow in, out or through the cavity due to deflection of the membrane(s) upon application of an actuation force to the guard channels. Other such devices include (i) one or more flow channels and/or one or more reaction chambers; and (ii) a plurality of guard channels overlaying the microfluidic system and separated therefrom by elastomer, wherein the spacing between guard channels is between 1 µm to 1 mm. In other devices the spacing is between 5 µm and 500 µm, in other devices between 10 µm and 100 µm, and in still other devices between 40 µm and 75 µm.

Compositions for performing immunological analyses in reaction chambers of microfluidic devices are also provided. Certain such compositions include one or more of the following: an agent that blocks protein binding sites on an elastomeric material and a detergent. The blocking agent is typically selected from the group consisting of a protein (e.g., gelatin or albumin, such as bovine serum albumin (BSA)). The detergent can be, for example, SDS or Triton.

BRIEF DESCRIPTION OF THE DRAWINGS

FIG. 14A is the labeled detail of structure 14A in FIG. 14. The drawing details the valve and matrix flow channel structure of an embodiment of a microfluidic chip.

DETAILED DESCRIPTION

Definitions

Figure 1A:
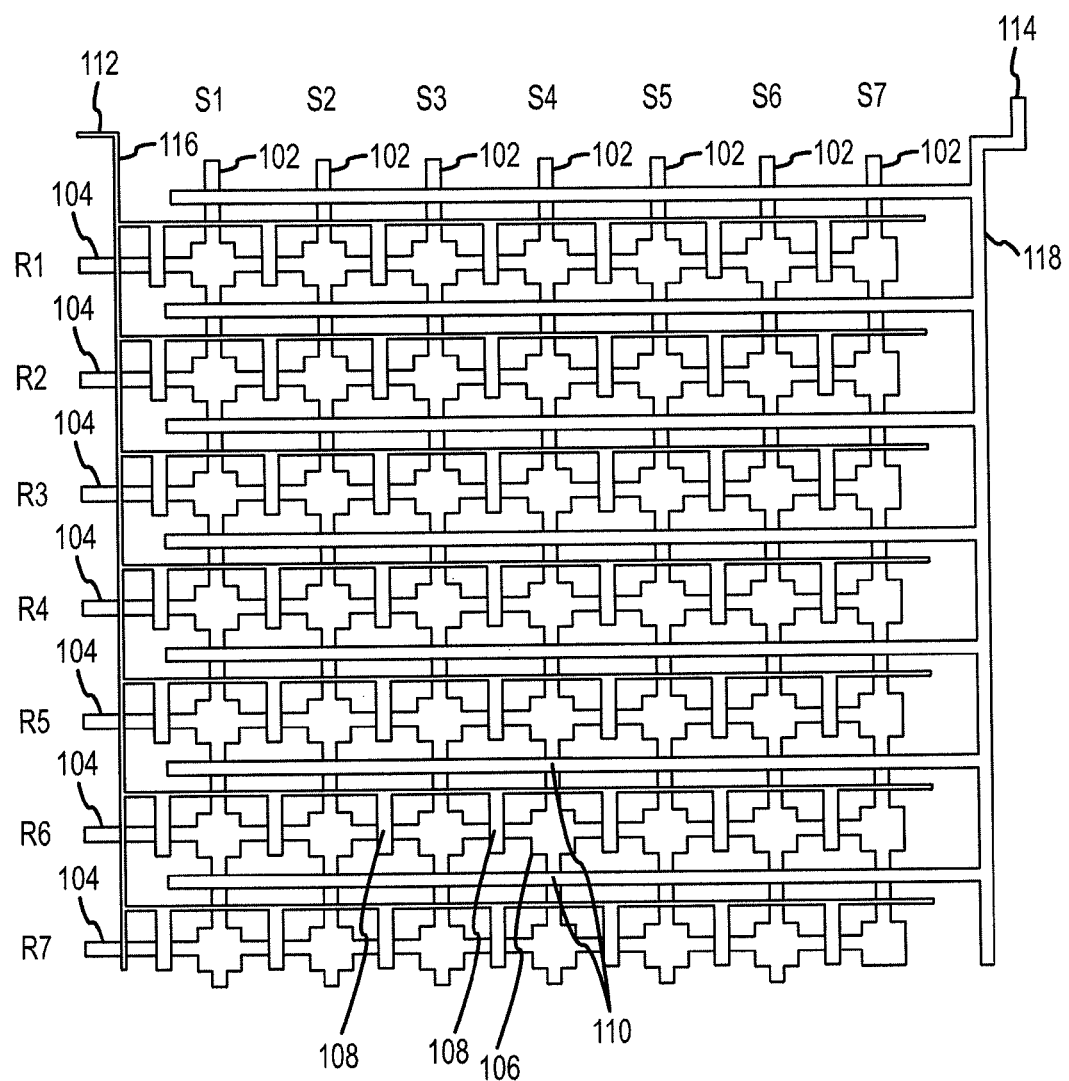
FIG. 1A is a schematic representation of an exemplary device with a matrix design of intersecting vertical and horizontal flow channels.

Unless defined otherwise, all technical and scientific terms used herein have the meaning commonly understood by a person skilled in the art to which this invention belongs. As used herein, the following terms have the meanings ascribed to them unless specified otherwise.

A "flow channel" refers generally to a flow path through which a solution can flow.

The term "valve" unless otherwise indicted refers to a configuration in which a flow channel and a control channel intersect and are separated by an elastomeric membrane that can be deflected into or retracted from the flow channel in response to an actuation force.

A "blind channel" or a "dead-end channel" refers to a flow channel which has an entrance but not a separate exit. Accordingly, solution flow in and out of the blind channel occurs at the same location. The process of filling one or more blind channels is sometimes simply referred to as "blind fill."

An "isolated reaction chamber" generally refers to a reaction chamber that is not in fluid communication with other reactions sites present on the device. When used with respect to a blind channel, the isolated reaction chamber is the region at the end of the blind channel that can be blocked off by a valve associated with the blind channel.

A "via" refers to a channel formed in an elastomeric device to provide fluid access between an external port of the device and one or more flow channels. Thus, a via can serve as a sample input or output, for example.

The term "elastomer" and "elastomeric" has its general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application.

Some of the microfluidic devices described herein are fabricated from an elastomeric polymer such as GE RTV 615 (formulation), a vinyl-silane crosslinked (type) silicone elastomer (family). However, the present microfluidic systems are not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in Unger et al. (2000) Science 288:113-116, and PCT Publications WO 02/43615, and WO 01/01025, which are incorporated herein by reference in their entirety for all purposes.

The term "label" refers to a molecule or an aspect of a molecule that can be detected by optical, physical, chemical, electromagnetic and other related analytical techniques. Common detectable labels that can be utilized with the invention are biotin/avidin labels such as biotinylated antibodies used with labeled streptavidin Other labels include radioisotopes, fluorophores, chromophores, mass labels, electron dense particles, magnetic particles, spin labels, molecules that emit chemiluminescence, electrochemically active molecules, enzymes, cofactors, enzymes linked to nucleic acid probes and enzyme substrates. The term "detectably labeled" means that an agent has been conjugated with a label or that an agent has some inherent characteristic (e.g., size, shape or color) that allows it to be detected without having to be conjugated to a separate label.

A "reagent" refers broadly to any agent used in a reaction. A reagent can include a single agent which itself can be monitored (e.g., a substance that is monitored as it is heated) or a mixture of two or more agents. A reagent may be living (e.g., a cell) or non-living. Exemplary reagents for ELISA reactions may commonly include, but are not limited to: antibodies, antigens, markers, alkaline phosphatase stabilizers, biotin compounds such as esters, enzymes, biotin-AP, D-biotin etc, blocking peptides such as G protein subunit blocking peptides, bovine blocking peptides, human blocking peptides etc, blocking reagents such as alkaline phosphatase blockers, avidin/biotin blockers, BAS blockers etc. Reagents for cell-based reactions include, but are not limited to, cells, cell specific dyes and ligands (e.g., agonists and antagonists) that bind to cellular receptors.

A "ligand" is any molecule for which there exists another molecule (i.e., an "antiligand") that specifically or non-specifically binds to the ligand, owing to recognition of some portion of the ligand by the antiligand.

Overview

A number of different microfluidic devices (also sometimes referred to as chips) having unique flow channel architectures are provided herein, as well as methods for using such devices to conduct a variety of high throughput analyses.

The devices are designed for the performance of multiple simultaneous immunological, chemical or biological reactions.

Each microfluidic device comprises a plurality of reaction chambers (also called reaction cells). Each reaction chamber is in fluid communication with at least one sample inlet (or sample chamber) and/or at least one reagent inlet (or reagent chamber). In various embodiments, the reaction chamber is also in fluid communication with other inlets used for inputting wash solution or another reagent or sample. Fluid communication is provided by one or more flow channels through which the reagent, sample or wash solution(s) flow. Additionally the device of the invention may have one or more waste outlets that allow for the outflow of excess fluids such as sample or reagent or wash fluids.

In certain embodiments, the fluid communication between the reaction chamber and the various inlets and outlets and chambers may be interruptible, and the flow channels may be opened or closed by use of a valve. Closure of the valves may be complete or partial.

In certain embodiments, the sample chamber and reagent chamber are in fluid communication through an interface channel having an interface valve associated therewith for controlling fluid communication between the sample chamber and reagent chamber. The device may include a plurality of sample inlets each in fluid communication with said sample chambers; and a plurality of reagent inlets each in fluid communication with said reagent chambers.

In certain embodiments, reaction chambers may be sealed one form the other by the closing of valves. This is useful where a reaction is occurring within a volume of a fluid or where two reaction fluids are introduced into a chamber contemporaneously so that a particular chemistry may be affected. But in certain embodiments used for immunological applications, valves may not be used, as the immunological processes take place at the surface of the reaction chambers or lumens, and not within a fluid contained within a sealed reaction chamber.

In some embodiments used with immunological (ELISA) applications, the device includes a plurality of inlets for a primary antibody, and a plurality of inlets for a secondary antibody, and one or more wash inlets. The number of inlets corresponds to the number of samples and the number of antibody pairs used with the device. In one exemplary embodiment (FIG. 5) the device includes inlets for 24 samples and for 24 antibody pairs (that is, 24 inlets for the primary antibody and 24 inlets for the secondary antibody). In another exemplary embodiment (FIG. 6) the device includes inlets for 96 samples and for 24 antibody pairs. Any number of samples and antibody pairs may theoretically be used and any number of desired inlets and lumens may be engineered into a chip. In certain embodiments, for example, the microfluidic device or the invention may be a "96×96 chip" having 96 sample wells, 96 primary antibody inlets and 96 secondary antibody inlets, one or more wash inlets, and one or more waste inlets. Microfluidic chips may have from 1 to about 1000 inlets for introducing samples, reactants, detection reagents, primary antibodies and/or secondary antibodies. Other exemplary chip formats are 24×24, 24×96, 50×50, 50×96, 100×100, 250×250, 250×500, 500×500, 500×1000, and 1000×1000.

Some of the microfluidic devices utilize a design typically referred to herein as "blind channel" or "blind fill" are characterized in part by having a plurality of blind channels, which, as indicated in the definition section, are flow channels having a dead end or isolated end such that solution can only enter and exit the blind channel at one end (i.e., there is not a separate inlet and outlet for the blind channel). These devices require only a single valve for each blind channel to isolate a region of the blind channel to form an isolated reaction chamber. During manufacture of this type of device, one or more reagents for conducting an analysis are deposited at the reaction chambers, thereby resulting in a significant reduction in the number of input and outputs. Additionally, the blind channels are connected to an interconnected network of channels such that all the reaction chambers can be filled from a single, or limited number, of sample inputs. Because of the reduction in complexity in inputs and outputs and the use of only a single valve to isolate each reaction chamber, the space available for reaction chambers is increased. Thus, the features of these devices means that each device can include a large number of reaction chambers (e.g., up to tens of thousands) and can achieve high reaction chamber densities (e.g., over 1,000-4,000 reaction chambers/$cm^2$). Individually and collectively, these features also directly translate into a significant reduction in the size of these devices compared to traditional microfluidic devices.

An embodiment of the invention is a microfluidic chip comprising: a plurality of flow channels formed as a matrix defining reaction chambers that are arranged in a plurality of fluidic columns and a plurality of fluidic rows, a first plurality of valves that upon actuation turn off fluidic communication through the fluidic rows of the matrix while permitting flow through the fluidic columns of the matrix, a second plurality of valves that upon actuation turn off fluidic communication through columns of the matrix while permitting flow through the fluidic rows of the matrix, and a plurality of dedicated flushing channels that are addressable to switch between flushing the fluidic columns and flushing the fluidic rows. The embodiment described above may be further described wherein the chip is partially comprised of an elastomeric material or is fully comprised of an elastomeric material. A microfluidic chip according to the above embodiments includes the embodiment wherein the elastomeric material is non-opaque. The microfluidic chips described above can be further described wherein each of the fluidic columns comprises a first row flow channel segment that defines the top of each of the fluidic columns and each of the fluidic columns has a last row flow channel segment that defines the bottom of each of the fluidic columns wherein the first row flow channel segments each comprise a first flow channel segment connection channel in fluid communication with the first row flow channel segment for each column of the matrix and wherein each of the fluidic columns the last row flow channel segments comprise a second flow channel segment connection channel in fluid communication with the last row flow channel segments for each fluidic column of the matrix. This example of an embodiment can be further described wherein each of the plurality of first row flow channel connection segments is fluidically bifurcated into a first inlet channel and a first outlet channel and each of the plurality of last row flow channel connection segments is fluidically bifurcated into a second inlet channel and a second outlet channel.

The microfluidic chips of the invention can be further described wherein each first inlet channel, each first outlet channel, each second inlet channel, and each second outlet channel further comprises an addressable valve for stopping fluidic communication through each first inlet channel, each first outlet channel, each second inlet channel, and each second outlet channel. The reaction chambers defined in the matrix may further comprise a first flush inlet and a second flush inlet.

A microfluidic chip according to the description above is provided for wherein each reaction chamber is comprised of a flow channel with a first end opening and a second end opening that define a length of the reaction chamber wherein ½ of the length of the reaction chamber defines a reaction chamber midpoint demarking a first zone of the reaction chamber and a second zone of the reaction chamber wherein the first flush inlet fluidically communicates with the first zone of the reaction chamber and the second flush inlet fluidically communicates with the second zone of the reaction chamber. These microfluidic chip are further provided for wherein the communication of the first flush inlet with the reaction chamber and the communication of the second flush inlet with the reaction chamber is spaced a distance that is about ¼ or greater of the length of the reaction chamber. The above microfluidic chips are further provided for wherein the communication of the first flush inlet with the reaction chamber and the communication of the second flush inlet with the reaction chamber is spaced a distance that is about ½ or greater of the length of the reaction chamber. As will be apparent, the geometries of these embodiments may be described as serpentine or may be functionally described as having serpentine flow. Other non-coaxial communication of the interconnecting flow channels in a matrix column will likewise serve to provide for efficient flushing of the column flow channels when such geometries are adopted. As such, non-laminar flow through the flow channels of the matrix columns is preferred.

A microfluidic chips according to above embodiments may have individual reaction chamber volumes in the ranges of between about 0.01 mL to about 10 uL. However, reaction chamber volumes of between about 0.01 mL to about 100 nl, or between about 0.01 nL and 10 nL may be advantageous in certain applications. Some embodiments may optimally perform when the volume of each reaction chambers is between about 0.20 nL to about 5 nL. An additional embodiment of the microfluidic chips is where the volume of each reaction chambers is between about 0.25 nL to about 2 nL. Other possible reaction chamber volumes are detailed in this specification.

An embodiment of a microfluidic chip according to any of the above embodiments is provided for wherein the chip comprises 432 or greater reaction chambers. Embodiments of microfluidic chips are further provided for wherein the chip comprises 864 or greater reaction chambers. Additional embodiments of microfluidic chips of the invention are provided for wherein the chip comprises 4608 or greater reaction chambers Other embodiments of the present microfluidic devices include an immunomatrix chip comprising the microfluidic chip according to any one of the above embodiments wherein a plurality of reaction chambers contain an immunological assay reagent. The term "immunomatrix" is used when referring to the chips that are designed for or are intended to be used for immunoassay applications. The general design should not be viewed as limited to immunoassays. The microfluidic chips of the invention can be used for virtually any binding assay with any type of ligand and is not limited to antigens, antibodies, proteins, receptors, bacteria or bacterial fragments or products, whole virus, virus particles, fragments, or products, mammalian, reptilian, avian, insect, plant, or fungal cells, cell fragments, constituents or products.

An embodiment of the present invention is a microfluidic chip for performing immunoassays comprising a plurality of reaction chambers configured to reduce antibody crosstalk, the chambers having a volume of less than 5 nL per chamber and wherein the immunoassay sensitivity is less than about $1\times10^3$ pg/mL and the dynamic range of the assay is equal to or greater than about $1\times10^2$. These microfluidic chips may also be described the chambers have a volume of less than 1 nL. The chambers of the embodied microfluidic chips may also have reaction chambers that have a plurality of flow channel inlets comprising a first inlet for the introduction of a primary antibody and a second inlet for the introduction of a secondary antibody. The reaction chambers of the embodied microfluidic chips may further comprise a third inlet for the introduction of a sample. The chips of this embodiment may be comprised of an elastomer. The microfluidic chips, in further embodiments, further comprise a control channel separated from a flow channel by a deflectable membrane. Such chips as those described above are provided for wherein each flow channel that is in communication with the reaction chamber is separated from a control channel by a deflectable membrane. The chips of the above embodiments may further comprising a binding protein and still further comprise a primary antibody bound to the binding protein. The chips may further comprise a linker molecule and a reagent wherein the linker covalently attaches the reagent to the reaction chamber. The devices embodied herein may comprise a microfluidic device comprising a microfluidic chip according to any of the above described embodiments in fluidic communication with a plurality of flow channels on a rigid carrier. The plurality of flow channels on the rigid carrier may be in fluid communication with liquid reservoir wells on the rigid carrier. Microfluidic devices as described above may further comprise one or multiple accumulators for the storage of fluidic pressure attached to the rigid carrier, the accumulator being in fluidic communication with the microfluidic chip. This embodiment may further comprise an accumulator for the storage of fluidic pressure attached to the rigid carrier, the accumulator being in fluidic communication with the microfluidic chip.

An assay system comprising a microfluidic device according to the above embodiments and a programmable reader is also provided for. The system may further comprise a microprocessor such as a computer for control of the assay system. A programmable controller may also be part for controlling the operation of the microfluidic chip or microfluidic device. Such a controller may have internal and/or external pressure sources. The assay system may also be configured for real time data collection.

The microfluidic chips and devices, when used with chip controllers may perform 432 or greater simultaneous immunoassays in less than 6 hours or may perform 864 or greater simultaneous immunoassays in less than 6 hours. A microfluidic device of the present invention may have a detection limit for an immunoassay of about 50 pg/mL of sample, about 40 pg/mL of sample, about 30 pg/mL of sample, about 25 pg/mL of sample, about 20 pg/mL of sample, about 15 pg/mL of sample, about 10 pg/mL of sample, about 5 pg/mL of sample or about 1, 2, or 3 pg/mL of sample. Dynamic ranges may run from about $1\times10^2$ to about $1\times10^4$ with ranges from about $1\times10^2$ to about $1\times10^3$ being typical.

Also embodied in the present invention are methods for controlling a microfluidic device as detailed below and also embodied are methods for detecting and measuring ligands of interest and in particular when the ligand is an antigen. Methods of using the microfluidic devices of the present invention to detect and or measure ligands such as antigens, antibodies, proteins, receptors, bacteria or bacterial fragments or products, whole virus, virus particles, fragments, or products, mammalian, reptilian, avian, insect, plant, or fungal cells, cell fragments, constituents or products are embodied herein.

For immunological applications, the devices of the invention may be used to screen hundreds or even thousands of different antibodies against one or more protein samples, or to screen hundreds or thousands of different protein samples against an array of known antibodies.

At this point it should be emphasized that immunological assays may be used to detect non-proteins, and the current invention may be used to detect or quantify any species against which an antibody may be raised. These include lipids, carbohydrates, inorganic and organic chemicals and combinations of the foregoing.

Other microfluidic devices that are disclosed herein utilize a matrix design. In general, microfluidic devices of this type utilize a plurality of intersecting horizontal and vertical flow channels to define an array of reaction chambers at the points of intersection. Channels on different levels may be linked by vertical channels called vias. Thus, devices of this design also have an array or reaction chambers; however, there is a larger number of sample inputs and corresponding outputs to accommodate the larger number of samples with this design. A valve system referred to as a switchable flow array architecture enables solution be flowed selectively through just the horizontal or flow channels, thus allowing for switchable isolation of various flow channels in the matrix. Hence, whereas the blind channel devices are designed to conduct a large number of analyses under different conditions with a limited number of samples, the matrix devices are constructed to analyze a large number of sample under a limited number of conditions. Still other devices are hybrids of these two general design types. Any of these architectures may be employed to conduct immunological assays.

In some embodiments, the microfluidic devices that are described are further characterized in part by utilizing various components such as flow channels, control channels, valves and/or pumps from elastomeric materials. In some instances, essentially the entire device is made of elastomeric material. Consequently, such devices differ significantly in form and function from the majority of conventional microfluidic devices that are formed from silicon-based material.

The array format and high throughput capabilities of the devices make them useful for performing large numbers of immunological (e.g., ELISA) or protein-ligand experiments and assays. Such assays include assays for the detection of proteins and polypeptides. Such assays may be useful for diagnostic purposes such as for the detection of viral antigens. The devices and methods of the invention may be used for both the quantitative and qualitative detection of antigens and/or antibodies. The devices and methods of the invention may also be used to detect antibodies, for example antibodies produced in response to a disease or antibodies that are indicative of a particular disease.

In another embodiment, the devices and methods of the invention may be used to concentrate and purify a desired protein. In such an application, the microfluidic device of the invention may be used to perform chromatography for the isolation and concentration of a desired protein.

Figure 5:
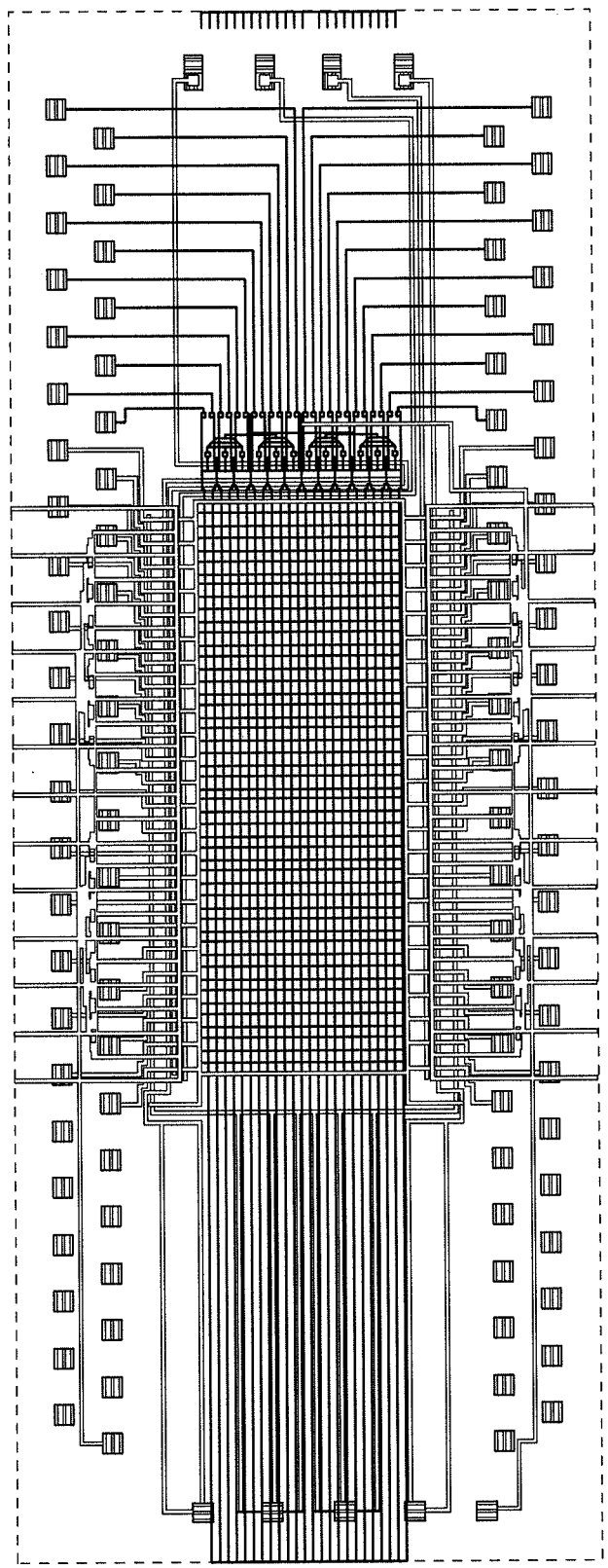
FIG. 5 is a schematic drawing of one "immunochip" embodiment of the device having 24 sample inputs and 24 primary antibody inputs, and 24 secondary antibody inputs.
Figure 6:
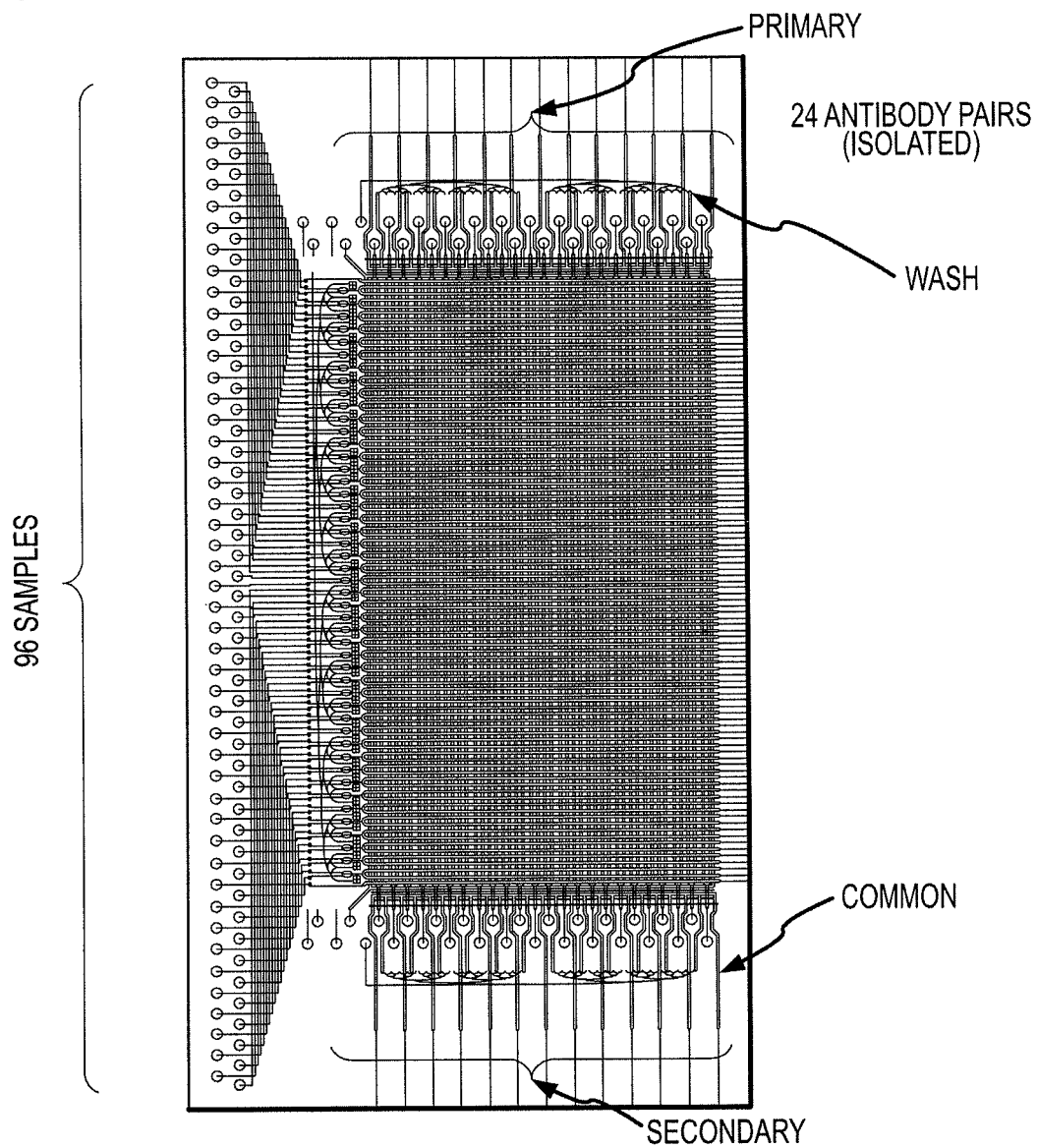
FIG. 6 is a schematic drawing of another embodiment of the device having 96 sample inputs and 24 primary antibody inputs, and 24 secondary antibody inputs.
Figure 7:
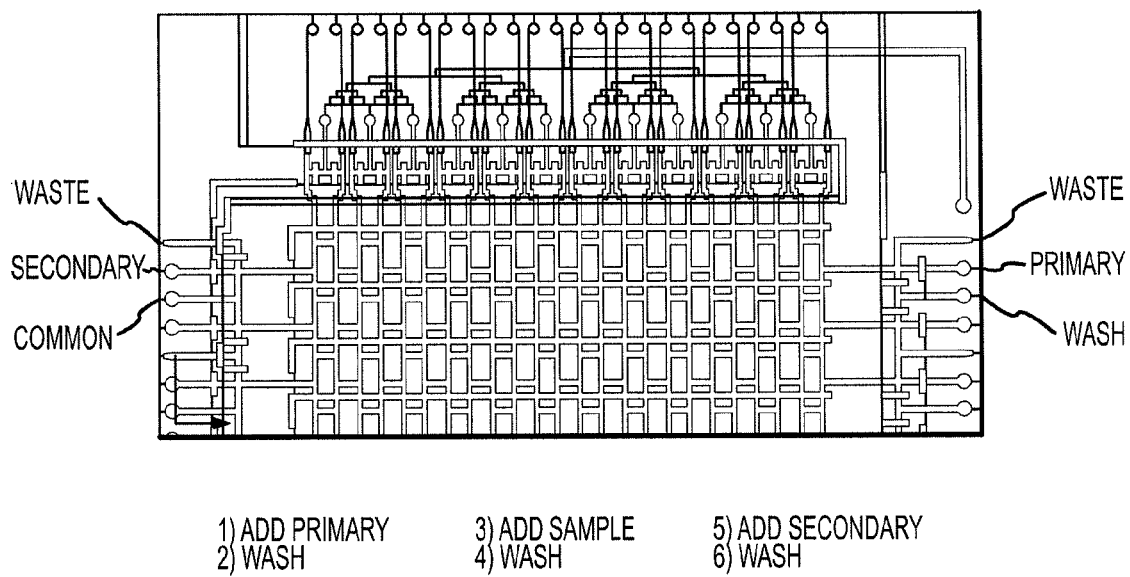
FIG. 7 is a schematic drawing showing a magnified section of an embodiment the device. The primary inlet is the inlet through which the primary antibody is introduced. The secondary is the inlet through which the secondary antibody is introduced. The wash inlet is the inlet through which washing solution is introduced. The two waste outlets are the outflows through which the excess reactant fluid (of any kind) is expelled. In use, the blocking solution is flowed through the lumens of the chip via the common inlet. The primary antibody solution is then introduced through the primary inlet and flows through the lumens of the chip and through the reaction chambers. A wash solution is then flowed through all the lumens and chambers to remove unbound primary antibody. The secondary antibody solution is introduced through the secondary inlet and flows through the lumens of the chip and through the reaction chambers. Another wash solution is then flowed through all the lumens and chambers to remove unbound secondary antibody. The enzyme solution is then introduced, followed by another washing step, followed by the substrate solution, followed by a final wash step. A signal is thus produced and measured.
Figure 8:
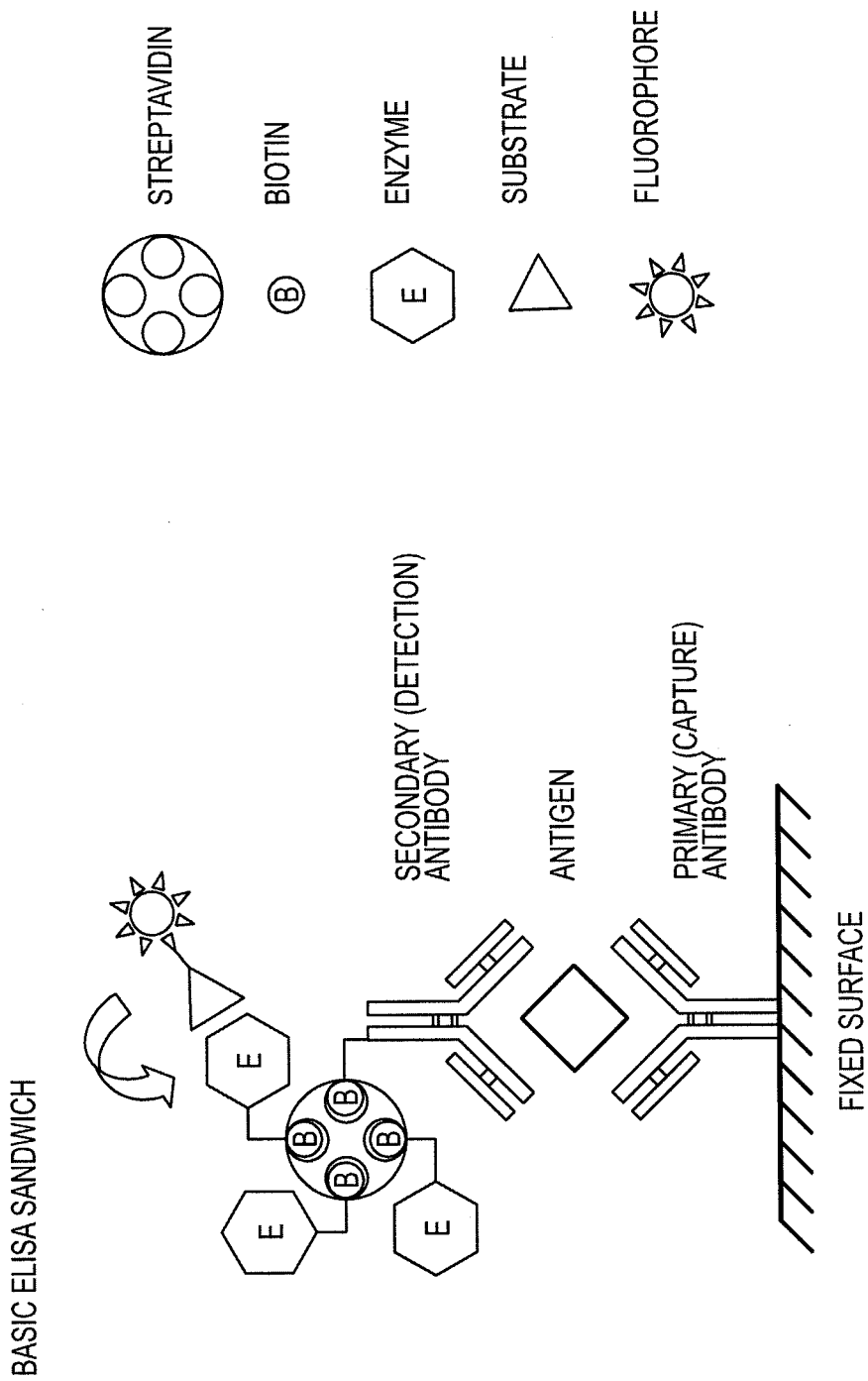
FIG. 8 is a schematic drawing of an ELISA sandwich assay showing a protein A which is used as a binding substrate to bind to the PDMS. The Fc portion of the IgG primary antibody binds to protein A. The Fab portion of the primary antibody binds the ligand (sample). The Fab portion of the secondary antibody (labeled) binds the ligand at a second epitope. The label is bound to the Fc portion of the secondary antibody.
Figure 9:
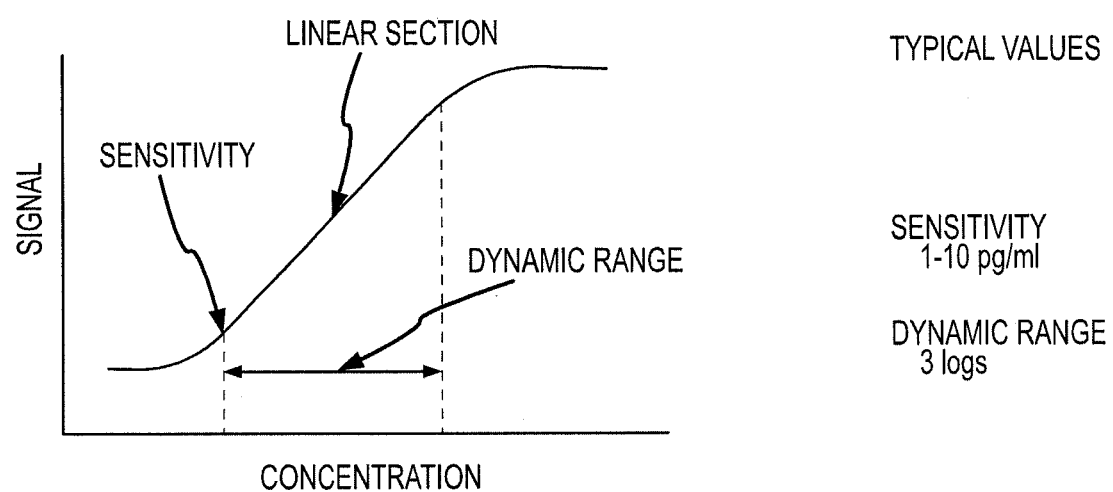
FIG. 9 is a graph showing how the relationship between signal and protein concentration is used to calculate dynamic range.
Figure 10:
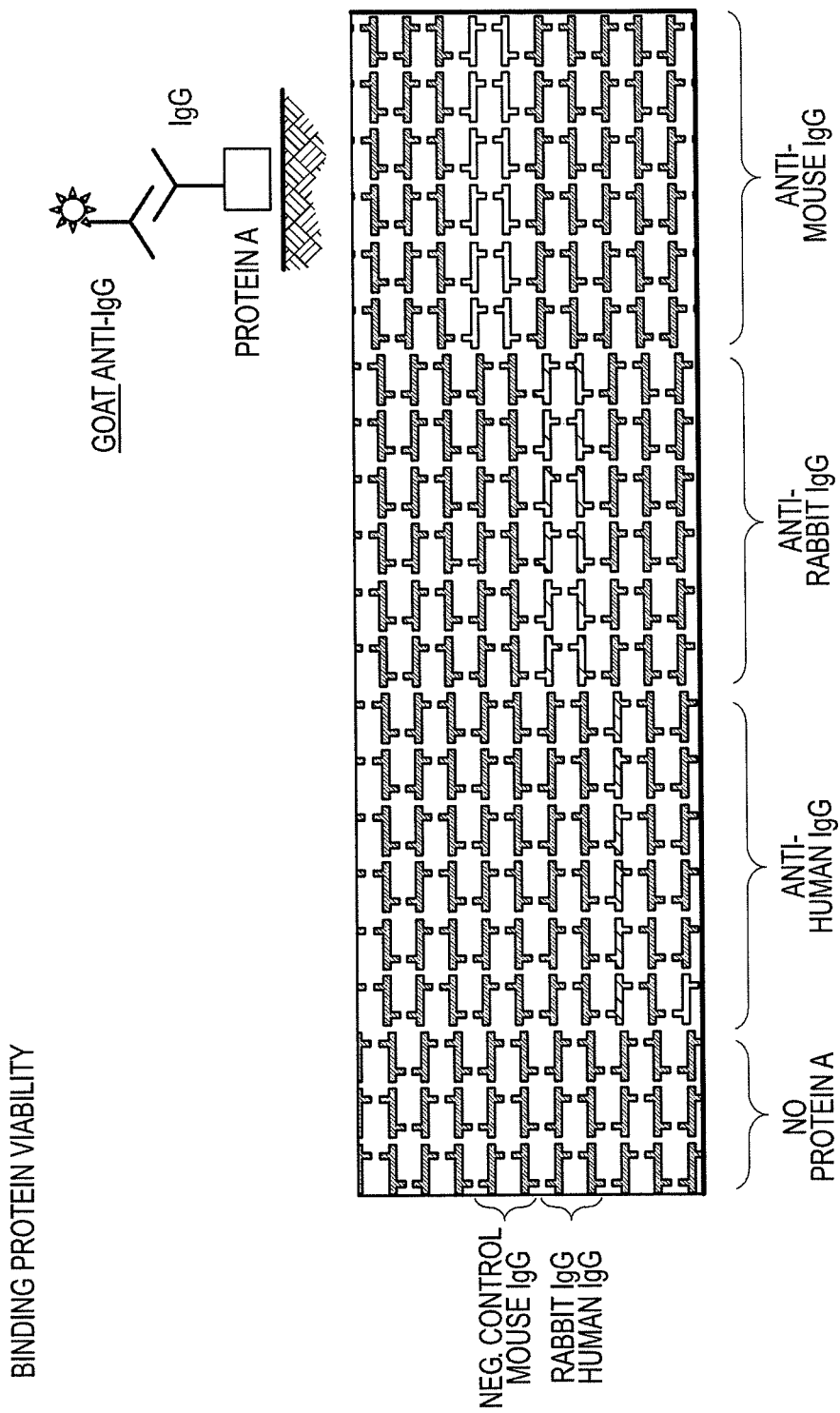
FIG. 10 is a photograph of an immunological microfluidic control chip experiment demonstrating binding specificity for various antibody pairs.
Figure 11:
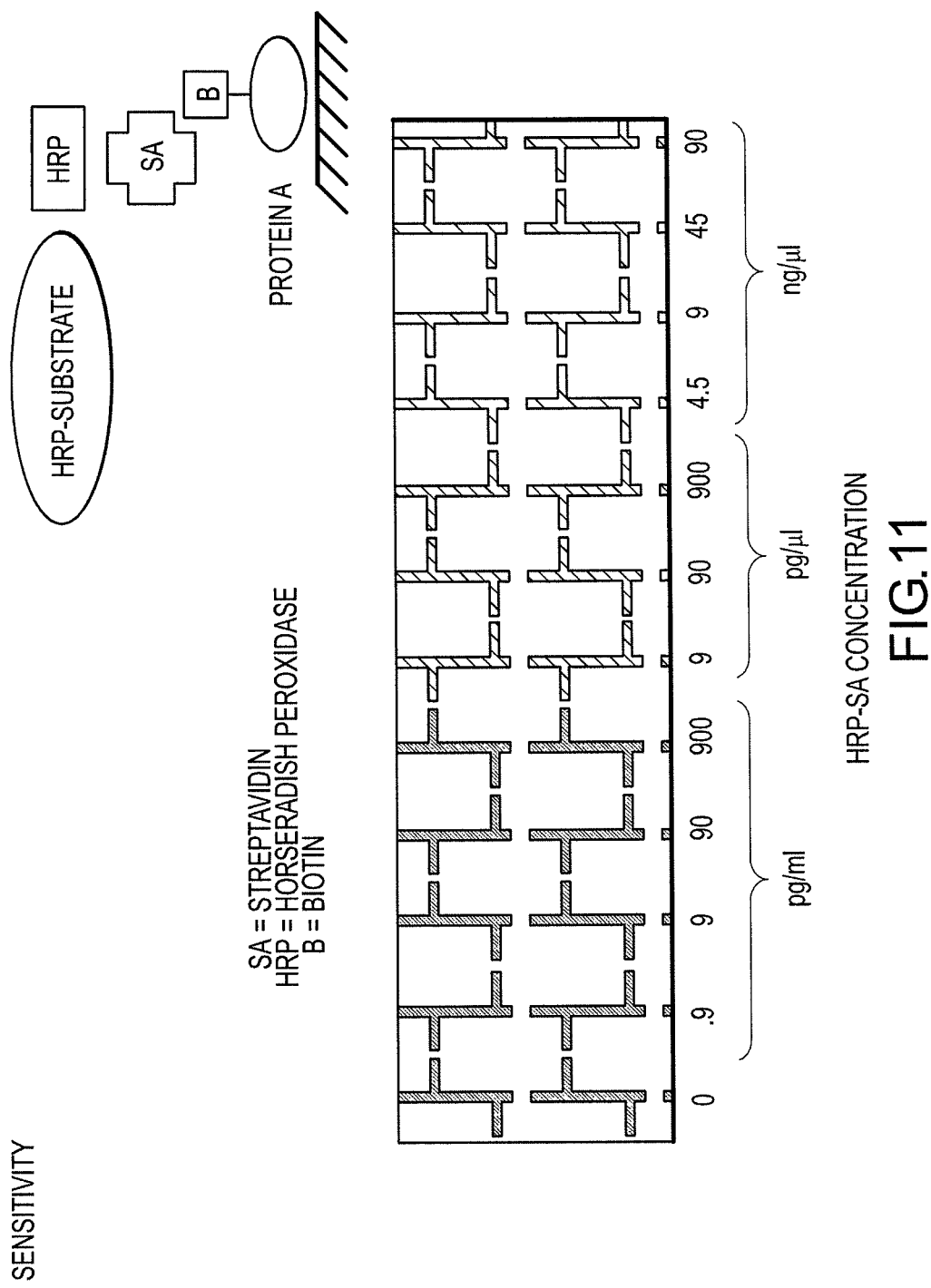
FIG. 11 is a photograph of an immunological microfluidic control chip experiment demonstrating the sensitivity of the device using a biotin/streptavidin/Horseradish peroxidase system. A signal can be detected into the pg/ml range.
Figure 12:
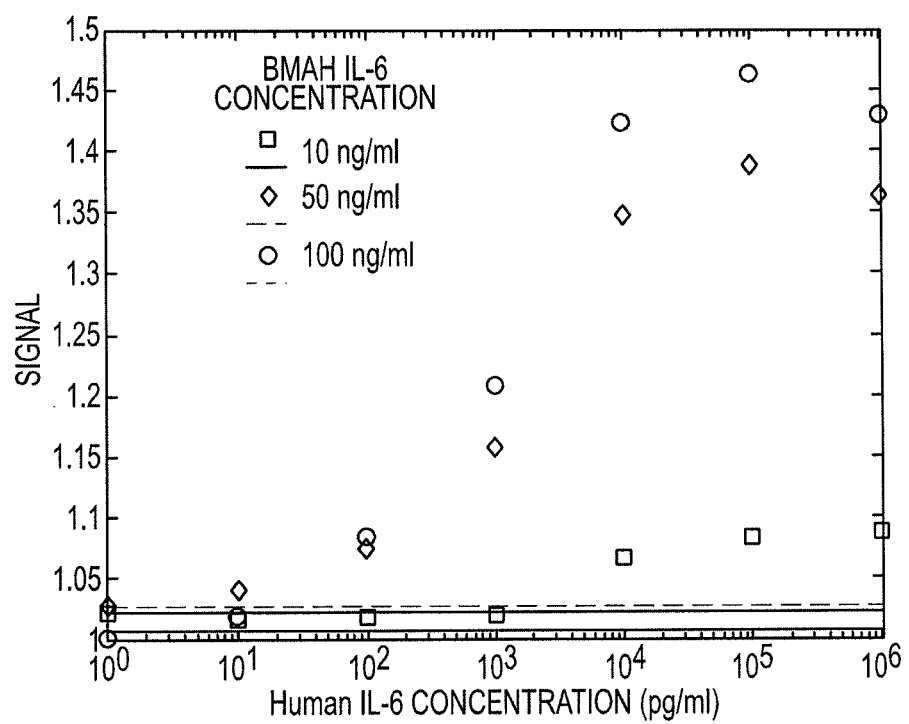
FIG. 12 is a graph of IL-6 concentration (x) vs signal (y) demonstrating the sensitivity of the system.
Figure 13A:
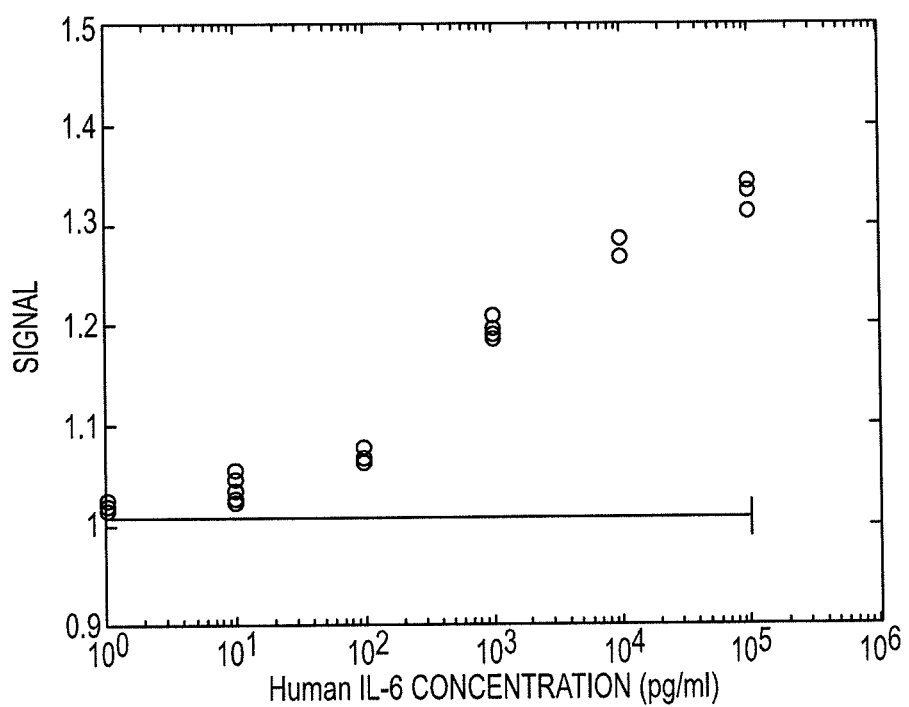
FIG. 13A shows the dynamic range of the system for an ELISA assay for human IL-6 measured in an experiment performed on a microfluidic chip.
Figure 13B:
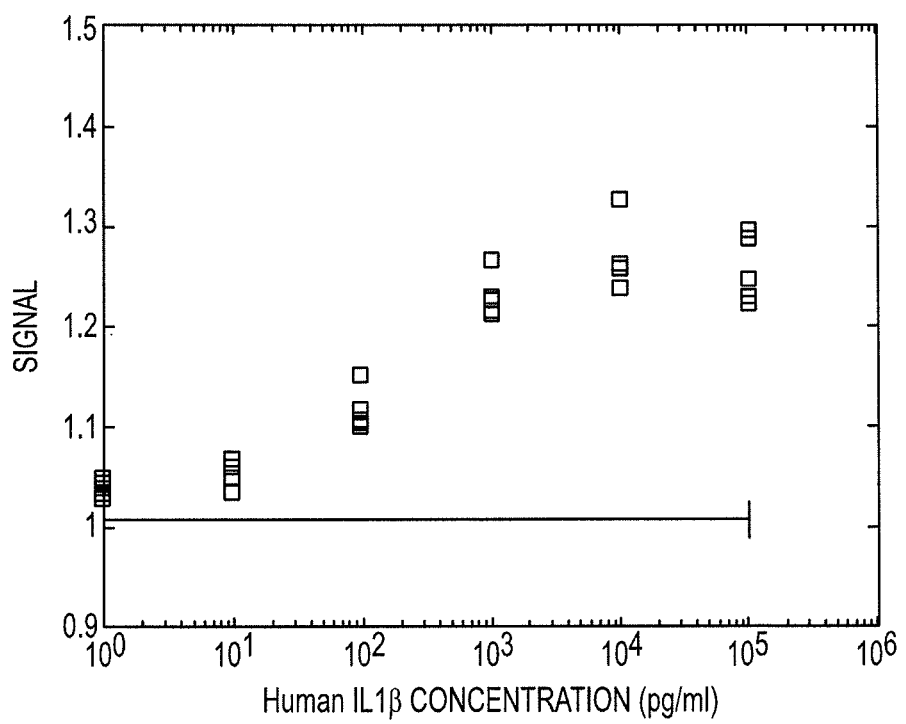
FIG. 13B shows the dynamic range of the system for an ELISA assay for human IL1β measured in an experiment performed on a microfluidic chip.
Figure 13C:
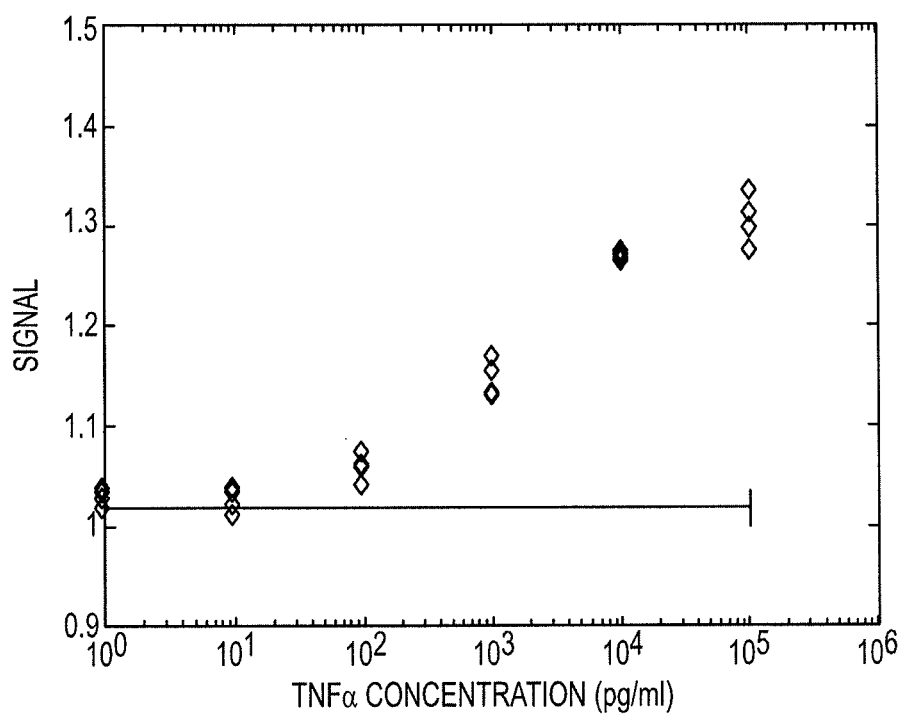
FIG. 13C shows the dynamic range of the system for an ELISA assay for TNFα measured in an experiment performed on a microfluidic chip.
Figure 13D:
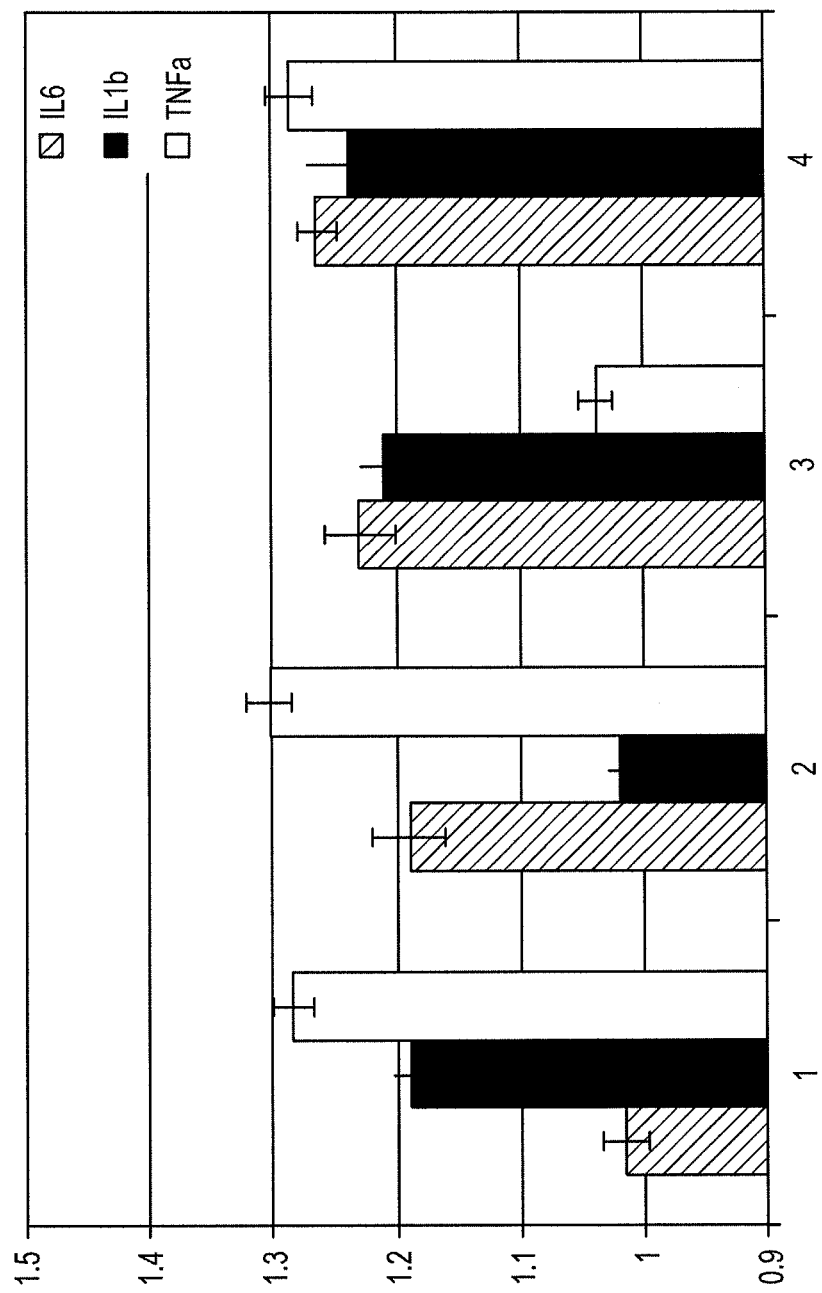
FIG. 13D shows the dynamic range of the system for an ELISA assay for measured in an experiment performed on a microfluidic chip.

Immunoassays such as ELISA assays are of particular interest in the present disclosure. The embodiments shown in FIGS. 5-7 show a schematic representation of a device used to practice the invention. The primary inlet is the inlet through which the primary antibody is introduced. The secondary is the inlet through which the secondary antibody is introduced. The wash inlet is the inlet through which washing solution is introduced. The two waste outlets are the outflows through which the excess reactant fluid (of any kind) is expelled. In use, the primary antibody solution is introduced through the primary inlet and flows through the lumens of the chip and through the reaction chambers. A wash solution is then flowed through all the lumens and chambers to remove unbound primary antibody. The secondary antibody solution is introduced through the secondary inlet and flows through the lumens of the chip and through the reaction chambers. Another wash solution is then flowed through all the lumens and chambers to remove unbound secondary antibody. The enzyme solution is then introduced, followed by another washing step, followed by the substrate solution, followed by a final wash step. A signal is thus produced and measured.

In particular the present invention provides microfluidic devices with the ability to conduct many simultaneous experiments with no cross-talk between the antibodies. Cross-talk is eliminated by physically isolating each primary and secondary antibody in the panel. Each primary antibody is delivered through a separate primary delivery channel, into a reaction chamber. These reaction chambers are then flowed through with a sample containing the target antigen, and then flowed through with a second antibody which is also separate and delivered via a second inlet.

The isolation and separate delivery of the secondary antibody to the reception chambers is fundamental to eliminating potential cross-talk between all antibodies in the panel. Current systems combine the secondary antibodies into a single cocktail which is used to flood the assay cambers. This cocktail may contain antibodies that will cross-talk with other antibodies (e.g. secondary antibodies may bind non-specifically with primary antibodies). This cross-talk problem requires users to employ the very laborious process of screening individual pairs of antibodies against one another to determine cross-talk and therefore identify the "poor quality" antibodies that produce the false positives.

One major advantage of the invention is the ability to perform many simultaneous experiments with no cross-talk between the antibodies. Other advantages are demonstrated in FIGS. 9-13 that show the dynamic range and sensitivity of the invention for various control proteins such as IL-6, IL-I alpha and TNF beta. The invention shows superior dynamic range and sensitivity at a level that can detect proteins within a picogram per milliliter range.

The devices can be utilized in a wide variety of other types of analyses or reactions. Examples include analyses of protein-ligand interactions and interactions between cells and various compounds. Further examples are provided infra.

General Structure of Microfluidic Devices
Pumps and Valves

The microfluidic devices disclosed herein are typically constructed at least in part from elastomeric materials and constructed by single and multilayer soft lithography (MSL) techniques and/or sacrificial-layer encapsulation methods (see, e.g., Unger et al. (2000) Science 288:113-116, and PCT Publication WO 01/01025, both of which are incorporated by reference herein in their entirety for all purposes). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, solution flow can be slowed or entirely blocked through the flow channel. Using combinations of control and flow channels of this type, one can prepare a variety of different types of valves and pumps for regulating solution flow as described in extensive detail in Unger et al. (2000) Science 288:113-116, and PCT Publication WO/02/43615 and WO 01/01025.

The devices provided herein incorporate such pumps and valves to isolate selectively a reaction chamber at which reagents are allowed to react. The reaction chambers can be located at any of a number of different locations within the device. For example, in some matrix-type devices, the reaction chamber is located at the intersection of a set of flow channels. In blind channel devices, the reaction chamber is located at the end of the blind channel.

Because the devices are made of elastomeric materials that are relatively optically transparent, reactions can be readily monitored using a variety of different detection systems at essentially any location on the microfluidic device. Most typically, however, detection occurs at the reaction chamber itself (e.g., within a region that includes an intersection of flow channels or at the blind end of a flow channel). The fact that the device is manufactured from substantially transparent materials also means that certain detection systems can be utilized with the current devices that are not usable with traditional silicon-based microfluidic devices. Detection can be achieved using detectors that are incorporated into the device or that are separate from the device but aligned with the region of the device to be detected.

Guard Channels

To reduce evaporation of sample and reagents from the elastomeric microfluidic devices that are provided herein, a plurality of guard channels can be formed in the devices. The guard channels are similar to the control channels in that typically they are formed in a layer of elastomer that overlays the flow channels and/or reaction chamber. Hence, like control channels, the guard channels are separated from the underlying flow channels and/or reaction chambers by a membrane or segment of elastomeric material. Unlike control channels, however, the guard channels are considerably smaller in cross-sectional area. In general, a membrane with smaller area will deflect less than a membrane with larger area under the same applied pressure. The guard channels are designed to be pressurized to allow solution (typically water) to be flowed into the guard channel. Water vapor originating from the guard channel can diffuse into the pores of the elastomer adjacent a flow channel or reaction chamber, thus increasing the water vapor concentration adjacent the flow channel or reaction chamber and reducing evaporation of solution therefrom.

In general, the guard channels are sufficiently small such that when pressurized the membrane that separates the guard channel from the underlying flow channel or reaction chamber does not substantially restrict solution flow in, out, or through the flow channel or reaction chamber which the guard channel overlays. When used in this context, the term "substantially restrict" or other similar terms means that solution flow is not reduced in, out or through the flow channel or reaction chamber by more than 40%, typically less than 30%, usually less than 20%, and in some instances less than 10%, as compared to solution flow in, to or through the flow channel or reaction chamber under the same conditions, when the guard channel is not pressurized to achieve solution flow therethrough. Usually this means that the guard channels have a cross-sectional area of between 100 µm$^2$ and 50,000 µm$^2$, or any integral or non-integral cross-sectional area therebetween. Thus, for example, in some instances, the cross-sectional area is less than 50,000 µm$^2$, in other instances less than 10,000 µm$^2$, in still other instances less than 10,00 µm$^2$, and in yet other instances less than 100 µm$^2$. The guard channels can have any of a variety of shapes including, but not limited to, circular, elliptical, square, rectangular, hexagonal and octahedral shapes.

The guard channels are designed to reduce the evaporation of sample and reagents from the device during the time and under the conditions that it takes to conduct a thermocycling reaction to less than 50%, in other instance less than 45%, 40%, 35%, 30%, 25%, 20%, 15%, 10%, 5% or 1%. The guard channel system is designed to reduce evaporation during approximately this time frame to the foregoing set of limits. To achieve this level of evaporation reduction, the guard channels are typically present at a density of at least 10 lines/cm$^2$ to 1000 lines/cm$^2$, or any integral density level therebetween. More specifically, the guard channels are generally at least 25 lines/cm$^2$, in other instances at least 50 lines/cm$^2$, in still other instances at least 100 lines/cm$^2$, and in yet other instances at least 500 lines/cm$^2$. To achieve this level of evaporation reduction, the guard channels are typically present at a spacing between 1 mm to 1 µm as measured from the outer edge of one line to the nearest outer edge of adjacent line, or any integral density level therebetween. More specifically, the guard channels are generally spaced between 500 µm to 5 µm, in other instances between 100 µm to 10 µm, in still other instances between 75 µm to 40 µm. Thus, the spacing is typically at least 1 µm, but is less than 1 mm, in other instances less than 500 µm, in still other instances less than 400 µm, in yet other instances less than 300 µm, in other instances less than 200 µm, and in still other instances less than 100 µm, 50 µm or 25 µm.

The guard channels can be formed as a separate network of channels or can be smaller channels that branch off of the control channels. The guard channels can extend across the device or only a particular region or regions of the device. Typically, the guard channels are placed adjacent and over flow channels and reaction chambers as these are the primary locations at which evaporation is the primary concern. Exemplary locations of guard channels on certain matrix devices are illustrated in FIG. 1C, and on certain blind channel devices in FIGS. 3B and 3C, and discussed in greater detail infra.

The solution flowed through the guard channel includes any substance that can reduce evaporation of water. The substance can be one that increases the water vapor concentration adjacent a flow line and/or reaction chamber, or one that while not increasing the water vapor concentration nonetheless blocks evaporation of water from the flow line and/or reaction chamber (blocking agent). Thus, one option is to utilize essentially any aqueous solution in which case suitable solutions include, but are not limited to, water and buffered solution (e.g., TaqMan buffer solution, and phosphate buffered saline). Suitable blocking agents include, for example, mineral oil.

Guard channels are typically formed in the elastomer utilizing the MSL techniques and/or sacrificial-layer encapsulation methods cited above.

The following sections describe in greater detail a number of specific configurations that can be utilized to conduct a variety of analyses, including analyses requiring temperature control (e.g., nucleic acid amplification reactions). It should be understood, however, that these configurations are exemplary and that modifications of these systems will be apparent to those skilled in the art.

Matrix Design

General

Devices utilizing the matrix design generally have a plurality of vertical and horizontal flow channel that intersect to form an array of junctions. Because a different sample and reagent (or set of reagents) can be introduced into each of the flow channels, a large number of samples can be tested against a relatively large number of reaction conditions in a high throughput format. Thus, for example, if a different sample is introduced into each of M different vertical flow channels and a different reagent (or set of reagents) is introduced into each of N horizontal flow channels, then M×N different reactions can be conducted at the same time. Typically, matrix devices include valves that allow for switchable isolation of the vertical and horizontal flow channels. Said differently, the valves are positioned to allow selective flow just through the vertical flow channels or just through the horizontal flow channels. Because devices of this type allow flexibility with respect to the selection of the type and number of samples, as well as the number and type of reagents, these devices are well-suited for conducting analyses in which one wants to screen a large number of samples against a relatively large number of reaction conditions. The matrix devices can optionally incorporate guard channels to help prevent evaporation of sample and reactants.

The invention provides for high-density matrix designs that utilize fluid communication vias between layers of the microfluidic device to weave control lines and fluid lines through the device. For example, by having a fluid line in each layer of a two layer elastomeric block, higher density reaction cell arrangements are possible. FIG. 21 depicts an exemplary matrix design wherein a first elastomeric layer (1st layer) and a second elastomeric layer (2d layer) each having fluid channels formed therein. For example, a reagent fluid channel in the first layer is connected to a reagent fluid channel in the second layer through a via, while the second layer also has sample channels therein, the sample channels and the reagent channels terminating in sample and reagent chambers, respectively. The sample and reagent chambers are in fluid communication with each other through an interface channel that has an interface valve associated therewith to control fluid communication between each of the chambers of a reaction cell. In use, the interface is first closed, then reagent is introduced into the reagent channel from the reagent inlet and sample is introduced into the sample channel through the sample inlet, containment valves are then closed to isolate each reaction cell from other reaction cells. Once the reaction cells are isolated, the interface valve is opened to cause the sample chamber and the reagent chamber to be in fluid communication with each other so that a desired reaction may take place.

Accordingly, a preferred aspect of the invention provides for a microfluidic device for reacting M number of different samples with N number of different reagents comprising: a plurality of reaction cells, each reaction cell comprising a sample chamber and a reagent chamber, the sample chamber and the reagent chamber being in fluid communication through an interface channel having an interface valve associated therewith for controlling fluid communication between the sample chamber and the reagent chamber; a plurality of sample inlets each in fluid communication with the sample chambers; a plurality of reagent inlets each in fluid communication with the reagent chambers; wherein one of the sample inlets or reagent inlets is in fluid communication with one of the sample chambers or one of the reagent chambers, respectively, through a via. Certain embodiments include having the reaction cells be formed within an elastomeric block formed from a plurality of layers bonded together and the interface valve is deflectable membrane; having the sample inlets be in communication with the sample chamber through a sample channel and the reagent inlet is in fluid communication with the reagent chamber through a reagent channel, a portion of the sample channel and a portion of the reagent channel being oriented about parallel to each other and each having a containment valve associated therewith for controlling fluid communication therethrough; having the valve associated with the sample channel and the valve associated with the reagent channel are in operable communication with each other through a common containment control channel; having the containment common control channel located along a line about normal to one of the sample channel or the reagent channel Another aspect of the invention provides for a method for making a feature in an elastomeric block comprising the steps of providing a first elastomeric layer; applying a photoresist layer upon a surface of the first elastomeric layer; applying a light pattern to the photoresist layer to form a pattern of reacted photoresist material; removing unreacted photoresist material leaving the pattern of reacted photoresist upon the surface of the first elastomeric layer; applying an etching reagent to the first elastomeric surface to etch the surface of the first elastomeric layer not covered by the pattern of reacted photoresist material thereby removing regions of the first elastomeric layer not covered by the pattern of reacted photoresist and leaving a pattern of the elastomeric layer corresponding to the pattern of reacted photoresist material. In certain preferred embodiments of the method include having a step of removing the pattern of reacted photoresist material; having the removing is caused by applying an adhesive tape to the surface of the elastomeric layer and the pattern of reacted photoresist material, then separating the adhesive tape from the elastomeric layer while some or all of the pattern of reacted photoresist material is removed from the surface of the elastomeric layer; having the photo resist be SU8; having the etching reagent comprises tetrabutylammoniumfluoride-trihydrate; having the feature be a via; having the elastomeric block comprise a plurality of elastomeric layers bonded together, wherein two or more elastomeric layers have recesses formed therein and one recess of one elastomeric layer is in communication with a recess of another elastomeric layer through the via.

Figure 15:
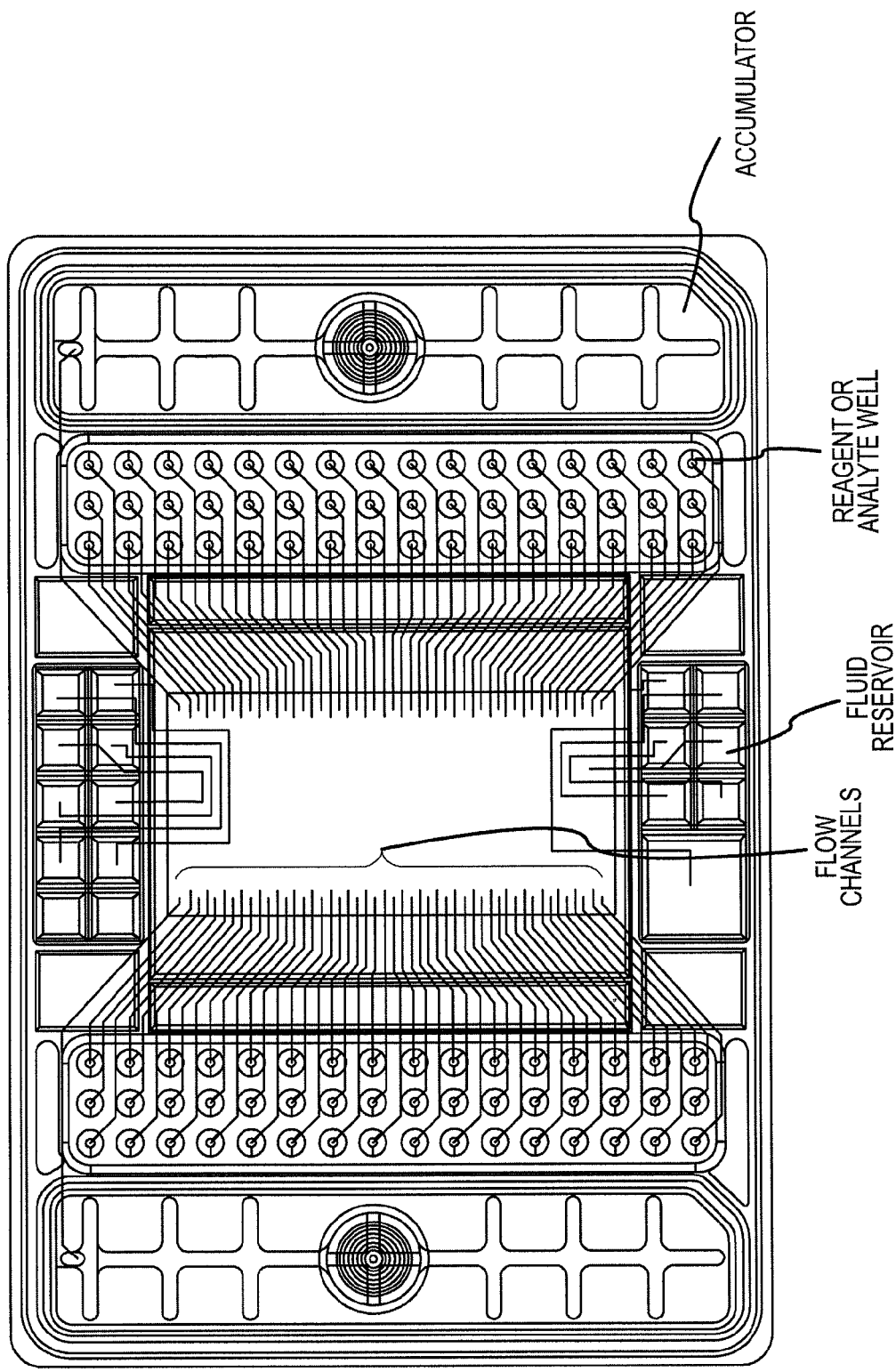
FIG. 15 is a diagram of a carrier to allow for ease of manipulation and control of the microfluidic chips.

The microfluidic devices of the present invention may be further integrated into the carrier devices described in copending and co-owned U.S. patent application Ser. No. 60/557,715 by Unger filed on Mar. 29, 2004, which is herein incorporated for all purposes. The carrier of Unger provides on-board continuous fluid pressure to maintain valve closure away from a source of fluid pressure, e.g., house air pressure. Unger further provides for an automated system for charging and actuating the valves of the present invention as described therein. A rigid carrier for use in the manipulation and control of a microfluidic device embodied by this invention is shown in FIG. 15.

Exemplary Designs and Uses

FIG. 1A provides an illustration of one exemplary matrix device. This device 100 comprises seven vertical flow channels 102 and seven horizontal flow channels 104 that intersect to form an array of 49 different intersections or reaction chambers 106. This particular device thus enables seven samples to be reacted with seven different reagents or sets of reagents. Column valves 110 that regulate solution flow in the vertical direction can be controlled by control channels 118 that can all be actuated at a single inlet 114.

Similarly, row valves 108 regulate solution flow in the horizontal direction; these are controlled by control channels 116 that are actuated by a single control inlet 112. As shown in FIG. 1A, the control channels 116 that regulate the row valves 108 vary in width depending upon location. When a control channel 116 crosses a vertical flow channel 102, the control channel 116 is sufficiently narrow that when it is actuated it does not deflect into the vertical flow channel 102 to reduce substantially solution flow therethrough. However, the width of the control channel 116 is increased when it overlays one of the horizontal flow channels 104; this makes the membrane of the control channel sufficiently large to block solution flow through the horizontal flow channel 104.

In operation, reagents R1-R7 are introduced into their respective horizontal flow channels 104 and samples S1-S7 are injected into their respective vertical flow channels 102. The reagents in each horizontal flow channel 104 thus mix with the samples in each of the vertical flow channels 102 at the intersections 106, which in this particular device are in the shape of a well or chamber. Thus, in the specific case of a nucleic acid amplification reaction, for example, the reagents necessary for the amplification reaction are introduced into each of the horizontal flow channels 104. Different nucleic acid templates are introduced into the vertical flow channels 102. In certain analyses, the primer introduced as part of the reagent mixture that is introduced into each of the horizontal flow channels 104 might differ between flow channels. This allows each nucleic acid template to be reacted with a number of different primers.

Figure 1B:
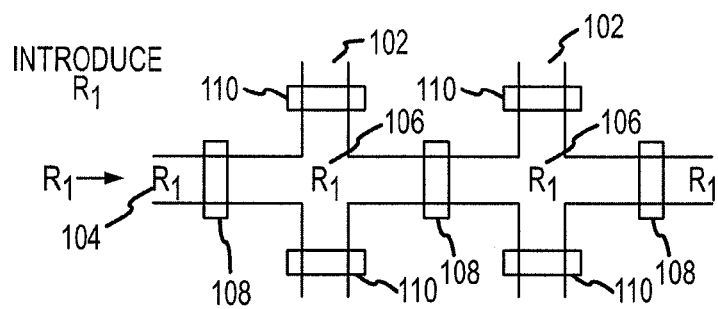
FIGS. 1B-E show enlarged views of a portion of the device shown in FIG. 1A and illustrates its operation.
Figure 1C:
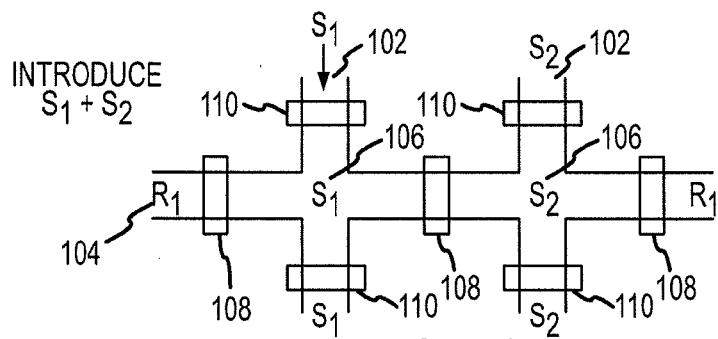

FIGS. 1B-E show enlarged plan views of adjacent reaction chambers in the device depicted in FIG. 1A to illustrate more specifically how the device operates during an analysis. For the purposes of clarity, the intersections 106 are not shown in the form of reaction wells and control channels 116, 118 have been omitted, with just the column and row valves 110, 108 being shown (rectangular boxes). As shown in FIG. 1B, an analysis is commenced by closing column valves 110 and opening row valves 108 to allow solution flow through horizontal flow channel 104 while blocking flow through vertical flow channels 102. Reagent R1 is then introduced into horizontal flow channel 104 and flowed completely through the length of the horizontal flow channel 104 such that all the reaction chambers 106 are filled. Solution flow through horizontal channel 104 can be achieved by an external pump, but more typically is achieved by incorporating a peristaltic pump into the elastomeric device itself as described in detail in Unger et al. (2000) Science 288:113-116, and PCT Publication WO 01/01025, for example.

Figure 1D:
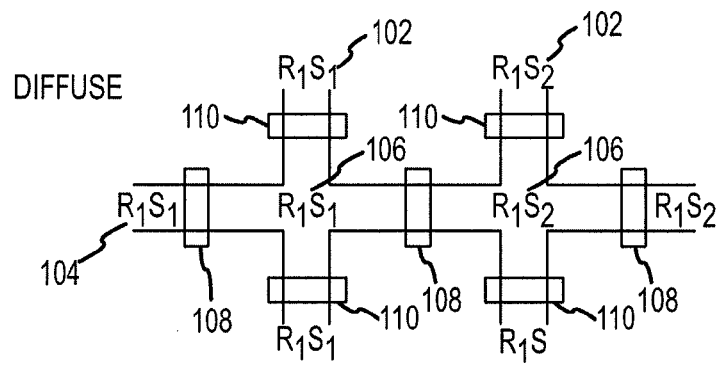
Figure 1E:
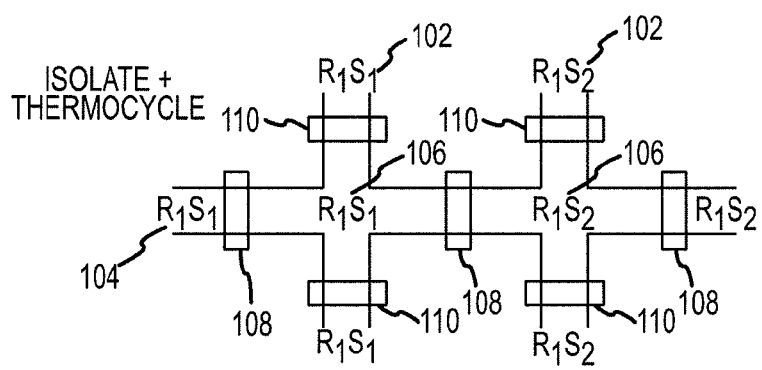

Once R1 has been introduced, row valves 108 are closed and column valves 102 opened (see FIG. 1C). This allows samples S1 and S2 to be introduced into vertical flow channels 102 and to flow through their respective flow channels. As the samples flow through the vertical flow channels 102, they expel R1 from the reaction chambers 106, thus leaving sample at reaction chambers 106. Then, as shown in FIG. 1D, row valves 108 are opened to allow S1 and S2 to diffuse and mix with R1. Thus, a mixture of sample and reactant (R1S1 and R1S2) is obtained in the region of each intersection or reaction chamber 106. After allowing a sufficient time for S1 and S2 to diffuse with R1, all row and column valves 108, 110 are closed to isolate S1 and S2 within the region of their respective reaction chambers 106 and to prevent intermixing of S1 and S2 (see FIG. 1E). The mixtures are then allowed to react and the reactions detected by monitoring the intersection 106 or the cross-shaped region that includes the intersection 106. For analyses requiring heating (e.g., thermocycling during amplification reactions), the device is placed on a heater and heated while the samples remain isolated.

Figure 1F:
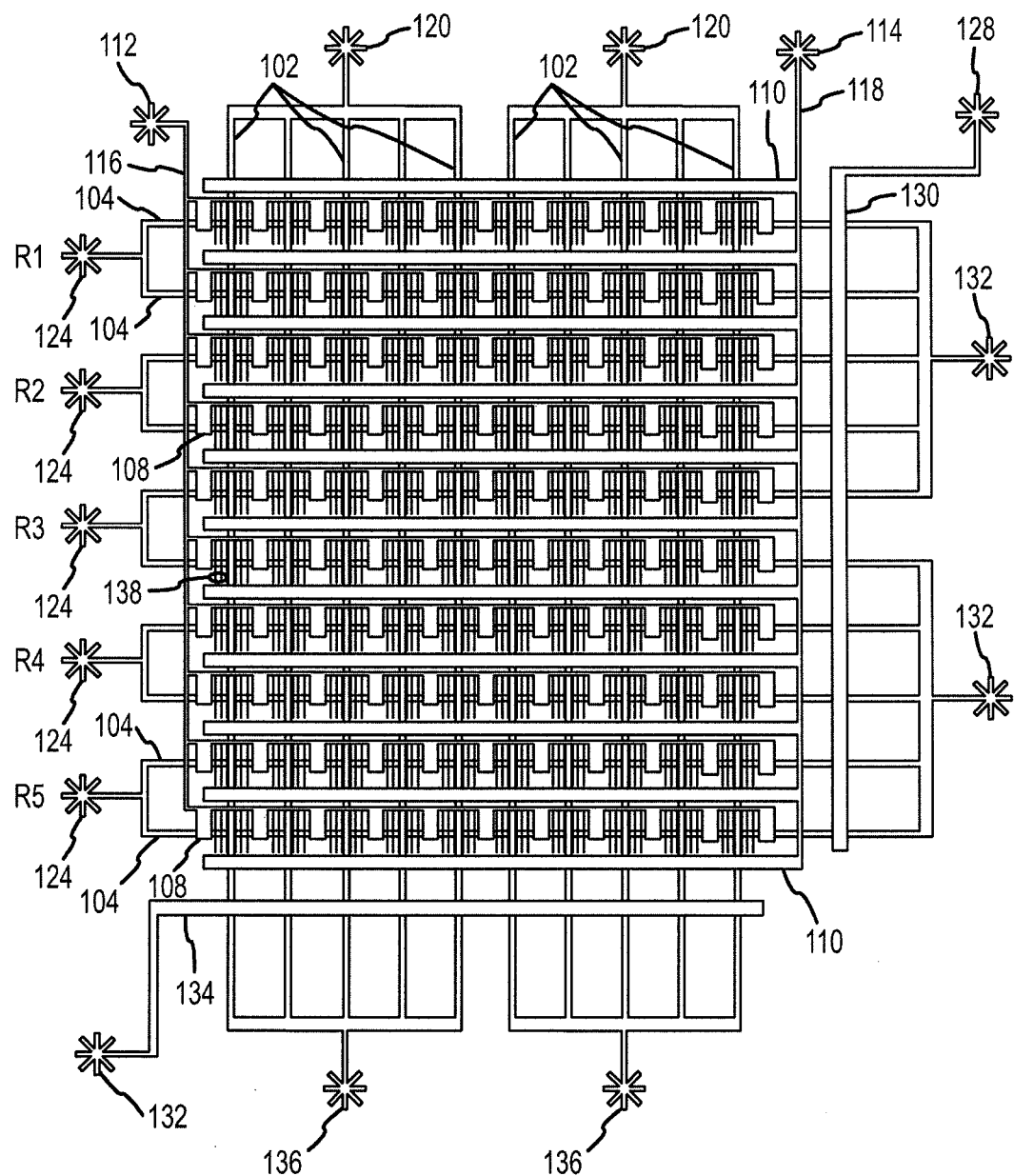
FIG. 1F is a schematic representation of another exemplary matrix design device that utilizes guard channels to reduce sample evaporation.

A modified version of the device shown in FIG. 1A is shown in FIG. 1F. The general structure bears many similarities with that depicted in FIG. 1A, and common elements in both figures share the same reference numbers. The device 150 illustrated in FIG. 1F differs in that pairs of horizontal flow channels 104 are joined to a common inlet 124. This essentially enables duplicate sets of reagents to be introduced into two adjacent flow channels with just a single injection into inlet 124. The use of a common inlet is further extended with respect to the vertical flow channels 102. In this particular example, each sample is introduced into five vertical flow channels 102 with a single injection into sample inlet 120. Thus, with this particular device, there are essentially ten replicate reactions for each particular combination of sample and reagent. Of course, the number of replicate reactions can be varied as desired by altering the number of vertical and/or horizontal flow channels 102, 104 that are joined to a common inlet 120, 124.

The device shown in FIG. 1F also includes a separate control channel inlet 128 that regulates control channel 130 that can be used to govern solution flow toward outlets 132 and another control channel inlet 132 that regulates control channel 134 that regulates solution flow to outlets 136. Additionally, device 150 incorporates guard channels 138. In this particular design, the guard channels 138 are formed as part of control channels 116. As indicated supra, the guard channels 138 are smaller than the row valves 108; consequently, the membranes of the guard channels 138 are not deflected into the underlying horizontal flow channels 104 such that solution flow is disrupted.

Finally, the design shown in FIG. 1F differs in that reaction does not occur in wells at the intersection of the horizontal and vertical flow lines, but in the intersection itself.

Blind Channel Designs

Devices utilizing a blind channel design have certain features. First, the devices include one or more flow channels from which one or more blind channels branch. As indicated above, the end region of such channels can serve as a reaction chamber. A valve formed by an overlaying flow channel can be actuated to isolate the reaction chamber at the end of the blind channel. The valves provide a mechanism for switchably isolating the reaction chambers.

Second, the flow channel network in communication with the blind channels is configured such that all or most of the reaction chambers can be filled with a single or a limited number of inlets (e.g., less than 5 or less than 10). The ability to fill a blind flow channel is made possible because the devices are made from elastomeric material. The elastomeric material is sufficiently porous such that air within the flow channels and blind channels can escape through these pores as solution is introduced into the channels. The lack of porosity of materials utilized in other microfluidic devices precludes use of the blind channel design because air in a blind channel has no way to escape as solution is injected.

A third characteristic is that one or more reagents are non-covalently deposited on a base layer of elastomer during manufacture (see infra for further details on the fabrication process) within the reaction chambers. The reagent(s) are non-covalently attached because the reagents are designed to become dissolved when sample is introduced into the reaction chamber. To maximize the number of analyses, a different reactant or set of reactants is deposited at each of the different reaction chambers.

Certain blind channel devices are designed such that the reaction chambers are arranged in the form of an array.

Thus, in those blind channel devices designed for conducting immunological reactions, for example, one or more of the reagents, such as antibodies, antigens, or blocking reagents may be deposited at each of the reaction chambers during manufacture of the device.

The reagents can be immobilized in a variety of ways. For example, in some instances one or more of the reagents are non-covalently deposited at the reaction chamber, whereas in other instances one or more of the reagents is covalently attached to the substrate at the reaction chamber. If covalently attached, the reagents can be linked to the substrate via a linker. A variety of linker types can be utilized such as photochemical/photolabile linkers, themolabile linkers, and linkers that can be cleaved enzymatically. Some linkers are bifunctional (i.e., the linker contains a functional group at each end that is reactive with groups located on the element to which the linker is to be attached); the functional groups at each end can be the same or different. Examples of suitable linkers that can be used in some assays include straight or branched-chain carbon linkers, heterocyclic linkers and peptide linkers. A variety of types of linkers are available from Pierce Chemical Company in Rockford, Ill. and are described in EPA 188,256; U.S. Pat. Nos. 4,671,958; 4,659,839; 4,414,148; 4,669,784; 4,680,338, 4,569,789 and 4,589,071, and by Eggenweiler, H. M, Pharmaceutical Agent Discovery Today 1998, 3, 552. NVOC (6 nitroveratryloxycarbonyl) linkers and other NVOC-related linkers are examples of suitable photochemical linkers (see, e.g., WO 90/15070 and WO 92/10092). Peptides that have protease cleavage sites are discussed, for example, in U.S. Pat. No. 5,382,513.

Exemplary Designs and Uses

Figure 2:
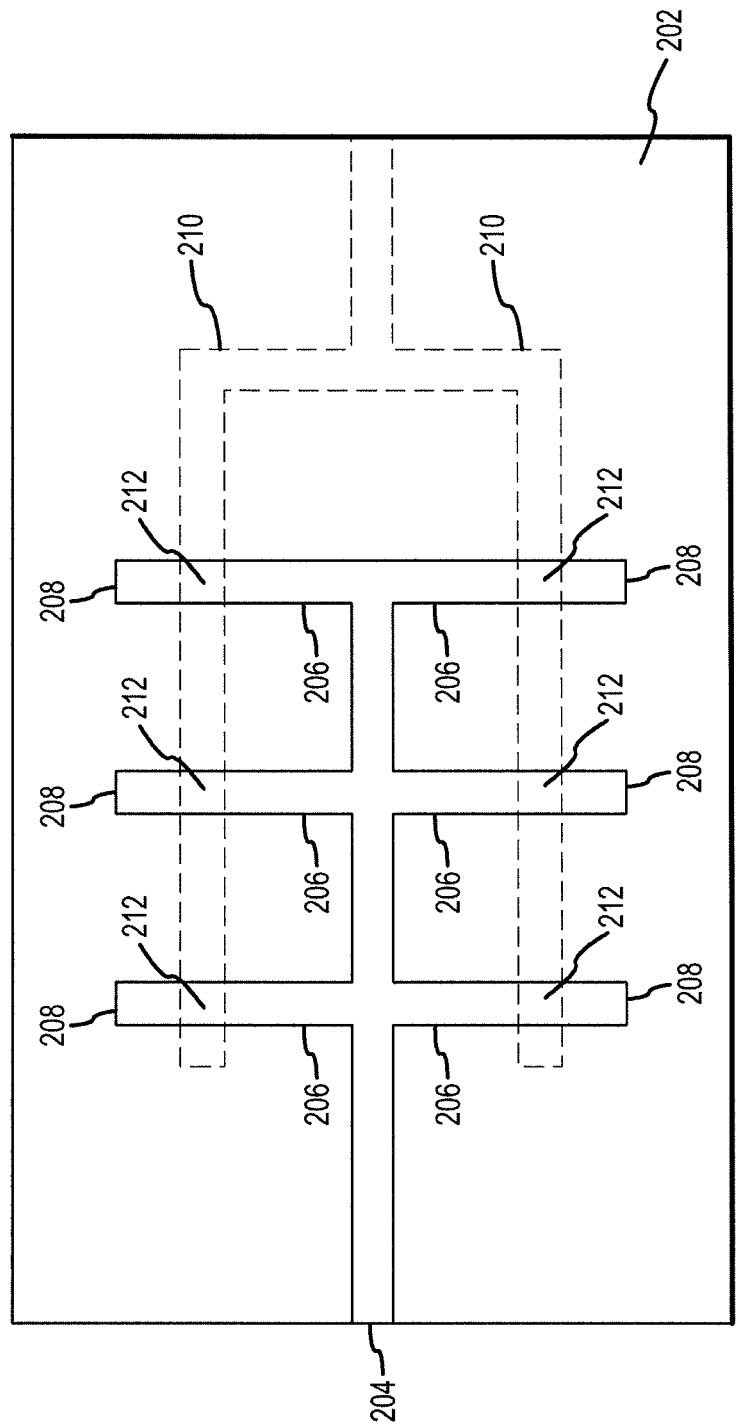
FIG. 2 is a plan view of an exemplary blind channel device.

FIG. 2 is a simplified plan view of one exemplary device utilizing the blind channel design. The device 200 includes a flow channel 204 and a set of branch flow channels 206 branching therefrom that are formed in an elastomeric substrate 202. Each branch flow channel 206 terminates in a reaction chamber 208, thereby forming an array of reaction chambers. Overlaying the branch flow channels 206 is a control channel 210 that is separated from the branch flow channels 206 by membranes 212. Actuation of control channel 210 causes membranes 212 to deflect into the branch flow channels 206 (i.e., to function as a valve), thus enabling each of the reaction chambers 208 to be isolated from the other reaction chambers.

Operation of such a device involves injecting a test sample into flow channel 204 with solution subsequently flowing into each of branch channels 206. Once the sample has filled each branch channel 206, control channel 210 is actuated to cause activation of valves/membranes 212 to deflect into branch channels 206, thereby sealing off each of reaction chambers 208. As the sample flows into and remains in reaction chambers 208, it dissolves reagents previously spotted at each of the reaction chambers 208. Once dissolved, the reagents can react with the sample. Valves 212 prevent the dissolved reagents at each reaction chamber 208 from intermixing by diffusion. Reaction between sample and reagents are then detected, typically within reaction chamber 208. Reactions can optionally be heated as described in the temperature control section infra.

Figure 3A:
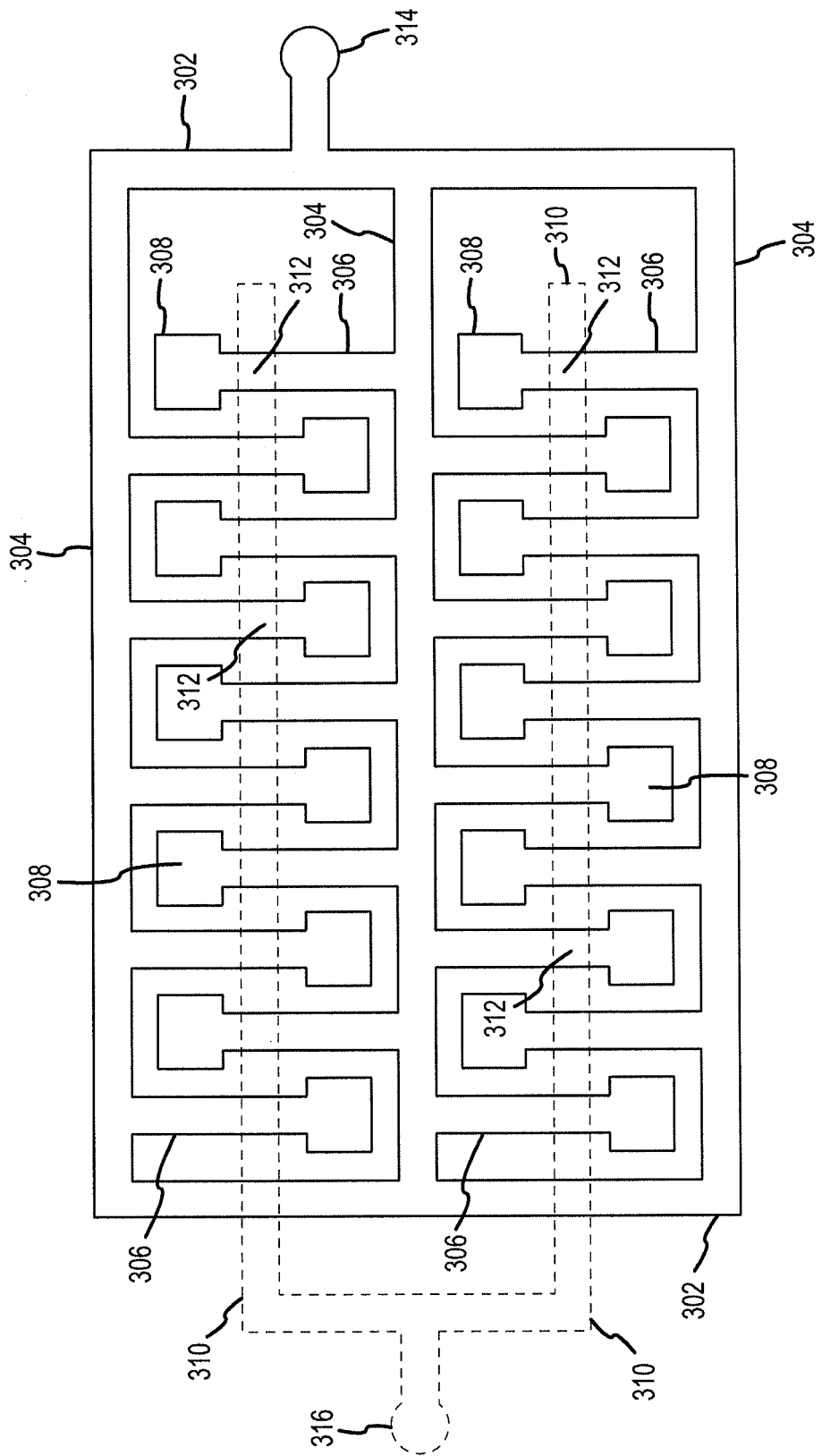
FIG. 3A is a plan view of another exemplary blind channel device.
Figure 3C:
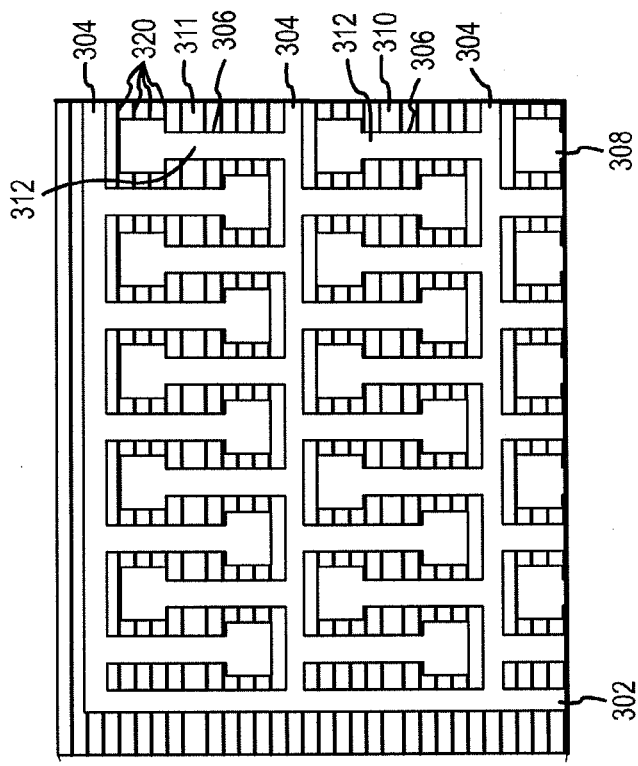
FIG. 3C is an enlarged view of a region of the device shown in FIG. 3B, and illustrates the orientation of the guard flow channels in this particular design.

FIG. 3A illustrates an example of a somewhat more complex blind flow channel design. In this particular design 300, each of a set of horizontal flow channels 304 are connected at their ends to two vertical flow channels 302. A plurality of branch flow channels 306 extend from each of the horizontal flow channels 304. The branch flow channels 304 in this particular design are interleaved such that the branch channel 306 attached to any given horizontal flow channel 304 is positioned between two branch channels 306 joined to an immediately adjacent horizontal flow channel 304, or positioned between a branch flow channel 306 joined to an immediately adjacent flow channel 304 and one of the vertical flow channels 302. As with the design depicted in FIG. 3A, each branch flow channel 306 terminates in a reaction chamber 308. Also consistent with the design shown in FIG. 3A, a control channel 310 overlays each of the branch channels and is separated from the underlying branch channel by membrane 312. The control channel is actuated at port 316. The vertical and horizontal flow channels 302, 304 are interconnected such that injection of sample into inlet 314 allows solution to flow throughout the horizontal and vertical flow channel network and ultimately into each of the reaction chambers 308 via the branch flow channels 306.

Hence, in operation, sample is injected into inlet to introduce solution into each of the reaction chambers. Once the reaction chambers are filled, valves/membranes are actuated to trap solution within the reaction chambers by pressurizing the control channels at port. Reagents previously deposited in the reaction chambers become resuspended within the reaction chambers, thereby allowing reaction between the deposited reagents and sample within each reaction chamber. Reactions within the reaction chambers are monitored by a detector. Again, reactions can optionally be controllably heated according to the methods set forth in the temperature control section below.

Figure 3B:
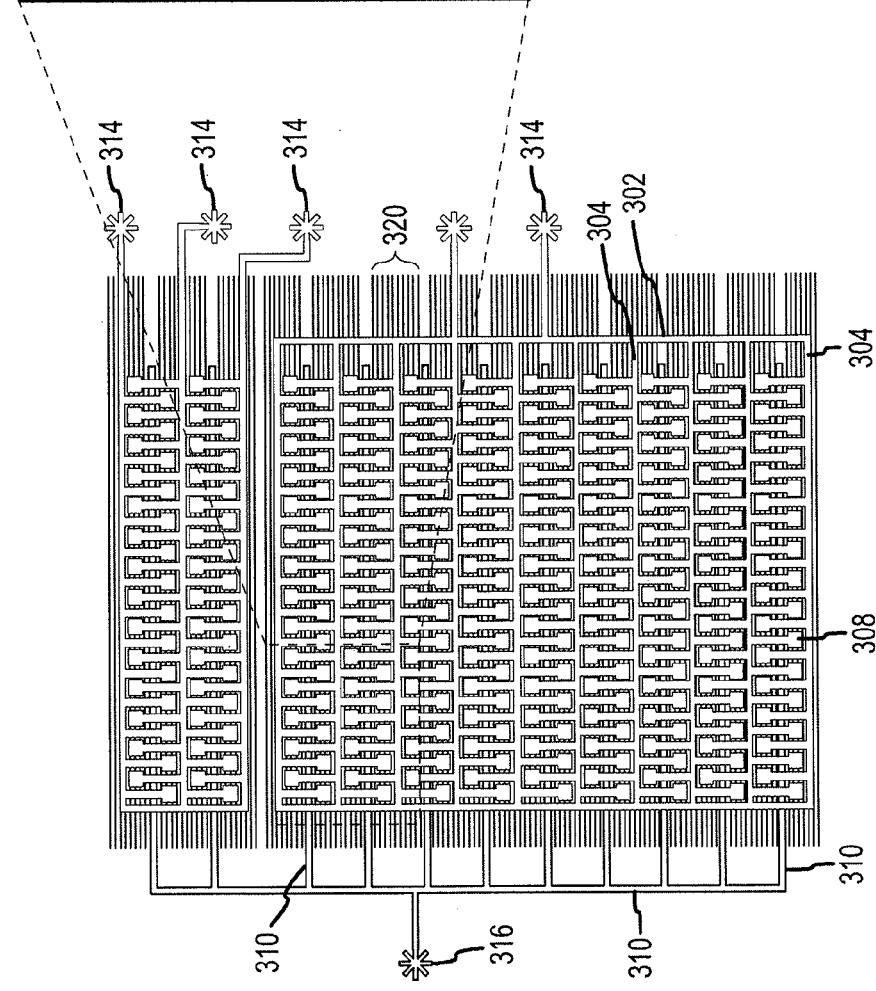
FIG. 3B is a schematic representation of a more complex blind channel device based upon the unit of the general design depicted in FIG. 3A.

An even more complicated version of the general design illustrated in FIG. 3A is shown in FIG. 3B. The device shown in FIG. 3B is one in which the unit organization of the horizontal and branch flow channels 302 shown in FIG. 3A is repeated multiple times. The device shown in FIG. 3B further illustrates the inclusion of guard channels 320 in those devices to be utilized in applications that involve heating (e.g., thermocycling). An exemplary orientation of the guard channels 320 with respect to the flow channels 304 and branch channels 306 is shown in the enlarged view depicted in FIG. 3C. The guard channels 320 overlay the branch flow channels 306 and reaction chambers 308. As discussed above, water is flowed through the guard channels 320 during heating of the device 300 to increase the local concentration of water in the device, thereby reducing evaporation of water from solution in the flow channels 306 and reaction chambers 308.

The features of blind channel devices discussed at the outset of this section minimizes the footprint of the device and enable a large number of reaction chambers to be formed on the device and for high densities to be obtained. For example, devices of this type having 2500 reaction chambers can readily be manufactured to fit on a standard microscope slides (25 mm×75 mm). The foregoing features also enable very high densities of reaction chambers to be obtained with devices utilizing the blind channel design. For example, densities of at least 50, 60, 70, 80, 90 or 100 reaction chambers/$cm^2$ or any integral density value therebetween can be readily obtained. However, certain devices have even higher densities ranging, for example, between 100 to 4000 reaction chambers/$cm^2$, or any integral density value therebetween. For instance, some devices have densities of at least 100, 150, 200, 250, 300, 400, 500, 600, 700, 800, 900 or 1000 sites/$cm^2$. Devices with very high densities of at least, 2000, 3000, or 4000 sites/$cm^2$ are also obtainable. Such high densities directly translate into a very large number of reaction chambers on the device. Devices utilizing the blind channel architecture typically have at least 10-100 reaction chambers, or any integral number of sites therebetween. More typically, the devices have at least 100-1,000 reaction chambers, or any integral number of sites therebetween. Higher density devices can have even more reaction chambers, such as at least 1,000-100,000 reaction chambers, or any integral number of sites therebetween. Thus, certain devices have at least 100; 500; 1,000; 2,000; 3,000; 4,000; 5,000; 6,000; 7,000; 8,000; 9,000; 10,000; 20,000; 30,000; 40,000; 50,000; or 100,000 reaction chambers depending upon the overall size of the device.

The large number of reaction chambers and densities that can be obtained is also a consequence of the ability to fabricate very small wells or cavities. For example, the cavities or wells typically have a volume of less than 50 mL; in other instances less than 40 nL, 30 nL, 20 nL or 10 nL; and in still other instances less than 5 nL or 1 nL. As a specific example, certain devices have wells that are 300 microns long, 300 microns wide and 10 microns deep.

The blind channel devices provided herein can utilize certain design features and methodologies discussed in PCT Applications PCT/US01/44549 (published as WO 02/43615) and PCT/US02/10875 (published as WO 02/082047), including, for example, strategies for filling dead-ended channels, liquid priming, pressurized outgas priming, as well as various strategies for displacing gas during the filling of microfluidic channels. Both of these PCT publications are incorporated herein by reference in their entirety for all purposes.

Hybrid Designs

Still other devices are hybrids of the matrix and blind fill designs. The design of devices of this type is similar to the blind channel device shown in FIG. 3A, except that each horizontal flow channel is connected to its own sample inlet port(s) and the horizontal flow channels are not interconnected via vertical flow channels. Consequently, sample introduced into any given horizontal flow channel fills only that horizontal flow channel and reaction chambers attached thereto. Whereas, in the blind flow channel device shown in FIG. 3A, sample can flow between the horizontal flow channels 304 via vertical flow channels 302.

Figure 4:
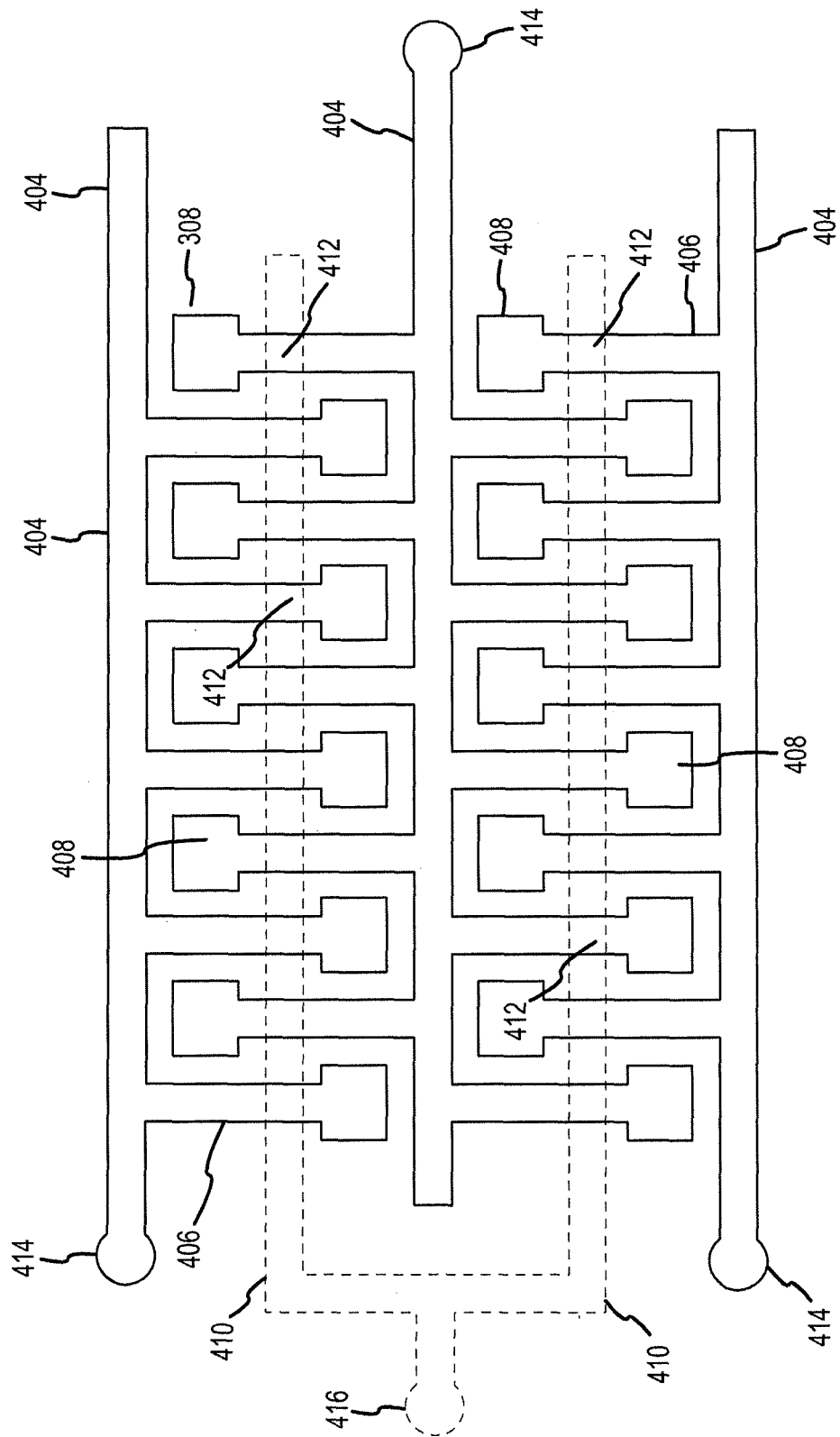
FIG. 4 is a plan view of a device utilizing the hybrid design.

An example of devices of this general device is shown in FIG. 4. Device 400 comprises a plurality of horizontal flow channels 404, each of which has a plurality of branch flow channels 406 extending from it and its own sample inlet 414. A control channel 410 overlays each of the branch flow channels 406 and membrane (valve) 412 separates the control channel 410 from the underlying branch flow channel 406. As with the blind flow channel design, actuation of the control channel at inlet 416 causes deflection of membranes 412 into the branch flow channels 406 and isolation of reaction chambers 408. In a variation of this design, each horizontal flow channel 404 can include an inlet 414 at each end, thus allowing sample to be introduced from both ends.

In some instances, reagents are deposited at the reaction chambers during manufacture of the device. This enables a large number of samples to be tested under a relatively large number of reaction conditions in a short period of time without requiring time-consuming additions of reagents as required with the matrix devices. Alternatively, reaction mixtures can be prepared prior to injection on the chip. Once the mixtures are injected, they can be analyzed or further treated (e.g., heated).

By injecting different samples into each of the horizontal flow channels, a large number of samples can be rapidly analyzed. Assuming reagents have been previously deposited at the reaction chambers, the presence of the same reagent at each reaction chamber associated with any given horizontal flow channel provides a facile way to conduct a number of replicate reactions with each sample. If instead, the reagent at the reaction chambers differ for any given flow channel, then each sample is essentially simultaneously exposed to a variety of different reaction conditions.

Thus, the devices provided herein are tailored for a variety of different types of investigations. If an investigation involves screening of a relatively large number of different samples under user controlled conditions (e.g., 100 samples against 100 user selected reagents), then the matrix devices provide a useful solution. If, however, the investigation involves analyzing one or a limited number of samples under a wide variety of reaction conditions (e.g., one sample against 10,000 reaction conditions), then the blind channel design is useful. Finally, if one wants to examine a relatively large number of samples against defined reaction conditions without having to inject reagents (e.g., 100 samples against 100 previously defined reagents), then the hybrid devices are useful.

Figure 14:
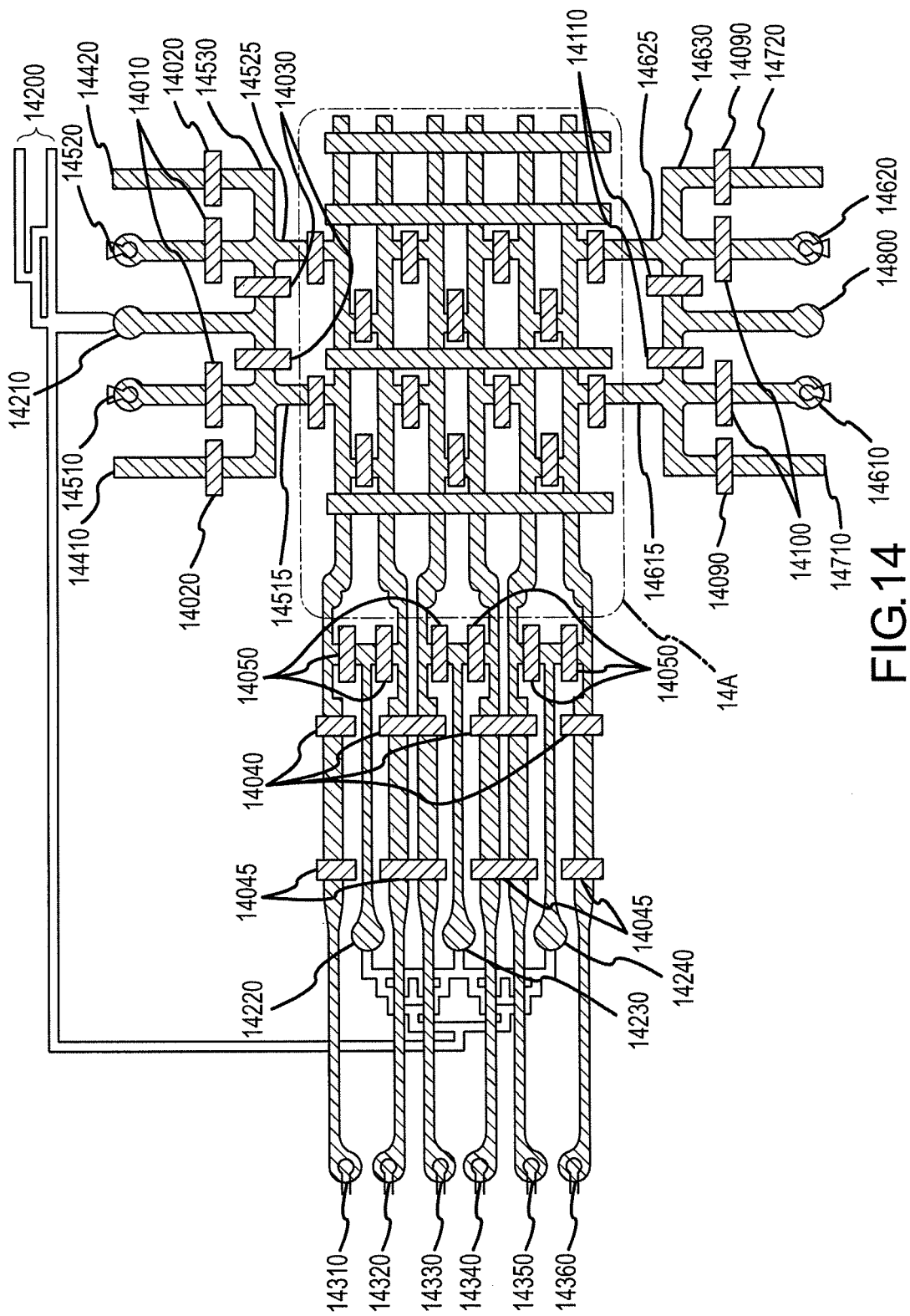
FIG. 14 is a diagram of a representative portion of a microfluidic chip showing the arrangement of flow channels and valves.

The following legend defines the elements of FIG. 14 and FIG. 14A.

Valves:
14010—First inlet valve array
14020—First outlet valve array
14030—First wash valve array
14040—Third inlet valve array
14050—Second wash valve array
14060—Matrix column isolation valve array 1
14070—Matrix column isolation valve array 2
14075—Matrix column isolation valve array 3
14080—Matrix outlet closure valve array
14090—Second outlet valve array
14100—Second inlet valve array
14110—Common valve array
14120—First pre-matrix valve array
14130—Matrix row isolation valve number 1
14131—Matrix row isolation valve number 2
14132—Matrix row isolation valve number 3
14133—Matrix row isolation valve number 4
14134—Matrix row isolation valve number 5
14135—Matrix row isolation valve number 6
14136—Matrix row isolation valve number 7
14137—Matrix row isolation valve number 8
14138—Matrix row isolation valve number 9
14139—Matrix row isolation valve number 10
14140—Second pre-matrix valve array Flow Channels:
14200—Common wash flow channel
14210—First inlet wash flow channel
14220—Third inlet wash flow channel number 1
14230—Third inlet wash flow channel number 2
14240—Third inlet wash flow channel number 3
14250—Matrix fluidic column 1
14255—Matrix fluidic column 2
14310—Sample matrix flow channel inlet number 1
14311—Sample matrix flow channel number 1
14312—Sample matrix flow channel outlet number 1
14320—Sample matrix flow channel inlet number 2
14321—Sample matrix flow channel number 2
14322—Sample matrix flow channel outlet number 2
14330—Sample matrix flow channel inlet number 3
14331—Sample matrix flow channel number 3
14332—Sample matrix flow channel outlet number 3
14340—Sample matrix flow channel inlet number 4
14341—Sample matrix flow channel number 4
14341—Sample matrix flow channel outlet number 4
14350—Sample matrix flow channel inlet number 5
14351—Sample matrix flow channel number 5
14352—Sample matrix flow channel outlet number 5

14360—Sample matrix flow channel inlet number 6
14361—Sample matrix flow channel number 6
14362—Sample matrix flow channel outlet number 6
14410—First outlet flow channel number 1
14420—First outlet flow channel number 2
14510—First inlet flow channel number 1
14515—First inlet matrix flow channel number 1
14520—First inlet flow channel number 2
14525—First inlet matrix flow channel number 2
14530—Common flow channel 1
14610—Second inlet flow channel number 1
14615—Second inlet matrix flow channel number 1
14620—Second inlet flow channel number 2
14625—Second inlet matrix flow channel number 2
14630—Common flow channel 2
14710—Second outlet flow channel number 1
14720—Second outlet flow channel number 2
14800—Common input flow channel
14805—Matrix interconnector flow channel 1
14810—Matrix interconnector flow channel 2
14815—Matrix interconnector flow channel 3
14820—Matrix interconnector flow channel 4
14825—Matrix interconnector flow channel 5
14830—Matrix interconnector flow channel 6
14835—Matrix interconnector flow channel 7
14840—Matrix interconnector flow channel 8
14845—Matrix interconnector flow channel 9
14850—Matrix interconnector flow channel 10
14970—Representative reaction chamber
14980—Matrix fluidic row 1
14981—Matrix fluidic row 2
14982—Matrix fluidic row 3
14983—Matrix fluidic row 4
14984—Matrix fluidic row 5
14985—Matrix fluidic row 6

FIG. 14 and FIG. 14A are schematic diagrams of a representative portion of a matrix device of the present invention. The representative portion of the device detailed in FIGS. 14 and 14A contains an addressable matrix of 12 reaction chambers defined by a plurality of sample flow channels and inlet flow channels that are associated with valves. The matrix row isolation valves can be closed together with the matrix column isolation valves to define discrete reaction chambers within the matrix (e.g. 14970). In this representative portion of a larger matrix device, the rows of the matrix are sample matrix flow channels numbers 1, 2, 3, 4, 5, 6, that are shown in FIG. 14A as 14311, 14321, 14331, 14341, 14351, and 14361, respectively that may flow directionally from inlet, through the matrix row, to the outlet. The columns of the matrix, in one embodiment, are directional. First inlet flow channel number 1 (14510) and first inlet matrix flow channel number 1 (14515) define the header of a first matrix column that flows, when appropriately configured and pressurized liquid is introduced into 14515 through 14510 and then through a matrix column when matrix column isolation valves 1 and 2 (14060 and 14070) are closed, second outlet valve array, 14090, is open, and matrix row isolation valves 14130, 14132, 14134, 14136, and 14138 are open. The flow in this condition is in the direction from the row defined by 14311 toward and through matrix row defined by 14361. Second inlet flow channel number 1 (14610) and second inlet matrix flow channel number 1 (14615) define the footer of a first matrix column that that flows upwards through the matrix row defined by 14361 and towards and through the matrix row defined by 14311 when valve states remain as described immediately above but 14090 is closed and first outlet valve array, 14020, is opened and pressurized liquid is introduced into 14615 through 14610. The structure and valve addressability define a multiplex immunoassay device. The ability of the matrix device to flush unused buffer, protein solutions and reagents out of the matrix and to switch flow directions when introducing antibody pairs enable the isolation of reaction chambers that perform sensitive immunoassays en mass with low sample volumes while reducing or, in some assays, essentially eliminating crosstalk between antibody pairs.

Many of the channels within the matrix device contain a deflectable membrane in one or more positions along the flow channel. The deflection of the membrane into the flow channel acts as a valve to seal off fluid or gas flow through the portion of the channel in which the membrane is deflected. The deflectable membrane may be actuated by different mechanisms and thus there may be different mechanisms of fluid flow control. One mechanism is through the pressurization of an adjacent control channel that shares a deflectable membrane portion with the fluid channel. The pressurization of the control channel causes the shared membrane to deflect into the flow channel. The pressurization of the control channel can be by gas or liquid pressure and the pressure source may arise externally through gas or liquid tubing that interfaces with the chip or though pressurization of channels in a frame or carrier that support the chip. The pressurization applied by the frame or carrier may be maintained by one or more pressure accumulators contained by the frame or carrier. Alternately, the source of gas or liquid pressure may be chemically, photochemically, or electrochemically generated and stored within the frame or carrier or within the chip itself. The deflectable membrane may also be electrostatically deflected by the application of a voltage potential between a deflectable membrane and a surface adjacent to the deflectable membrane such as the flow channel wall opposite the deflectable membrane. The materials which conduct the voltage potential within the chip to activate the electrostatic valve can be electrodes implanted within, or deposited upon, the elastomeric material forming at least a portion of the matrix device or they can be electrically conductive elastomeric materials forming a portion of the matrix device. The valves are actuated through control lines that either take the form of conductive traces or wires running along the surfaces or are embedded or formed within the matrix device or through control channels that run along the surfaces or are embedded or formed within the matrix device. In the case of control channels, gaseous or liquid pressure for the actuation of valves is selectively applied. For the purposes of this description, the term "actuation" has been used to describe the closure of a flow or control channel in response to a control signal. However, the term "actuate" or "actuation" applies equally to the use of normally closed valves that are held open in response to a control signal and are closed (actuated) in response to the removal of that signal whether it is an electrical or pressure-driven signal.

Sample flow channels 14311, 14321, 14331, 14341, 14351, and 14361 in FIG. 14A are microfluidic channels that run horizontally across the schematic diagram defining the rows of the matrix device. The sample flow channel channels and their respective inlet and outlet channels have a width and a height that define a cross sectional area. Flow channels 14515, 14805, 14815, 14825, 14835, 14845, and 14615 run vertically across the diagrammed matrix chip defining a first column of the matrix device. The input to the column is from 14510 and the outlet of the column is 14710 through 14615 and 14630. Flow channels 14525, 14810, 14820, 14830, 14840, 14850, and 14625 run vertically across the diagrammed matrix chip defining a second column of the matrix device. The input to the column is from 14520 and the outlet of the column is 14720 through 14612 and 14630. Vertical flow channels 14515, 14805, 14815, 14825, 14835, 14845, 14615, 14525, 14810, 14820, 14830, 14840, 14850, and 14625 have a width and a height that define a cross sectional area.

When referring to a "fluidic matrix," "fluidic columns," or "fluidic rows," the terms are meant to refer to the general properties of a variety of embodiments of a microfluidic chip contain the matrix architecture described herein. The terms refer to the essential bulk fluid properties and do not mean, for example, that when referring to a "fluidic column" that there is a single column-shaped structure with an inlet and an outlet through which fluid flows. The term "fluidic column" refers to all of the channels and pathways through which a fluid flows when traversing one side of a conceptual column to the other side.

The width of the flow channels can be from about 5 um to about 1000 um and, for larger width flow channels, can be about 100 um, at or between about 100 um and about 150 um, at or between about 150 um and 200 um, at or between about 200 um and 250 um, at or between about 250 um and about 300 um, at or between about 300 um and about 350 um, at or between about 350 um and about 400 um, at or between about 400 um and about 450 um, at or between about 450 um and about 500 um, at or between about 500 um and about 550 um, at or between about 550 um and 600 um, at or between about 600 um and about 650 um, at or between about 650 um and about 700 um, at or between about 700 um and about 750 um, at or between about 750 um and 800 um, at or between about 800 um and about 850 um, at or between about 850 um and about 900 um, at or between about 900 um and about 950 um, at or between 950 um and 1000 um. In many applications, a range of flow channel widths from about 75 um to about 125 um will be preferred. However, in certain instances, channel widths could exceed 1000 um. For narrower channels, the widths can be about 5 um or greater and about 100 um or smaller. Channel widths can be from about 10 um to about 75 um, from about 15 um to about 50 um, and from about 20 um to about 40 um. In some embodiments the channel width is about 5, 10, 15, 20, 25, 30, 35, 40, 45, 50, 55, 60, 65, 70, or 75 um. The height can be from about 5 um to about 100 um, from about 10 um to about 75 um, from about 15 um to about 50 um, and from about 20 to about 40 um. In some embodiments the channel height is about 5, 10, 15, 20, 25, 30, 35, 40, 45, 50, 55, 60, 65, 70, or 75 um. The cross sectional area can be from about 20 to about 13000 um2, from about 50 to about 10000 um2, from about 200 to about 8000 um2, from about 250 to about 5000 um2, from about 500 to about 3000 um2, and in many embodiments, it is preferred to be from about 1400 to about 1600 um2. In some embodiments the cross sectional area is about 500, 600, 700, 800, 900, 1000, 1100, 1200, 1300, 1400, 1500, 1600, 1700, 1800, 1900, or about 2000 um2. The shape of the cross section of the individual channels of the matrix devices of this invention can be the same or different and can take different shapes such as square, rectangular, other polygonal, circular, elliptical, semicircular, semielliptical, etc. The cross sectional shapes and areas can vary within the same channel and can be prepared by fabrication techniques described earlier and known in the art. Square or rectangular channel geometries are generally disfavored at valve sites do to the difficulty or even inability to be completed closing a valve at a square or rectangular channel.

Each sample matrix flow channel has a corresponding sample matrix flow channel inlet and a corresponding sample matrix flow channel outlet. In the embodiment represented in FIGS. 14 and 14A, matrix column isolation valve arrays act on portions of the sample matrix flow channels through deflectable membranes to fluidically isolate portions of the sample matrix flow channels. For the sake of clarity in FIG. 14A, 14060 defines the fluidic juncture between sample matrix flow channel inlet and sample matrix flow channel just prior to the sample matrix flow channel and isolation valve, 14075, defines the fluidic juncture between sample matrix flow channel and sample matrix flow channel outlet just subsequent to the sample matrix flow channel. So, for this embodiment, the matrix column isolation valve arrays are acting on the sample matrix flow channels. For example in FIG. 14A, sample matrix flow channel inlet number 1 (14310) joins in switchable fluidic communication with sample matrix flow channel number 1 (14311) just prior to matrix column isolation valve array 1 (14060) and sample matrix flow channel outlet number 1 (14312) joins in switchable fluidic communication with 14311 just subsequent to matrix column isolation valve array number 3 (14075). The sample matrix flow channels substantially define the reaction surfaces for the immunoassays. The matrix column isolation valves may operate as a member of a valve array or under independent control.

The individual segments of the sample matrix flow channels that make up the reaction chambers of the matrix columns are defined by one or greater numbers of matrix column isolation valve arrays (or independently actuated column isolation valves) that are interior to the bounding inlet and outlet matrix column isolation valves (or valve arrays). It is preferred that the sample matrix flow channel segments defining the reaction chambers upon closure of the matrix column isolation valves are of equal length to one another so that they may be of equal volume. If the matrix device is designed so that the segments are of unequal lengths, then it is preferred that the lengths are known so that the reaction chamber volumes are known. In the example in FIG. 14, matrix column isolation valve array 2 (14070) bisects the sample matrix flow channels bounded by 14060 and 14075 to define columns of reaction chambers of equal size and volume.

Common wash flow channel (14200) fluidically communicates with first inlet wash flow channel (14210), third inlet wash flow channel number 1 (14220), third inlet wash flow channel number 2 (14230), and third inlet wash flow channel number 3 (14240). 14210 is in switchable fluidic communication with first inlet flow channel number 1 (14510), first inlet flow channel number 2 (14520), first outlet flow channel number 1 (14410), and first outlet flow channel number 2 (14420) via common flow channel 1 (14530).

First inlet valve array (14010) represents deflectable membrane portions of flow channels 14510 and 14520 such that, upon actuation, 14010, isolates 14510 and 14520 from fluidic communication. First outlet valve array (14020) represents deflectable membrane portions of 14410 and 14420 such that, upon actuation, 14020, isolates 14410 and 14420 from fluidic communication with other diagrammed flow channels. First wash valve array, 14030, represents deflectable membrane portions of 14530 in a first segment such that, upon actuation, 14030 fluidically isolates 14210 from other diagrammed flow channels.

First inlet matrix flow channel number 1 (14515) has a first end and a second end. The first end of 14515 is in fluidic communication with 14530 at a portion of 14530 that is fluidically isolatable from the outlet side of 14410 by closure of 14020, the inlet side of 14510 by closure of 14010, and the inlet side of 14210 closure of 14030. First inlet matrix flow channel number 2 (14525) has a first end and a second end. The first end of 14525 is in fluidic communication with 14530 at a portion that is fluidically isolatable from, the outlet side of 14420 by the closure of 14010, the inlet side of 14520 by the closure of 14010, and the inlet side of 14210 by closure of 14030.

The second end of 14515 and the second end of 14525 are in switchable fluidic communication with segments of sample matrix flow channel number 1 (14311). Matrix column isolation valve array 2 (14070) represents a set of deflectable membrane portions of each of the individual flow channels that make up the rows of the matrix. One valve portion of 14070, when actuated, acts to isolate the fluidic communication of 14515 and 14525 through 14311.

Sample matrix flow channel number 1 (14311) has a first end that is in switchable fluidic communication with sample matrix flow channel inlet number 1 (14310) and a second end that is in switchable fluidic communication with sample matrix flow channel outlet number 1 (14312). Likewise, sample matrix flow channel number 2 (14321) has a first end that is in switchable fluidic communication with sample matrix flow channel inlet number 2 (14320) and a second end that is in switchable fluidic communication with sample matrix flow channel outlet number 2 (14322), sample matrix flow channel number 3 (14331) has a first end that is in switchable fluidic communication with sample matrix flow channel inlet number 3 (14330) and a second end that is in switchable fluidic communication with sample matrix flow channel outlet number 3 (14332), sample matrix flow channel number 4 (14341) has a first end that is in switchable fluidic communication with sample matrix flow channel inlet number 4 (14340) and a second end that is in switchable fluidic communication with sample matrix flow channel outlet number 4 (14342), sample matrix flow channel number 5 (14351) has a first end that is in switchable fluidic communication with sample matrix flow channel inlet number 5 (14350) and a second end that is in switchable fluidic communication with sample matrix flow channel outlet number 5 (14352), and sample matrix flow channel number 6 (14361) has a first end that is in switchable fluidic communication with sample matrix flow channel inlet number 6 (14360) and a second end that is in switchable fluidic communication with sample matrix flow channel outlet number 6 (14362). In this embodiment, these structures define flow channels through the rows of the matrix device. The sample matrix flow channel outlets may also have individual deflectable membrane valves that can be configured to operate in a valve array. Matrix outlet closure valve array (14080) provides a valve system to close off the flow through the individual sample matrix flow channel outlets. The optional use of 14080 can enable dilation pumping (also know as volumetric capacitive pumping) in the elastomeric channels of the matrix devices of the present invention.

In this example, flow channels 14311, 14321, 14331, 14341, 14351, and 14361 are in switchable fluidic communication with each other through two sets of matrix interconnector flow channels that interact with the matrix column isolation valves to define the fluidic columns of the matrix. For example, first inlet flow channels, 14510 and 14520, are in switchable fluidic communication with sample matrix flow channel, 14311, through first inlet matrix flow channels, 14515 and 14525. Sample matrix flow channel, 14311, is in switchable fluidic communication with sample matrix flow channel, 14321, through matrix interconnector flow channels 1 and 2 (14805 and 14810). Sample matrix flow channel, 14321, is in switchable fluidic communication with sample matrix flow channel, 14331, through matrix interconnector flow channels 3 and 4 (14815 and 14820). Sample matrix flow channel, 14331, is in switchable fluidic communication with sample matrix flow channel, 14341, through matrix interconnector flow channels 5 and 6 (14825 and 14830). Sample matrix flow channel, 14341, is in switchable fluidic communication with sample matrix flow channel, 14351, through matrix interconnector flow channels 7 and 8 (14835 and 14840). Sample matrix flow channel, 14351, is in switchable fluidic communication with sample matrix flow channel, 14361, through matrix interconnector flow channels 9 and 10 (14845 and 14850). Each matrix interconnector flow channel has a corresponding deflectable membrane matrix row isolation valve that, when actuated, will fluidically isolate the pathway between adjacent sample matrix flow channels through the matrix interconnector channel.

The matrix interconnector flow channels and their respective matrix row isolation valves are listed below in Table 1. The matrix row isolation valves maybe configured to be independently actuated or they may be actuated as a valve array. It is also permitted that valve structures defined in this specification that are described as a valve array may have each valve that is member of the array under independent control. When matrix row isolation valves 14130 through 14039, first pre-matrix valve array, 14120, second pre-matrix valve array, 14140, and matrix column isolation valve arrays 14060, 14070, and 14075 are closed, two columns of six rows of reaction chambers are isolated and defined as exemplified by column 1, row 1, reaction chamber, 14970.

The volume of the reaction chambers should be carefully designed to balance several factors. There should be sufficient interior surface area defining the reaction chamber volume such that sufficient immunoreactive reagent can be present to provide the required assay sensitivity. The reaction chamber volume should be sufficiently small so that the assay is parsimonious with limited or valuable samples. The diffusional distance between the primary capture antibody anchored or deposited within the reaction chamber and the antigen within the sample stream flowing through the sample matrix flow channels must be short enough to provide a high probability of binding during the sample's traverse through the reaction chamber. The surface area of the reaction chamber, and thus the detection reagent quantity must also allow for a dynamic range sufficient to fulfill the purpose of the assay while maintaining required assay sensitivity. When measuring an optical signal by confocal microscopy, appropriate reaction chamber geometry allows the reading of signal from reagents anchored on opposite walls of the reaction chamber while remaining simultaneously detectable within the depth of field of the confocal imaging microscope. For that purpose, it is preferred that the imaged walls of the reaction chamber are parallel and spaced less than about 800 um apart, about 700 um or less apart, about 600 um or less apart, about 500 um or less apart, about 400 um or less apart, about 300 um or less apart. Smaller spacing of about 200 um, about 100 um, about 90 um, about 80 um, about 70 um, about 60 um, about 50 um, about 40 um, about 30 um, about 25, about 22, about 20, about 18, about 16, about 15, about 14, about 13, about 12, about 11, about 10, about 9, about 8, about 7, about 6, about 5 um or about 4 um are possible. Smaller reaction chamber volumes afford higher chip densities and yield increased economies of scale in cost per data point and also increase sample throughput rates per chip per unit of time. In one embodiment it is possible to complete the sample and reagent loading, and conduct the immunological reactions of up to 432 individual reaction chambers on a single matrix device in less than about 7 hours, preferably about 6 hours or less, more preferably about 5 hours or less, more preferably about 4 hours or less, more preferably about 3 hours or less. In another embodiment it is possible to complete the sample and reagent loading, and conduct the immunological reactions of up to 864 individual reaction chambers on a single matrix device in less than about 7 hours, preferably about 6 hours or less, more preferably about 5 hours or less, more preferably about 4 hours or less, more preferably about 3 hours or less. In another embodiment it is possible to complete the sample and reagent loading, and conduct the immunological reactions of 1296 individual reaction chambers on a single matrix device in less than about 7 hours, preferably about 6 hours or less, more preferably about 5 hours or less, more preferably about 4 hours or less, more preferably about 3 hours or less. In another embodiment it is possible to complete the sample and reagent loading, and conduct the immunological reactions of 2592 individual reaction chambers on a single matrix device in less than about 7 hours, preferably about 6 hours or less, more preferably about 5 hours or less, more preferably about 4 hours or less, more preferably about 3 hours or less. In another embodiment it is possible to complete the sample and reagent loading, and conduct the immunological reactions of 4608 individual reaction chambers on a single matrix device in less than about 7 hours, preferably about 6 hours or less, more preferably about 5 hours or less, more preferably about 4 hours or less, more preferably about 3 hours or less. In another embodiment it is possible to complete the sample and reagent loading, and conduct the immunological reactions of 9216 individual reaction chambers on a single matrix device in less than about 7 hours, preferably about 6 hours or less, more preferably about 5 hours or less, more preferably about 4 hours or less, more preferably about 3 hours or less. A matrixed assay device of the present invention may contain few large reaction chambers such as 4, 6, 8, 10, 12, 14, 16, 28, 32, 48, or 56. Or may have higher densities such as 128, 256, 432, 512, 864, 1024, 1296, 2592, 4608, 9216, or even integers in between.

The volume of the individual reaction chamber is generally between about 0.01 nL and about 10 nL, preferably between about 0.05 nL and about 8 nL, more preferably between about 0.05 and about 6 nL, more preferably between about 0.05 nL and about 5 nL, more preferably between about 0.05 and 4 nL, more preferably between about 0.05 and about 3 nL, more preferably between about 0.05 and about 2 nL. In some embodiments, the individual reaction chamber volume is less than about 2 nL. In other embodiments, the individual reaction chamber volume is about 1.50 nL or less. In a further embodiment, the individual reaction chamber volume is about 1.25 nL or less. In an additional embodiment, the individual reaction chamber volume is about 1.0 nL or less. In an additional preferred embodiments, the individual reaction chamber volume is about 0.6 nL or less. In a further preferred embodiment, the individual reaction chamber volume is about 0.5 nL or less. In an alternate embodiment, the individual reaction chamber volume is about 0.25 nL or less.

TABLE 1

Interconnector flow channel and row isolation valve correlation.

| Matrix Interconnector Flow Channel | Matrix Row Isolation Valve |
| --- | --- |
| 14805 | 14130 |
| 14810 | 14131 |
| 14815 | 14132 |
| 14820 | 14133 |
| 14825 | 14134 |
| 14830 | 14135 |
| 14835 | 14136 |
| 14840 | 14137 |
| 14845 | 14138 |
| 14850 | 14139 |

In the embodiment of FIG. 14, the bottom row of the matrix, sample matrix flow channel 6, 14361, is in switchable fluidic communication with common flow channel 2 (14630) through second inlet matrix flow channel number 1 (14615) and second inlet matrix flow channel number 2 (14625). 14615 and 14625 contain deflectable membrane portions of second pre-matrix valve array (14140) that, upon actuation, fluidically isolates 14361 from 14630 and thus 14710, 14610, 14110, 14620, and 14720. This series of channels and valves is functionally equivalent to the interconnected structures of 14410, 14510, 14210, 14520, 14420, 14530, 14515, and 14525 described above. The present system is a second set of switchable inlet and outlet ports for the matrix columns. The spatial relationships of the flow channels and their associated valves may vary as will the routings of the channels based on the chip architecture. What remains constant is the arrangement of inlets, outlets, and valves that permit full matrix washing and bidirectional flow through the columns of the matrix so that low cross reactivity between antibody pairs and high sensitivity are obtained.

Common wash flow channel, 14200, is in fluid communication with sample matrix flow channel inlets, 14310 and 14320 through third inlet wash flow channel number 1 (14220). 14200 is in fluid communication with sample matrix flow channel inlets 14330 and 14340 through third inlet wash flow channel number 2 (14230). 14200 is in fluid communication with sample matrix flow channel inlets 14350, and 14360 through third inlet wash flow channel number 3 (14240). The use of three separate third inlet wash flow channels in this embodiment is a design choice that is determined, in part, by the volume of wash solution that is needed to quickly flush the fluid matrix. The use of fewer than three, such as one, or greater than three third inlet wash flow channels would be acceptable in the design of the matrix device as channel routing and wash flow channel cross sectional areas permit. Second wash valve array, 14050, allows closure of 14220, 14230, and 14240 during the introduction of samples to the matrix through sample matrix flow channel inlets, 14310, 14320, 14330, 14340, 14350, and 14360.

Third inlet valve array 1, 14040, and third inlet valve array 2, 14045, each represent a set valves acting through a deflectable membrane portion of each of the individual sample matrix flow channel inlets. The third inlet valve arrays (either configured as valve arrays or as independently actuated valves) act to isolate the sample matrix flow channel inlet, when actuated, from the rest of the microfluidic matrix device. 14040 and 14045 may be spaced along the sample matrix flow channel inlets so as to define a sample inlet segment on each individual sample matrix flow channel inlet and, when properly utilized in concert with such sample inlet segments, define a dilation pump for pumping sample in precisely reproducible volumes at low flow rates. The volume of the sample inlet segment defined by 14040 and 14045, when cycled and pressurized, determines the stroke volume for each cycle of the dilation pump.

Dilation pumping (also know as volumetric capacitive pumping) is a method of operating a properly configured integrated fluidic circuit (chip) to obtain precise, low rate, low volume pumping through all configured elements of a microfluidic circuit. Dilation pumping is unique to microfluidic circuits that utilize channels that have one or more channel walls formed from an elastomeric material. As an example, the flow across the sample matrix rows in the embodiment in FIG. 14 and FIG. 14A is considered with volumetric capacitive pumping. For this example, valve arrays 14050, 14140, and 14120 are actuated to the closed position. Valves 14130, 14131, 14132, 14133, 14134, 14135, 14136, 14137, 14138, and 14139 are also closed. Valve arrays 14060, 14070, 14075, and 14080 remain open for this illustration. Pumping proceeds by the closure of valve array 14040 and the opening of valve array 14045. Sample matrix flow channel inlets 14310, 14320, 14330, 14340, 14350, and 14360 are pressurized to introduce their respective sample solutions. The pressurization of microfluidic channels with at least one channel wall formed from an elastomeric material results in expansion of the elastomeric walks) outward from the channel with a resulting increase in channel volume that is proportional to the fluidic pressure (or gaseous pressure in alternate embodiments) within the channel, the elastic properties of the elastomeric channel wall material such as Young's modulus, and the length and cross sectional area of the channel. The channels are allowed to pressurize and then valve array 14040 is closed. Following closure of 14040, 14045 is opened. The pumped volume through the sample matrix flow channel inlets and into the sample matrix flow channels of the matrix is equal to the expanded volume of the channel segment bounded by 14040 and 14045 when under pressure minus the native volume of the channel segment when pressure is released and the expanded elastomeric channel wall(s) is allow to relax. Dilation pumping is continued through repetitive cycles of closing 14040, pressurizing the channel prior to 14040, closing 14040, and opening 14040. In this manner, continuous or discontinuous low volume pumping may be accomplished at precisely controlled flow rates.

Dilation pumping may be performed through any channel having a series of valves. As another example, dilation pumping down the columns of the matrix between valve arrays 14010 and 14190 is described. Valve arrays 14020, 14030, 14060, 14070, 14075, 14100, and 14110 are closed. Valve array 14010 is opened.

Valve array 14090 is closed and first inlet flow channel number 1 (14510) and first inlet flow channel number 2 (14520) are pressurized with their respective solutions containing primary antibody. Array 14010 is closed and then 14090 is opened allowing the expansion volume of the channels bounded by these two channel arrays to be pumped down the columns of the matrix. This sequence is repeated as necessary to deposit the appropriate primary antibody into the reaction chambers in the matrix columns.

Example 1

Operation of the Matrix Device

Control Sequence for the Matrix Device Shown in FIG. 14 and FIG. 14A.

Binding protein: Valves 14010, 14030, 14040, 14050, 14060, 14070, 14075, 14090, and 14100 are closed. The other valve structures are opened or remain open. Binding protein, in a buffer solution, is introduced under pressure into the matrix through common input flow channel, 14800. The binding protein binds to the matrix flow channel walls that the binding protein containing buffer solution contacts.

Carrier block: Valves 14010, 14020, 14030, 14060, 14070, 14075, 14110, 14120, 14130, 14131, 14132, 14133, 14134, 14135, 14136, 14137, 14138, 14139, and 14140 are closed. The other valve structures are opened or remain open. Blocking protein, in a buffer solution, is introduced under pressure into the matrix through common wash flow channel, 14200. The blocking protein binds to and protects flow channel walls where antibody bonding is not desired.

Wash: Valves 14010, 14020, 14050, 14060, 14070, 14075, 14100, and 14110 are closed. The other valve structures are opened or remain open. Wash solution is introduced under pressure into the matrix through common wash flow channel, 14200. The wash solution removes residual binding protein and blocking carrier in the matrix.

Primary antibody: Valves 14020, 14030, 14060, 14070, 14075, 14100, and 14110 are closed. The other valve structures are opened or remain open. The desired primary antibodies for each particular column of the matrix are introduced under pressure into their respective matrix columns through first inlet flow channel number 1 (14510) and first inlet flow channel number 2 (14520). The desired antibodies bind to the binding protein coated on the walls of the channels which were prepped in step 1 and through which the antibodies are now pumped.

Second wash: Valves 14010, 14020, 14050, 14060, 14070, 14075, 14100, and 14110 are closed. The other valve structures are opened or remain open. Wash solution is introduced under pressure into the matrix through common wash flow channel, 14200. The wash solution removes residual primary antibody solution from the matrix.

Sample antigen introduction: Valves 14010, 14020, 14100, 14110, 14120, 14130, 14131, 14132, 14133, 14134, 14135, 14136, 14137, 14138, 14139, 14140, and 14150 are closed. The other valve structures are opened or remain open. The individual samples for which the concentration of antigen is to be determined, are introduced under pressure into their respective matrix rows through 14310, 14320, 14330, 14340, 14350, and 14360. Sample antigens are captured by the appropriate antibodies previously deposited in step 4.

Third wash: Valves 14010, 14020, 14030, 14040, 14090, 14110, 14120, 14130, 14131, 14132, 14133, 14134, 14135, 14136, 14137, 14138, 14139, and 14140 are closed. Wash solution is introduced under pressure into the matrix through common wash flow channel, 14200. The wash solution removes residual sample solution components from the matrix.

Secondary antibody: Valves 14010, 14030, 14040, 14060, 14075, 14075, 14090, and 14110 are closed. The other valve structures are opened or remain open. The desired secondary antibodies for each particular column of the matrix are introduced under pressure into their respective matrix columns through second inlet flow channel number 1 (14610) and second inlet flow channel number 2 (14620). The secondary antibodies bind to the appropriate exposed epitope on the sample antigens captures by the primary antibodies.

Fourth wash: Valves 14010, 14020, 14050, 14060, 14070, 14075, 14100, and 14110 are closed. The other valve structures are opened or remain open. Wash solution is introduced under pressure into the matrix through common wash flow channel, 14200. The wash solution removes residual secondary antibody solution from the matrix. If a FLISA is being performed and the fluorescent label is attached to the secondary antibody, the matrix chip is read at this point and the data are collected. If an ELISA is being performed, the assay continues with step 10.

Enzyme introduction and binding: Valves 14010, 14030, 14040, 14050, 14060, 14070, 14075, 14090, and 14100 are closed. The other valve structures are opened or remain open. Enzyme, in a buffer solution, is introduced under pressure into the matrix through common input flow channel, 14800. The enzyme binds to linkers on the secondary antibodies in the matrix to complete the detection message generation system.

Fifth wash: Valves 14010, 14020, 14050, 14060, 14070, 14075, 14100, and 14110 are closed. The other valve structures are opened or remain open. Wash solution is introduced under pressure into the matrix through common wash flow channel, 14200. The wash solution removes residual, unlinked enzyme from the matrix.

Enzyme substrate: Valves 14010, 14030, 14040, 14050, 14060, 14070, 14075, 14090, and 14100 are closed. The other valve structures are opened or remain open. Enzyme substrate, in a buffer solution, is introduced under pressure into the matrix through common input flow channel, 14800. The substrate reacts under catalysis by the linked enzyme to generate a detectable entity whose concentration is proportional to the quantity of antigen captured by the primary antibodies. The detectable entity is retained in the reaction chamber through binding to tyrosine, for example.

Sixth and final wash: Valves 14010, 14020, 14050, 14060, 14070, 14075, 14100, and 14110 are closed. The other valve structures are opened or remain open. Wash solution is introduced under pressure into the matrix through common wash flow channel, 14200. The wash solution removes residual, unreacted and unbound substrate from the matrix. The matrix chip is read at this point and the data are collected.

It is seen through this example, that serpentine flow is used in both directions through the fluidic columns of the fluidic matrix. Though the configurations used to achieve this type of flow may vary, the tortuous flow of the serpentine pattern is advantageous in flushing out the channels in the fluidic columns during wash steps. This flushing technique, when coupled with the opposing flow directions used to introduce primary and secondary antibodies into the reaction channels of the fluidic matrix, significantly reduce antibody crosstalk over non-serpentine flow and the use of common flow channels for both antibodies of the antibody pairs. Use of the structures and methods of the invention can reduce antibody crosstalk by about 30% up to eliminating crosstalk altogether. Reductions of about 30%, about 35%, about 40%, about 45%, about 50%, about 55%, about 60%, about 65%, about 70%, about 75%, about 80%, about 85%, about 90%, about 95%, and essentially complete elimination can be achieved depending on the particular immunoassay and the antibody pairs utilized.

While flow across a row of the fluidic matrix cannot occur while the matrix is configured for matrix column flow, the individual rows may be independently controlled. When the matrix is configured for column flow, the individual columns of the fluidic matrix may be independently controlled.

In defining an operational matrix, each sample row should be capable of being fluidically isolated from an adjacent row or rows. The exception to this rule occurs when an adjacent row is used for a duplicate sample analysis and isolation is unnecessary. Likewise, each column of the matrix should be capable of being fluidically isolated from an adjacent column. The exception to this rule occurs, for example, when duplicate analyses are to be performed in adjacent columns.

Immunoassays

Detection of analytes in limited supply requires a highly sensitive assay system. Immunological assays have proven to be of great value for detection and quantification of numerous analytes in liquid samples. Because the results of immunological and other specific binding reactions are frequently not directly observable, various techniques have been devised for their indirect observation. Such techniques involve labeling of one of the members of the specific binding pair with a radioisotope, chromophore, fluorophore or enzyme label. Radiolabels, chromophores and fluorophores may be detected by the use of radiation detectors, spectrophotometers and fluorimeters. Where members of a specific binding pair are tagged with an enzyme label, their presence may be detected by the enzymatic activation of a reaction system wherein a compound such as a dyestuff, is activated to produce a detectable signal. Such procedures are described in a number of articles and texts, an example of which is Reviews on Immunoassay Technology, Ed. S. B. Pal, Pub. Chapman and Hall, 1988.

There are many types of immunoassays known in the art that can be adapted for use in the microfluidic chip of the present invention. Common types of immunoassays are competitive and non-competitive heterogeneous assays, such as enzyme-linked immunosorbent assays (ELISA). In one type of a non-competitive ELISA, antigen is bound to a solid support, such as the surfaces of the reaction chambers of a microfluidic chip. The reaction chambers are treated and/or washed with a blocking agent to prevent further non-specific binding of analyte to the surfaces. The analyte to be quantitated (sample containing primary antibody) is added to the reaction chamber, and antibodies in the sample are allowed to bind to the antigens, thus forming immune complexes. After the immune complexes have formed, excess sample is removed and the immunomatrix chip is washed to remove non-specifically bound antibodies. The immune complexes are then reacted with an appropriate enzyme-labeled anti-immunoglobulin (secondary antibody). The secondary antibody reacts with antibodies in the immune complexes, not with other antigens bound to the chip. Secondary antibodies specific for binding antibodies of different species, including humans, are well known in the art and are commercially available, such as from Sigma Chemical Co. (St. Louis, Mo.) and Santa Cruz Biotechnology (Santa Cruz, Calif.). After another wash step, the enzyme substrate is added. The enzyme linked to the secondary antibody catalyzes a reaction that converts the substrate into a detectable product. When antigen is present in non-limiting quantities, the amount of enzyme catalyzed product is directly proportional to the amount of primary antibodies present in the analytical sample. Preferably, the product is fluorescent or luminescent, which can be measured using technology and equipment well known in the art. It is also possible to use reaction schemes that result in a colored product, which can be measured spectrophotometrically, but such colorimetric reactions are less sensitive than fluorescent or luminescent ones.

Sandwich or capture assays can also be used to identify and quantify immune complexes. In one type of non-competitive ELISA sandwich assay, antibodies are bound to the solid phase and antigen in the analytical sample is measured. These assays are particularly useful for analyzing samples containing low concentrations of antigen having multiple epitopes. This technique requires antibody to be attached to a solid phase in saturating amounts. After washes, the bound antibody is then incubated with the samples, and the antigens in the sample are allowed to form immune complexes with the bound antibody. After washing, the immune complex is incubated with an enzyme-linked secondary antibody, which recognizes the same or a different epitope on the antigen as the primary antibody. Hence, enzyme activity is directly proportional to the amount of antigen in the analytical sample. D. M. Kemeny & S. J. Challacombe, ELISA and Other Solid Phase Immunoassays (1988).

Competitive ELISAs are similar to noncompetitive ELISAs except that a labeled tracer analyte competes with unlabeled analyte in the sample for limited analyte binding sites. For example, in one type of competitive ELISA, a limited number of antigens are bound to the solid support. The sample containing unlabeled antibody is mixed with enzyme-labeled antibody (tracer) at a concentration matched to limited number of antigens bound to the solid support. Antigen-specific antibodies in the sample compete with enzyme-labeled-antibodies for the limited number of antigens bound to the solid support. After immune complexes have formed, non-specifically bound antibodies are removed by washing, enzyme substrate is added, and the enzyme activity is measured. No secondary antibody is required. Because the assay is competitive, enzyme activity is inversely proportional to the amount of antibodies in the biological sample.

An alternative competitive ELISA can also be used within the scope of the present invention. In this alternative embodiment, limited amounts of antibodies from the biological sample are bound to the surface of the solid support as described herein. Labeled and unlabeled antigens are then brought into contact with the solids support such that the labeled and unlabeled antigens compete with each other for binding to the antibodies on the surface of the solid support. After immune complexes have formed, nonspecifically bound antigens are removed by washing. The immune complexes are detected by incubation with an enzyme-linked secondary antibody, which recognizes the same or a different epitope on the antigen as the primary antibody, as described above. The activity of the enzyme is then assayed, which yields a signal that is inversely proportional to the amount of antigen present.

For quantitative analysis calibration standards of known analyte concentration can be assayed to generate a calibration curve relating the amount of enzyme catalyzed product to concentration of analyte. The amount of analyte in a sample can be derived by comparing its yield of detection product to the calibration curve.

Typical enzymes used in ELISA assays detection systems include horseradish peroxidase, glucose oxidase, glucose-6-phosphate dehydrogenase, alkaline phosphatase, β-galactosidase, and urease. Secondary antigen-specific antibodies and streptavidin or avidin linked to various enzymes are commercially available from many suppliers, for example, Sigma Chemical Co., GE Healthcare Life Sciences (Arlington Heights, Ill.) and Pierce Chemical Co. (Rockford, Ill.).

Indirect and amplifying detection reagents are used in immunoassays. The most commonly used system exploits the strong specific binding of avidin with biotin. Avidin is a 66 kDa glycoprotein found in egg white. The avidin protein is made up of four identical 16 kDa subunits, each capable of binding one biotin molecule. A similar protein has been isolated from *Streptomyces avidinii*, which is called streptavidin. Biotin can be conjugated to the analyte-binding species (e.g. secondary antibody). Because biotin is a much smaller moiety than an enzyme, labeling of the secondary antibody is more efficient and several biotins may be conjugated per antibody molecule without affecting its binding affinity for antigen. The avidin or streptavidin protein can be conjugated with enzymes for use in ELISA assays, or fluorescent dyes or chromophores for non-enzymatic detection. Because multiple biotins can label the analyte-binding specie, multiple labeled-avidin or streptavidin complexes can bind to the biotins, increasing the level of detection. A large number of commercial kits and products are available from many suppliers, including Vector Laboratories (Burlingame, Calif.), Pierce Chemical Co., and Invitrogen (Carlsbad, Calif.). M. Wilcheck and E. A. Bayer, Methods Enzymol., 184, 5 (1980).

Homogeneous immunoassays can also be used when practicing the method of the present invention. Homogeneous immunoassays may be preferred for detection of low molecular weight compounds, such as hormones, therapeutic drugs, and illegal drugs that cannot be analyzed by other methods, or compounds found in high concentration. Homogeneous assays are particularly useful because no separation step is necessary. R. C. Boguslaski et al., Clinical Immunochemistry: Principles of Methods and Applications (1984).

In homogeneous techniques, bound or unbound antigens are enzyme-linked. When antibodies in the biological sample bind to the enzyme-linked antigen, steric hindrances inactivate the enzyme. This results in a measurable loss in enzyme activity. Free antigens (i.e., not enzyme-linked) compete with the enzyme-linked antigen for limited antibody binding sites. Thus, enzyme activity is directly proportional to the concentration of antigen in the biological sample.

Enzymes useful in homogeneous immunoassays include lysozyme, neuraminidase, trypsin, papain, bromelain, glucose-6-phosphate dehydrogenase, and .beta-galactosidase. T. Persoon, Immunochemical Assays in the Clinical Laboratory, 5 Clinical Laboratory Science 31 (1992). Enzyme-linked antigens are commercially available or can be linked using various chemicals well known in the art, including glutaraldehyde and maleimide derivatives.

Fluorescent immunoassays can also be used when practicing the method of the present invention. Fluorescent immunoassays (FLISA) are similar to ELISAs except the enzyme is substituted for fluorescent compounds called fluorophores or fluorochromes. These compounds have the ability to absorb energy from incident light and emit the energy as light of a longer wavelength and lower energy. Examples commonly used in the art are fluorescein and rhodamine, and their chemical derivatives such as the Alexa series of fluorophores available commercially from Invitrogen, usually in the form of isothiocyanates that can be readily coupled to antigens and antibodies. D. P. Stites et al., Basic and Clinical Immunology (1994). Fluorescent enzyme substrates are also commercially available for use in ELISA assays. Illustrative fluorescence-based detection methods include ELF-97 alkaline phosphatase substrate (Invitrogen); PBXL1 and PBXL-3 (phycobilisomes conjugated to streptavidin) (Martek Biosciences Corp., Columbia, Md.); FITC and Texas Red labeled goat anti-human IgG (Jackson ImmunoResearch Laboratories, Inc., West Grove, Pa.); and B-Phycoerythrin and R-Phycoerythrin conjugated to streptavidin (Invitrogen). ELF-97 is a nonfluorescent chemical that is modified by alkaline phosphatase to form a fluorescent molecule. Because of turn over of the alkaline phosphatase, use of the ELF-97 substrate results in signal amplification. Fluorescent labels attached to secondary antibodies do not exhibit this amplification and so are generally less sensitive then ELISA assays. FLISA is desirable though for use in the immunomatrix chips because the signal integrity is not as time dependent as enzyme-produced signals and the microvolume reaction chambers of the immunomatrix chips can result in rapid enzyme substrate depletion.

In another sandwich ELISA method using a fluorescent substrate, a solid surface, such as the interior surfaces of a microfluidic reaction chamber are coated with antibody obtained against macromolecules to be determined. Vacant sites are blocked with blocking protein such as casein or bovine serum albumin (BSA). Standards or samples containing macromolecules are added to solid phase and incubated at a temperature in the range of 4° to 37° C. for a period of time. The selected macromolecular antigen in the sample or standard binds to the receptor (primary) antibody. The solid phase is washed and further incubated for a period of time with a second antibody (also raised against macromolecules) covalently linked with an enzyme which is capable of converting a chromogenic or fluorescent substrate to a reactive species that will form an immobilized reaction product. The solid phase is further washed. The label in the reaction product is detected which indicates the presence of the antigen in the sample. The concentration of macromolecule in samples is determined as described using a calibration curve.

There are a number of methods that can be used to attach antibodies, proteins or other antigens to the surface of a solid support. The simplest of these is simple adsorption through hydrophobic, ionic, and van der Waals forces. Other attachment chemistry involves the use of bifunctional organosilanes. E.g., Thompson and Maragos, 44 J. Agric. Food Chem. 1041-1046 (1996). One end of the organosilane reacts with exposed —OH groups on the surface of the chip to form a silanol bond. The other end of the organosilane contains a group that is reactive with various groups on the protein surface such as —$NH_2$ and —SH groups. This method of attaching proteins to the chip results in the formation of a covalent linkage between the protein and the chip. Other preferred methods that have been used for protein attachment to surfaces include arylazide, nitrobenzyl, and diazirine photochemistry methodologies. Exposure of the above chemicals to UV light causes the formation of reactive groups that can react with proteins to form a covalent bond. The arylazide chemistry forms a reactive nitrene group that can insert into C—H bonds, while the diazirine chemistry results in a reactive carbene group. The nitrobenzyl chemistry is referred to as caging chemistry whereby the caging group inactivates a reactive molecule. Exposure to UV light frees the molecule and makes it available for reaction. Still other methods for attaching proteins to solid supports are well known in the art, e.g., S. S. Wong, Chemistry of Protein Conjugation and Cross-Linking (CRC Press, 340 pp., 1991). These typically include the use of amine, thiol, and carboxylate reactive groups present on the surface of macromolecules.

Following attachment of the antigens on the solid support in the selected immunomatrix, the solid support should be washed by rinsing with an appropriate liquid to remove unbound antigens. Appropriate liquids for washing include phosphate buffered saline (PBS) and the like, i.e. relatively low ionic strength, biocompatible salt solutions buffered at or near neutrality. Many appropriate wash liquids are known in the art or can be devised by a person skilled in the art without undue experimentation. E.g., N. E. Good & S. Izawa, Hydrogen Ion Buffers, 24 Methods Enzymology 53-68 (1972).

The solid support is then processed for blocking of non-specific binding of proteins and other molecules to the solid support. This blocking step prevents unintended and undesired binding of antigens, antibodies, and the like to areas of the solid support. Blocking reduces the background that competes with detection signal, thus increasing the signal-to-noise ratio. The solid support is blocked by incubating the solid support in a medium that contain inert molecules that bind to sites where nonspecific binding might otherwise occur. Examples of suitable blockers include BSA, human albumin, gelatin, nonfat dry milk, polyvinyl alcohol, Tween 20 and other detergents, and various commercial blockers, such as SEA BLOCK™ (trademark of East Coast Biologics, Inc., Berwick, Me.) and SuperBlock™ (trademark of Pierce Chemical Co., Rockford, Ill.) blocking buffers.

Following washing for removal of unbound antigens from the array and blocking, the solid support is contacted with a liquid sample to be tested. The sample can be from any animal that generates individual specific antibodies (USA). For example, humans, dogs, cats, mice, horses, cows, and rabbits have all been shown to possess ISAs. The sample can be from various bodily fluids and solids, including blood, saliva, semen, serum, plasma, urine, amniotic fluid, pleural fluid, cerebrospinal fluid, and mixtures thereof. These samples are obtained according to methods well known in the art. Depending on the detection method used, it may be required to manipulate the biological sample to attain optimal assay conditions. For example, the ionic strength or hydrogen ion concentration or the concentration of the biological sample can be adjusted for optimal immune complex formation, enzymatic catalysis, and the like.

Methods for detecting antibody/antigen or immune complexes are well known in the art. The present invention can be modified by one skilled in the art to accommodate the various detection methods known in the art. The particular detection method chosen by one skilled in the art depends on several factors, including the amount of biological sample available, the type of biological sample, the stability of the biological sample, the stability of the antigen, and the affinity between the antibody and antigen. Moreover, as discussed above, depending on the detection methods chosen, it may be required to modify the biological sample.

Fluorescent proteins such as the green-fluorescent protein (GFP) can also be used as detection agents in fluorescent immunoassays. Additionally, Phycobiliproteins isolated from algae, porphyrins, and chlorophylls, which all fluoresce at about 600 nm, are also being used in the art. I. Hemmila, Fluoroimmunoassays and Immunofluorometric Assays, 31 Clin. Chem. 359 (1985); U.S. Pat. No. 4,542,104. Phycobiliproteins and derivatives thereof are commercially available under the names R-phycoerythrin (PE) and Quantum® from, for example, Sigma Chemical Co.

In addition, Cy-conjugated secondary antibodies and antigens are useful in immunoassays and are commercially available. Cy-3, for example, is maximally excited at 554 nm and emits light of between 568 and 574 nm. Cy-3 is more hydrophilic than other fluorophores and thus has less of a tendency to bind nonspecifically or aggregate. Cy-conjugated compounds are commercially available from GE Healthcare Life Sciences.

Illustrative luminescence-based detection methods include CSPD and CDP star alkaline phosphatase substrates (Roche Molecular Biochemicals); and SuperSignal® horseradish peroxidase substrate (Pierce Chemical Co., Rockford, Ill.).

Solid state color detection circuitry can also be used to monitor the color reactions on the biochip and, on command, compare the color patterns before and after the sample application. A color camera image can also be used and the pixel information analyzed to obtain the same information.

Still another method involves detection using a surface plasmon resonance. The surface of the chip is scanned before and after sample application and a comparison is made. The SPR chip relies on the refraction of light when the molecules of interest are exposed to a light source. Each molecule has its own refraction index by which it can be identified. This method requires precise positioning and control circuitry to scan the chip accurately.

Yet another method involves a fluid rinse of the immunomatrix chip with a fluorescing reagent. The microlocations that combine with the biological sample will fluoresce and can be detected with a charge-coupled device (CCD) array. The output of such a CCD array is analyzed to determine the unique pattern associated with each sample. This approach avoids the problems associated with scanning technologies. Speed is not a factor with any of the methods since the chemical combining of sample and reference takes minutes to occur.

Moreover, array scanners are commercially available, such as from Genetic MicroSystems or the LS Series Scanner from Tecan.

Software for image analysis obtained with an array scanner is readily available. Available software packages include ImaGene (BioDiscovery, Los Angeles, Calif.); ScanAlyze (available at no charge; developed by Mike Eisen, Stanford University); DeArray (developed by Yidong Chen and Jeff Trent of the National Institutes of Health; used with IP Lab from Scanalytics, Fairfax, Va.); Pathways (Research Genetics, Huntsville, Ala.); GEM tools (Incyte Pharmaceuticals, Inc., Palo Alto, Calif.); and Imaging Research (GE Healthcare Life Sciences). In the FLISA experiments performed in an immunomatrix chip described below, image data was processed by data analysis software written in MatLab.

Other Binding Assays

Any of a number of binding assays may be performed in microfluidic chips of the present invention, where typically a first member of a binding pair is stably associated with a substrate present on the planar surface of the block element and a second member of the binding pair is free in solution present in the second or hybridization space of the container. A variety of binding assays may be performed in the subject hybridization chambers, where the binding pair members may be: ligands and receptors; antibodies and antigens; complementary nucleic acids; and the like. Of particular interest in many embodiments are hybridization assays in which the binding pair members are complementary nucleic acids. Accordingly, methods of using the hybridization chamber of the subject invention will be further described in terms of hybridization assays. However, the principles reviewed below apply to other types of binding assays, like immunoassay, immunocytochemistry, in situ hybridization, etc., as will be appreciated by one of the skill in the art.

For hybridization assays, the first step is to position the substrate having nucleic acids stably associated on one of its surfaces onto the planar surface of the block element. The nucleic acids may be stably associated with the substrate surface a number of different ways, including covalent and non-covalent binding, where the only requirement is that nucleic acids be sufficiently bound to the surface of the support so as not to dislodge during the hybridization assay steps. Of particular interest are nucleic acid arrays. The nucleic acid arrays employed in the subject hybridization assays have a plurality of specific nucleic acids stably associated with the inner surfaces of the reaction chambers of the matrixed microfluidic chip. Nucleic acid matrix arrays find use in the subject invention including cDNA matrix chips, cRNA matrix chips, polynucleotide matrix chips, oligonucleotide matrix chips, and the like. Of particular interest in many embodiments are the nucleic acid arrays described in: U.S. patent application Ser. No. 08/859,998; U.S. patent application Ser. No. 08/974,298; U.S. patent application Ser. No. 08/859,998; U.S. patent application Ser. No. 08/974,298; U.S. patent application Ser. No. 09/225,998; U.S. application Ser. No. 09/221,480; U.S. application Ser. No. 09/222,432; U.S. application Ser. No. 09/222,436; U.S. application Ser. No. 09/222,437; U.S. application Ser. No. 09/222,251; U.S. application Ser. No. 09/221,481; U.S. application Ser. No. 09/222,256; U.S. application Ser. No. 09/222,248; U.S. application Ser. No. 09/222,253; U.S. application Ser. No. 60/104,179; the disclosures of which are incorporated herein by reference.

After the substrate is positioned onto the interior surface of the reaction chambers, a hybridization solution comprising the complementary components (e.g. complementary nucleic acids or other substances depending on the nature of the assay being performed) is then introduced into the reaction chamber.

Following introduction of the solution or fluid, the reaction chambers are isolated by the actuation of the appropriate valves and hybridization within the reaction chambers is allowed to proceed.

Following hybridization, the matrix is flushed one or more times to remove unbound material (nucleic acid or other substances depending on the assay being performed), followed by detection of hybridized complexes. Although the above described assays have been described primarily in terms of nucleic acid hybridization assays, one of skill in the art will recognize that analogous binding assays or methods can be performed through execution of substantially the same steps. Thus, for ligand/receptor binding assays, a substrate having ligand is stably associated with the interior surfaces of the reaction chambers, followed by introduction of a solution comprising the receptor into the reaction chamber. After a sufficient period of incubation and washing, the presence of ligand-receptor complexes is detected.

Binding assays such as immunoassays, DNA hybridization assays, and receptor-based assays are widely used in the medical community as diagnostic tests for a wide range of target molecules or analytes. Binding assays exploit the ability of certain molecules, herein referred to as "specific binding members", to specifically bind target molecules. Specific binding members such as antibodies, strands of polynucleic acids (DNA or RNA) and molecular receptors, are capable of selectively binding to ("recognizing") potential target molecules such as polynucleic acids, enzymes and other proteins, polymers, metal ions, and low molecular weight organic species such as toxins, illicit drugs, and explosives. In a solid phase assay, a recognition event causes binding members in a fluid test medium to become immobilized with respect to a solid substrate in relation to the amount of analyte present in the medium.

Typically, because of the small size of the molecules involved, recognition events in a binding assay cannot be observed directly. This problem is overcome through the use of labeled binding molecules, which indicate their presence through the generation of a measurable signal. Various types of binding assays have been devised that use radioactive, fluorescent, chemiluminescent, or enzymatic labels. In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, BSA, nonionic detergents (NP-40, Tween, Triton X-100, etc.), nonfat dry milk proteins, Denhardt's reagent, polyvinylpyrrolidone, Ficoll, and other blocking agents. Practitioners may select blocking agents at suitable concentrations to be included in binding assays. However, reaction conditions are selected so as to permit specific binding between intended species (e.g. an anti-apoptotic polypeptide and a physiologically relevant target molecule in a control binding reaction). Blocking agents are included to inhibit nonspecific binding of labeled protein to immobilized polypeptide and/or to inhibit nonspecific binding of labeled polypeptide to the immobilization substrate.

Due to capabilities for multi-directional flow or addition of many reagent and sample components under temporal control, complex binding assays requiring multiple components and many steps may be performed in microfluidic chips of the present invention.

Detection

A number of different detection strategies can be utilized with the microfluidic devices that are provided herein. Selection of the appropriate system is informed in part on the type of event and/or agent being detected. The detectors can be designed to detect a number of different signal types including, but not limited to biotin/avidin labels such as biotinylated antibodies used with labeled streptavidin.

Illustrative detection methodologies suitable for use with the present microfluidic devices include, but are not limited to, optical, light scattering, multichannel fluorescence detection, UV and visible wavelength absorption, luminescence, differential reflectivity, and confocal laser scanning. Additional detection methods that can be used in certain application include scintillation proximity assay techniques, radiochemical detection, fluorescence polarization, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

Detection occurs at a "detection section," or "detection region." These terms and other related terms refer to the portion of the microfluidic device at which detection occurs. As indicated above, with devices utilizing the blind channel design, the detection section is generally the reaction chamber as isolated by the valve associated with each reaction chamber. The detection section for matrix-based devices is usually within regions of flow channels that are adjacent an intersection, the intersection itself, or a region that encompasses the intersection and a surrounding region.

The detection section can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by an optical detector. The optical detector can include one or more photodiodes (e.g., avalanche photodiodes), a fiber-optic light guide leading, for example, to a photomultiplier tube, a microscope, and/or a video camera (e.g., a CCD camera).

Detectors can be microfabricated within the microfluidic device, or can be a separate element. If the detector exists as a separate element and the microfluidic device includes a plurality of detection sections, detection can occur within a single detection section at any given moment. Alternatively, scanning systems can be used. For instance, certain automated systems scan the light source relative to the microfluidic device; other systems scan the emitted light over a detector, or include a multichannel detector. As a specific illustrative example, the microfluidic device can be attached to a translatable stage and scanned under a microscope objective. A signal so acquired is then routed to a processor for signal interpretation and processing. Arrays of photomultiplier tubes can also be utilized. Additionally, optical systems that have the capability of collecting signals from all the different detection sections simultaneously while determining the signal from each section can be utilized.

External detectors are usable because the devices that are provided are completely or largely manufactured of materials that are optically transparent at the wavelength being monitored. This feature enables the devices described herein to utilize a number of optical detection systems that are not possible with conventional silicon-based microfluidic devices.

A particularly preferred detector uses a CCD camera and an optical path that provides for a large field of view and a high numerical aperture to maximize the amount of light collected from each reaction chamber. In this regard, the CCD is used as an array of photodetectors wherein each pixel or group of pixels corresponds to a reaction chamber rather than being used to produce an image of the array. Thus, the optics may be altered such that image quality is reduced or defocused to increase the depth of field of the optical system to collect more light from each reaction chamber.

A detector can include a light source for stimulating a reporter that generates a detectable signal. The type of light source utilized depends in part on the nature of the reporter being activated. Suitable light sources include, but are not limited to, lasers, laser diodes and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions).

Composition of Mixtures for Conducting Reactions

Reactions conducted with the microfluidic devices disclosed herein are typically conducted with certain additives to enhance the reactions. So, for example, in the case of devices in which reagents are deposited, these additives can be spotted with one or more reactants at a reaction chamber, for instance. One set of additives are blocking reagents that block protein binding or antibody binding sites on the elastomeric substrate. A wide variety of such compounds can be utilized including a number of different proteins (e.g., gelatin and various albumin proteins, such as bovine serum albumin) and glycerol.

A detergent additive can also be useful. Any of a number of different detergents can be utilized. Examples include, but are not limited to SDS and the various Triton detergents.

Assays

The array-based devices described herein (see, e.g., FIGS. 1A, 1F, 2, 3A, 3B, and 4-7 and accompanying text) are inherently designed to conduct a large number of immunological reactions (e.g., ELISAs) at the same time. This feature, however, can readily be further expanded upon by conducting multiple analyses (e.g., measuring binding kinetics, affinity and quantitative specificity) within each reaction chamber.

The devices of the invention, for example, may be used as an analytical tool to determine whether a particular target protein or peptide of interest is present or absent in a sample. Such devices may also be used to detect the presence or amount of antibodies in a sample.

The devices may be utilized to test for the presence or quantity of particular pathogen, or for the presence or quantity of proteins, peptides or antibodies associated with such pathogens (e.g., viruses, bacteria or fungi). Such applications would provide a quick, efficient, accurate, sensitive and inexpensive screening method useful in public health and counter-bio-terrorism applications.

The invention may also be used to detect protein and non-protein agents, poisons and toxins (such as abrin, ricin and modeccin etc), and nerve agents, e.g., the "G" agents (such as tabun, soman, sarin, and cyclosarin) and the "V" agents, such as VX.

Such devices could also be used for identification purposes (e.g., paternity and forensic applications). Such devices could also be utilized to detect or characterize specific proteins or antibodies correlated with particular diseases or genetic disorders such as diabetes, cancer etc.

Alternatively, the devices can be used to perform combinatorial synthetic chemistry or immunology, preparing a large number of combinations simultaneously.

While useful for conducting a wide variety of immunological analyses, the devices can also be utilized in a number of other applications as well. As indicated earlier, the devices can be utilized to analyze essentially any interaction between two or more species that generates a detectable signal or a reaction product that can reacted with a detection reagent that generates a signal upon interaction with the reaction product.

Thus, for example, the devices can be utilized in a number of screening applications to identify test agents that have a particular desired activity. As a specific example, the devices can be utilized to screen compounds for activity as a substrate or inhibitor of one or more enzymes. In such analyses, test compound and other necessary enzymatic assay reagents (e.g., buffer, metal ions, cofactors and substrates) are introduced (if not previously deposited) in the reaction chamber. The enzyme sample is then introduced and reaction (if the test compound is a substrate) or inhibition of the reaction (if the test compound is an inhibitor) is detected. Such reactions or inhibition can be accomplished by standard techniques, such as directly or indirectly monitoring the loss of substrate and/or appearance of product.

Further discussion of related devices and applications of such devices is set forth in copending and commonly owned U.S. non-provisional patent application Ser. No. 10/819,088 and U.S. Provisional application No. 60/335,292, filed Nov. 30, 2001, which are both incorporated herein by reference in its entirety for all purposes.

Fabrication

A. General Aspects

As alluded to earlier, the microfluidic devices that are provided are generally constructed utilizing single and multi-layer soft lithography (MSL) techniques and/or sacrificial-layer encapsulation methods. The basic MSL approach involves casting a series of elastomeric layers on a micro-machined mold, removing the layers from the mold and then fusing the layers together. In the sacrificial-layer encapsulation approach, patterns of photoresist are deposited wherever a channel is desired. These techniques and their use in producing microfluidic devices is discussed in detail, for example, by Unger et al. (2000) Science 288:113-116, by Chou, et al. (2000) "Integrated Elastomer Fluidic Lab-on-a-chip-Surface Patterning and DNA Diagnostics, in Proceedings of the Solid State Actuator and Sensor Workshop, Hilton Head, S.C.; and in PCT Publication WO 01/01025, each of which is incorporated herein by reference in their entirety for all purposes.

In brief, the foregoing fabrication methods initially involve fabricating mother molds for top layers (e.g., the elastomeric layer with the control channels) and bottom layers (e.g., the elastomeric layer with the flow channels) on silicon wafers by photolithography with photoresist (Shipley SJR 5740). Channel heights can be controlled precisely by the spin coating rate. Photoresist channels are formed by exposing the photoresist to UV light followed by development. Heat reflow process and protection treatment is typically achieved as described by M. A. Unger, Chou, T. Throsen, A. Scherer and S. R. Quake, Science (2000) 288:113, which is incorporated herein by reference in its entirety. A mixed two-part-silicone elastomer (GE RTV 615) is then spun into the bottom mold and poured onto the top mold, respectively. Here, too, spin coating can be utilized to control the thickness of bottom polymeric fluid layer. The partially cured top layer is peeled off from its mold after baking in the oven at 80° C. for 25 minutes, aligned and assembled with the bottom layer. A 1.5-hour final bake at 80° C. is used to bind these two layers irreversibly. Once peeled off from the bottom silicon mother mold, this RTV device is typically treated with HCL (0.1N, 30 min at 80° C.). This treatment acts to cleave some of the Si—O—Si bonds, thereby exposing hydroxy groups that make the channels more hydrophilic.

The device can then optionally be hermetically sealed to a support. The support can be manufactured of essentially any material, although the surface should be flat to ensure a good seal, as the seal formed is primarily due to adhesive forces. Examples of suitable supports include glass, plastics and the like.

The devices formed according to the foregoing method result in the substrate (e.g., glass slide) forming one wall of the flow channel. Alternatively, the device once removed from the mother mold is sealed to a thin elastomeric membrane such that the flow channel is totally enclosed in elastomeric material. The resulting elastomeric device can then optionally be joined to a substrate support.

Devices Utilizing Blind Channel Design

Layer Formation

Microfluidic devices based on the blind channel design in which reagents are deposited at the reaction chambers during manufacture are typically formed of three layers. The bottom layer is the layer upon which reagents are deposited. The bottom layer can be formed from various elastomeric materials as described in the references cited above on MLS methods. Typically, the material is polydimethylsiloxane (PMDS) elastomer. Based upon the arrangement and location of the reaction chambers that is desired for the particular device, one can determine the locations on the bottom layer at which the appropriate reagents should be spotted. Because PMDS is hydrophobic, the deposited aqueous spot shrinks to form a very small spot. The deposited reagents are deposited such that a covalent bond is not formed between the reagent and the surface of the elastomer because, as described earlier, the reagents are intended to dissolve in the sample solution once it is introduced into the reaction chamber.

The other two layers of the device are the layer in which the flow channels are formed and the layer in which the control and optionally guard channels are formed. These two layers are prepared according to the general methods set forth earlier in this section. The resulting two layer structure is then placed on top of the first layer onto which the reagents have been deposited. A specific example of the composition of the three layers is as follows (ration of component A to component B): first layer (sample layer) 30:1 (by weight); second layer (flow channel layer) 30:1; and third layer (control layer) 4:1. It is anticipated, however, that other compositions and ratios of the elastomeric components can be utilized as well.

Spotting

The reagents can be deposited utilizing any of a number of commercially available reagent spotters and using a variety of established spotting techniques. Examples of suitable spotter that can be utilized in the preparation of the devices include pin spotters, acoustic spotters, automated micropipettors, electrophoretic pumps, ink jet printer devices, ink drop printers, and certain osmotic pumps. Examples of commercially available spotters include: Cartesian Technologies MicroSys 5100 (Irvine, Calif.), Hitach SPBIO (Alameda, Calif.), Genetix Q-Array (United Kingdom), Affymetrix 417 (Santa Clara, Calif.) and Packard Bioscience SpotArray (Meriden, Conn.). In general, very small spots of reagents are deposited; usually spots of less than 10 nl are deposited, in other instances less than 5 nl, 2 nl or 1 nl, and in still other instances, less than 0.5 nl, 0.25 nl, or 0.1 nl.

Example 2

The following example shows a typical use of one embodiment of the device, in this case the 24×96 microfluidic immuno-array (FIG. 6) to perform a sandwich ELISA.

1) Binding protein: Flow about 10 microliters of binding protein solution through the common inlet. Flow the solution for about 20-30 seconds, and then leave the solution to incubate for 10-20 minutes. Repeat three times (three cycles) for a total incubation time of about an hour. 2) Blocking Carrier: Flow the blocking carrier through the sample inlet for about 5 minutes. As will be easily recognized by those of skill in the art, this step may be done prior to step 1. 3) Wash continuously for about 3 minutes. 4) Primary Antibody: Flow primary antibody solution through the chip via the primary antibody inlet. Flow for about 20 seconds and incubate for about 10 minutes. Repeat three times. 5) Wash, as above. 6) Antigen: Flow for about 2 seconds and incubate for about 8 seconds, repeat continuously for about an hour. 7) Wash, as above. 8) Secondary Antibody: Flow secondary antibody solution through the chip via the secondary antibody inlet. 9) Wash, as above. 10) Enzyme (streptavidin): flow for 20 seconds; incubate for about 100 seconds, repeat three times. 11) Wash, as above. 12) Substrate: flow for about 5 seconds; incubate for about 35 seconds, repeat five times. 13) detect and measure signal.

The times and volumes used may be varied according to the particulars of the experiment, and the reagents, proteins and antibodies being used. Washing and incubation times and number of repetitions may be varied by several hundred times without substantively departing from the spirit of the invention.

Example 3

FLISA Assay Development for a 48 Row by 18 Column Immunomatrix Chip

The purpose of this example is to verify the high sensitivity and dynamic range of a 48×18 immunomatrix chip with MCP-1, MCP-3, and IL-6 antigens. The time for completing 864 data points was under 6 hours.

Materials & Methods:
  Binding Protein: Protein L, ImmunoPure recombinant Protein L, 1 mg, dissolved in 250 uL of 1×PBS, pH 7.6.
  Purified Mo anti-Human CCL2/MCP-1, Mouse IgG2b, 500 ug; reconstituted to 500 ug/mL with 1×PBS.
  Biotinylated Goat anti-Human CCL2/MCP-1 antibody, 50 ug; reconstituted to 500 ug/mL with 1×TBS, 0.1% BSA.
  Recombinant human CCL2/MCP-1, 10 ug, reconstituted to 10 ug/mL with 1×PBS, 0.1% BSA.
  Purified Mo anti-Human CCL7/MCP-3, Mouse IgG1, 500 ug; reconstituted to 500 ug/mL with 1×PBS.
  Biotinylated Goat anti-Human CCL7/MCP-3, 50 ug; reconstituted to 500 ug/mL with 1×TBS, 0.1% BSA.
  Recombinant human CCL7/MCP-3, 10 ug, reconstituted to 100 ug/mL with 1×PBS, 0.1% BSA.
  Purified Rat IgG1 anti-Human IL-6 monoclonal, 0.5 mg reconstituted in 1 mL, [0.5 mg/mL]
  Biotinylated Rat IgG2a anti-Human IL-6 monoclonal, 0.5 mg reconstituted in 1 mL, [0.5 mg/mL]
  Recombinant Human IL-6, 10 ug, dissolved in 1 mL 1×PBS, 0.1% w/v BSA to [10 ug/mL].
  Alexa Fluor 633-Streptavidin, 1 mg (dissolved in 1 mL PBS), [1 mg/mL]
  Alexa Fluor 488 hydrazide, sodium salt, 1 mg dissolved in 1 mL PBS, [1 mg/mL]
  10×PBS w/o Ca$^{++}$, w/o Mg$^{++}$
  1×PBS: Diluted from 10× stock
  1×PBS, 0.1% BSA, sterile filtered
  SuperBlock T20 (PBS) Blocking Buffer: Pierce Chemical Company, contains 0.05% Tween 20 and Kathon CG/ICP preservative.
  Carbonate-Bicarbonate Buffer Capsules: 0.05M carbonate-bicarbonate buffer, pH 9.6 at 25° C.
  Chip controller: HAL, NanoFlex Controller 340
  TECAN LS Reloaded fluorescent plate imaging system with Array Pro Analyzer software Procedure:
1. Protein L Dilution: In 0.15 M Carbonate/Bicarbonate, pH 9.5 Final (Chip Load=20 uL Per Well)

| Final Conc. Prot L | Prot L stock | 0.2 M carbonate/ bicarbonate buffer | Total Vol. |
| --- | --- | --- | --- |
| 500 ug/mL | 8 µL [4 mg/mL] | 56 µL | 64 µL |
| 100 ug/mL | 20 uL [500 ug/mL] | 80 uL | 100 uL |

2. Primary Antibody: Dilutions (Chip Load=10 uL Per Well)

Purified Anti-CCL2/MCP-1

| Final Conc. Ab (µg/mL) | Vol. Biot. Ab stock | Ab stock conc. | SuperBlock T20 | Total Vol. |
| --- | --- | --- | --- | --- |
| 250 | 15 µL | 500 µg/mL | 15 µL | 30 µL |
| 125 | 7.5 uL | 500 ug/mL | 22.5 uL | 30 uL |

Purified Anti-CCL7/MCP-3

| Final Conc. Ab (µg/mL) | Vol. Biot. Ab stock | Ab stock conc. | SuperBlock T20 | Total Vol. |
| --- | --- | --- | --- | --- |
| 250 | 15 µL | 100 µg/mL | 15 µL | 30 µL |
| 125 | 7.5 uL | 100 ug/mL | 22.5 uL | 30 uL |

Purified Anti-IL-6

| Final Conc. Ab (µg/mL) | Vol. Biot. Ab stock | Ab stock conc. | SuperBlock T20 | Total Vol. |
| --- | --- | --- | --- | --- |
| 250 | 15 µL | 500 µg/mL | 15 µL | 30 µL |
| 125 | 7.5 uL | 500 ug/mL | 22.5 uL | 30 uL |

3. A) Secondary Antibody: Dilutions (Chip Load=10 uL Per Well)

Biotinylated Anti-CCL2/MCP-1

| Final Conc. Ab (µg/mL) | Vol. Biot. Ab stock | Ab stock conc. | SuperBlock T20 | Total Vol. |
| --- | --- | --- | --- | --- |
| 200 | 20 uL | 500 µg/mL | 30 uL | 50 uL |
| 100 | 9 µL | 500 µg/mL | 36 µL | 45 µL |

Biotinylated Anti-CCL7/MCP-3

| Final Conc. Ab (µg/mL) | Vol. Biot. Ab stock | Ab stock conc. | SuperBlock T20 | Total Vol. |
| --- | --- | --- | --- | --- |
| 100 | 60 µL | 100 µg/mL | 0 µL | 60 µL |

Biotinylated Anti-IL-6

| Final Conc. Ab (µg/mL) | Vol. Biot. Ab stock | Ab stock conc. | SuperBlock T20 | Total Vol. |
|---|---|---|---|---|
| 200 | 20 uL | 500 ug/mL | 30 uL | 50 uL |
| 100 | 10 µL | 500 µg/mL | 40 µL | 50 uL |

5. Dilute Antigen for Chip: (Chip Load=45 uL Per Well)
I) rHum CCL2/MCP-1

| Stock Vol | Stock Conc. | SuperBlock T20 Vol | Total Vol | Final Conc |
|---|---|---|---|---|
| 2 uL | 10 ug/mL | 18 uL | 20 uL | 1 ug/mL |
| 2 uL A | 1 ug/mL | 18 uL | 20 uL | 100 ng/mL |
| 10 uL B | 100 ng/mL | 90 uL | 100 uL | 10 ng/mL |
| 30 uL C | 10 ng/mL | 270 uL | 300 uL | 1 ng/mL |
| 100 uL D | 1 ng/mL | 100 uL | 200 uL | 500 pg/mL |
| 40 uL D | 1 ng/mL | 160 uL | 200 uL | 200 pg/mL |
| 40 uL D | 1 ng/mL | 360 uL | 400 uL | 100 pg/mL |
| 100 uL 3 | 100 pg/mL | 100 uL | 200 uL | 50 pg/mL |
| 40 uL 3 | 100 pg/mL | 160 uL | 200 uL | 20 pg/mL |
| 20 uL 3 | 100 pg/mL | 180 uL | 200 uL | 10 pg/mL |
| 10 uL 3 | 100 pg/mL | 190 uL | 200 uL | 5 pg/mL |
| 0 | 0 | 200 uL | 200 uL | 0 pg/mL |

J) rHum CCL7/MCP-3

| Stock Vol | Stock Conc. | SuperBlock T20 Vol | Total Vol | Final Conc |
|---|---|---|---|---|
| 2 uL | 100 ug/mL | 18 uL | 20 uL | 10 ug/mL |
| 2 uL A | 10 ug/mL | 18 uL | 20 uL | 1 ug/mL |
| 2 uL B | 1 ug/mL | 18 uL | 20 uL | 100 ng/mL |
| 10 uL C | 100 ng/mL | 90 uL | 100 uL | 10 ng/mL |
| 30 uL D | 10 ng/mL | 270 uL | 300 uL | 1 ng/mL |
| 100 uL E | 1 ng/mL | 100 uL | 200 uL | 500 pg/mL |
| 40 uL E | 1 ng/mL | 160 uL | 200 uL | 200 pg/mL |
| 40 uL E | 1 ng/mL | 360 uL | 400 uL | 100 pg/mL |
| 100 uL 3 | 100 pg/mL | 100 uL | 200 uL | 50 pg/mL |
| 40 uL 3 | 100 pg/mL | 160 uL | 200 uL | 20 pg/mL |
| 20 uL 3 | 100 pg/mL | 180 uL | 200 uL | 10 pg/mL |
| 10 uL 3 | 100 pg/mL | 190 uL | 200 uL | 5 pg/mL |
| 0 | 0 | 200 uL | 200 uL | 0 pg/mL |

K) rHum IL-6

| Stock Vol | Stock Conc. | SuperBlock T20 Vol | Total Vol | Final Conc |
|---|---|---|---|---|
| 2 uL | 10 ug/mL | 18 uL | 20 uL | 1 ug/mL |
| 2 uL A | 1 ug/mL | 18 uL | 20 uL | 100 ng/mL |
| 10 uL B | 100 ng/mL | 90 uL | 100 uL | 10 ng/mL |
| 30 uL C | 10 ng/mL | 270 uL | 300 uL | 1 ng/mL |
| 100 uL D | 1 ng/mL | 100 uL | 200 uL | 500 pg/mL |
| 40 uL D | 1 ng/mL | 160 uL | 200 uL | 200 pg/mL |
| 40 uL D | 1 ng/mL | 360 uL | 400 uL | 100 pg/mL |
| 100 uL 3 | 100 pg/mL | 100 uL | 200 uL | 50 pg/mL |
| 40 uL 3 | 100 pg/mL | 160 uL | 200 uL | 20 pg/mL |
| 20 uL 3 | 100 pg/mL | 180 uL | 200 uL | 10 pg/mL |
| 10 uL 3 | 100 pg/mL | 190 uL | 200 uL | 5 pg/mL |
| 0 | 0 | 200 uL | 200 uL | 0 pg/mL |

6. Alexa Fluor 488 Dye Spiked Wash Buffer:

| Final Conc. Alexa 488 | Alexa 488 hydrazide stock | SuperBlock T20 |
|---|---|---|
| 143 ng/mL | 1 µL of [1 mg/mL] | 7 mL |

7. Alexa Fluor 633-Streptavidin: [125 ug/mL]:

| Final Conc. SA (µg/mL) | Vol. SA stock | SA stock conc. | SuperBlock T20 |
|---|---|---|---|
| 125 | 5 µL | 1000 µg/mL | 35 µL |

II. A. Load Chips:
1. Pipet 150 µL of DI water into the 10 pressurization control ports.
2. Pipet 0.5 mL of dye-spiked SuperBlock T20 into the wash port.
3. Pipet 25 µL Binding Protein into carrier (Port X).
4. Pipet 25 uL of Alexa 633-Streptavidin into carrier (Port Y)
5. Pipet 10 µL of Primary Antibody into indicated carrier ports for Primary Antibody.
6. Pipet 10 µL of Secondary Antibody into indicated carrier ports for Secondary Antibody.
7. Pipet 45 µL of Antigen Samples into indicated carrier ports for Samples.

A) Primary Antibodies Loaded into Primary Ab Ports 10 uL Per Port

| Ab Col | | Primary Ab |
|---|---|---|
| 1 | A2 | 125 ug/mL Anti-CCL2/MCP-1 |
| 2 | A2 | 125 ug/mL Anti-CCL2/MCP-1 |
| 3 | | 0 |
| 4 | A1 | 250 ug/mL Anti-CCL2/MCP-1 |
| 5 | A1 | 250 ug/mL Anti-CCL2/MCP-1 |
| 6 | | 0 ug/mL |
| 7 | B2 | 125 ug/mL Anti-CCL7/MCP-3 |
| 8 | B2 | 125 ug/mL Anti-CCL7/MCP-3 |
| 9 | | 0 |
| 10 | B1 | 250 ug/mL Anti-CCL7/MCP-3 |
| 11 | B1 | 250 ug/mL Anti-CCL7/MCP-3 |
| 12 | | 0 |
| 13 | C2 | 125 ug/mL Anti-IL-6 |
| 14 | C2 | 125 ug/mL Anti-IL-6 |
| 15 | | 0 |
| 16 | C1 | 250 ug/mL Anti-IL-6 |
| 17 | | 0 |
| 18 | C1 | 250 ug/mL Anti-IL-6 |

B). Biotinylated Ab Loaded into Secondary Antibody Ports: 10 uL Per Port

| Ab Col | | Secondary Biotinylated Ab |
|---|---|---|
| 1 | 100 ug/mL | Biot-anti-Hum CCL2/MCP-1 |
| 2 | 200 ug/mL | Biot-anti-Hum CCL2/MCP-1 |
| 3 | 200 ug/mL | Biot-anti-Hum CCL2/MCP-1 |
| 4 | 100 ug/mL | Biot-anti-Hum CCL2/MCP-1 |
| 5 | 200 ug/mL | Biot-anti-Hum CCL2/MCP-1 |
| 6 | 0 | SuperBlock T20 |
| 7 | 100 ug/mL | Biot-anti-Hum CCL7/MCP-3 |
| 8 | 100 ug/mL | Biot-anti-Hum CCL7/MCP-3 |
| 9 | 100 ug/mL | Biot-anti-Hum CCL7/MCP-3 |
| 10 | 100 ug/mL | Biot-anti-Hum CCL7/MCP-3 |
| 11 | 100 ug/mL | Biot-anti-Hum CCL7/MCP-3 |
| 12 | 0 | SuperBlock T20 |
| 13 | 100 ug/mL | Biot-anti-Hum IL-6 |
| 14 | 200 ug/mL | Biot.-anti-Hum IL-6 |
| 15 | 200 ug/mL | Biot.-anti-Hum IL-6 |
| 16 | 100 ug/mL | Biot.-anti-Hum IL-6 |
| 17 | 0 | SuperBlock T20 |
| 18 | 200 ug/mL | Biot.-anti-Hum IL-6 |

8. Antigen Samples Loaded into Sample Ports: 45 uL Per Port

| Port No. | Final Conc. [µg/mL] | Antigen sample |
|---|---|---|
| 1 | 500 pg/mL | rHum CCL2/MCP-1 |
| 2 | 200 pg/mL | |
| 3 | 100 pg/mL | |
| 4 | 50 pg/mL | |
| 5 | 20 pg/mL | |
| 6 | 10 pg/mL | |
| 7 | 5 pg/mL | |
| 8 | 0 pg/mL | |
| 9 | 500 pg/mL | rHum CCL7/MCP-3 |
| 10 | 200 pg/mL | |
| 11 | 100 pg/mL | |
| 12 | 50 pg/mL | |
| 13 | 20 pg/mL | |
| 14 | 10 pg/mL | |
| 15 | 5 pg/mL | rHum CCL7/MCP-3 |
| 16 | 0 pg/mL | |
| 17 | 500 pg/mL | rHum IL-6 |
| 18 | 200 pg/mL | |
| 19 | 100 pg/mL | |
| 20 | 50 pg/mL | |
| 21 | 20 pg/mL | |
| 22 | 10 pg/mL | |
| 23 | 5 pg/mL | |
| 24 | 0 pg/mL | |
| 25 | 500 pg/mL | rHum CCL2/MCP-1 |
| 26 | 200 pg/mL | |
| 27 | 100 pg/mL | |
| 28 | 50 pg/mL | |
| 29 | 20 pg/mL | |
| 30 | 10 pg/mL | |
| 31 | 5 pg/mL | |
| 32 | 0 pg/mL | |
| 33 | 500 pg/mL | rHum CCL7/MCP-3 |
| 34 | 200 pg/mL | |
| 35 | 100 pg/mL | |
| 36 | 50 pg/mL | |
| 37 | 20 pg/mL | |
| 38 | 10 pg/mL | |
| 39 | 5 pg/mL | |
| 40 | 0 pg/mL | |
| 41 | 500 pg/mL | rHum IL-6 |
| 42 | 200 pg/mL | |
| 43 | 100 pg/mL | |
| 44 | 50 pg/mL | |
| 45 | 20 pg/mL | |
| 46 | 10 pg/mL | |
| 47 | 5 pg/mL | |
| 48 | 0 pg/mL | |

III. Run Chips:
1. Place chips in controller no. 340 using remote appliance
2. Script synopsis:
   1) Step "Initialization" (Sets air pressures, opens all valves for starters) [about 15 seconds]
   2) Step "Establishing Control" (Fills all valves and closes them) [6 min]
   3) Step "Fill Matrix Header (Wash and BP)" (Fills gap between samples and matrix) [3 min]
   4) Step "Surface Preparation" (Loads binding protein)
      i. Fill solution and wash on
      ii. Blind fill the matrix with binding protein [15 min]; samples and antibodies loading into chip ports at the same time.
      iii. Dilation pump binding protein from common lines across the matrix to exhaust on primary antibody side [18 min]
      iv. TOTAL Protein L incubation=33 min
      v. Wash exhaust line on primary antibody side, dilation pumping 30×6 sec/cycle (2&2) from Wash
      vi. Wash across the length of matrix from primary antibody side to secondary antibody side, dilation pumping
      vii. Wash across the length of matrix to common reagent lines and port X, dilation pumping TOTAL Wash of matrix=10 min
   5) Step "Add Primary Antibodies" (Loads primary antibodies)
      i. Dilation pump primary antibodies across the matrix to exhaust on secondary antibody side
      ii. TOTAL Primary antibody addition/incubation=30 min
      iii. Wash exhaust line on primary antibody side, dilation pumping from Wash
      iv. Wash across the length of matrix from primary antibody side to secondary antibody side, dilation pumping
      v. TOTAL Wash of matrix=6 min 40 sec
   6) Step "Add Samples" (Loads antigen samples)
      i. Dilation pump Samples across the width of matrix to sample exhaust [180 min]
      ii. Total Sample addition/incubation=3 hours
      iii. Wash across the width of matrix from Sample Wash to sample exhaust, dilation pumping
      iv. Total Wash of matrix 40 cycles [2 min 40 sec]
   7) Step "Add Secondary Antibodies" (Loads secondary antibodies)
      i. Dilation pump secondary antibodies across the matrix to exhaust on primary antibody side
      ii. TOTAL Secondary antibody addition/incubation=30 min
      iii. Wash exhaust line on primary antibody side, dilation pumping from Wash
      iv. Wash across the length of matrix from primary antibody side to secondary antibody side, dilation pumping
      v. TOTAL Wash of matrix=6 min 40 sec
   8) Step "Add Streptavidin" (Loads labeled streptavidin to detect assay signal)
      i. Dilation pump streptavidin across the matrix to exhaust on primary antibody side
      ii. TOTAL Streptavidin addition/incubation=18 min
      iii. Wash exhaust line on primary antibody side, dilation pumping from Wash
      iv. Wash across the length of matrix from primary antibody side to secondary antibody side, dilation pumping
      v. TOTAL Wash of matrix=6 min 40 sec
      vi. Wash across the length of matrix to common reagent lines and port X, dilation pumping
   9) Step "Final" (Traps pressure in containment valves to keep X & Y valves closed, releases pressure in all other areas of chip) [about 15 seconds]

V. Results.

Figure 16A:
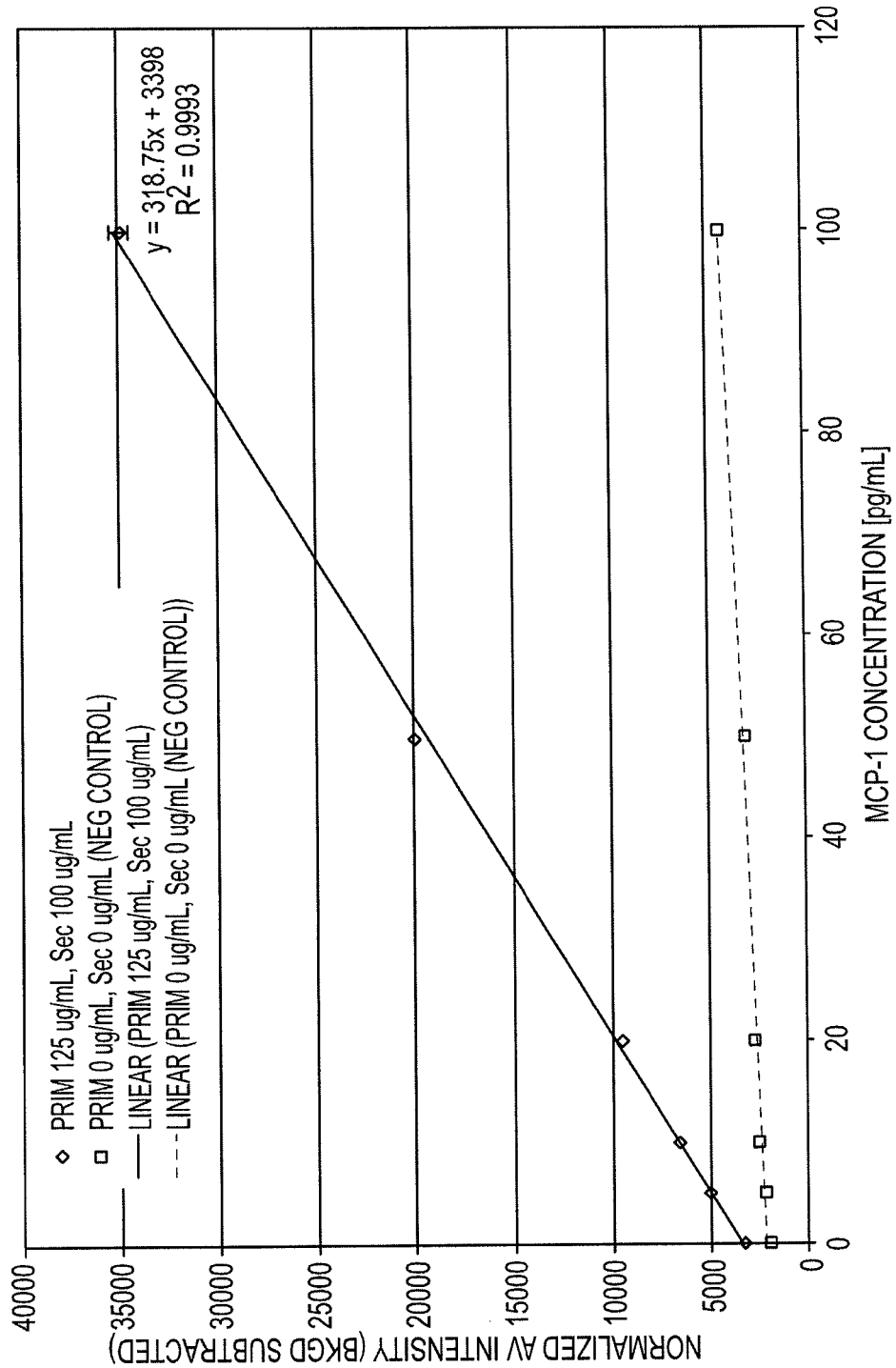
FIG. 16A is a FLISA calibration curve showing detection of low concentration of MCP-1 antigen.
Figure 16B:
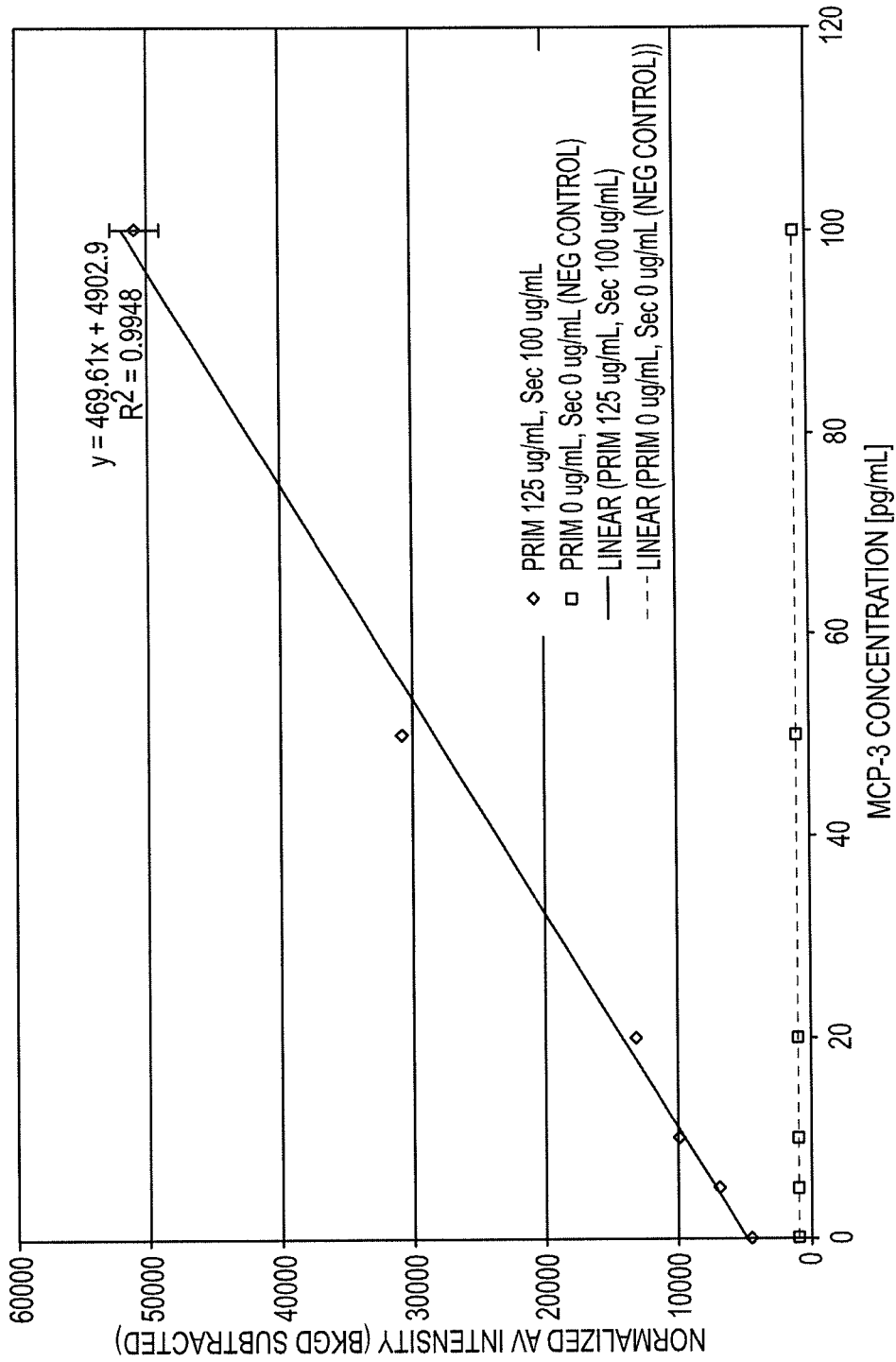
FIG. 16B is a FLISA calibration curve showing detection of low concentration of MCP-1 antigen.

For MCP-1 and MCP-3 assays, good calibration curves to less than 5 pg/mL were obtained. IL-6 data were equivocal due to use of old antibody supply stocks and calibration curve could not be obtained. The FLISA calibration curves for MCP-1 and MCP-3 are shown in FIG. 16A and FIG. 16B.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are incorporated by reference in their entirety for all purposes to the same extent as if each individual publication, patent or patent application were specifically and individually indicated to be so incorporated by reference. In instances when incorporated references conflict with the instant specification, the instant specification is controlling.

The invention claimed is:

1. A microfluidic chip comprising:
   a plurality of flow channels formed as a matrix defining reaction chambers that are arranged in a plurality of fluidic columns and a plurality of fluidic rows,
   a first plurality of valves that upon actuation turn off fluidic communication through the fluidic rows of the matrix while permitting flow through the fluidic columns of the matrix,
   a second plurality of valves that upon actuation turn off fluidic communication through columns of the matrix while permitting flow through the fluidic rows of the matrix, a plurality of supply channels that are connected to supply test samples and reagents from sources thereof to the matrix, and
   a plurality of dedicated flushing channels that are connected to supply wash solution from a source thereof to the matrix and are separate from the plurality of supply channels,
   wherein the dedicated flushing channels are constructed and arranged to operate in the following configurations:
   (A) a closed configuration, wherein flow of wash solutions through the flushing channels is closed;
   (B) a first open configuration, wherein the first plurality of valves is closed, the second plurality of valves is open, and the fluidic columns are flushed with the wash solution; and
   (C) a second open configuration, wherein the second plurality of valves is closed, the first plurality of valves is open, and the fluidic rows are flushed with the wash solution.

2. A microfluidic chip according to claim 1 comprised of an elastomeric material.

3. A microfluidic chip according to claim 1 wherein each of the fluidic columns comprises a first row flow channel segment that defines the top of each of the fluidic columns and each of the fluidic columns has a last row flow channel segment that defines the bottom of each of the fluidic columns,
   wherein the first row flow channel segments each comprise a first flow channel segment connection channel in fluid communication with the first row flow channel segment for each column of the matrix, and
   wherein each of the fluidic columns the last row flow channel segments comprise a second flow channel segment connection channel in fluid communication with the last row flow channel segments for each fluidic column of the matrix.

4. A microfluidic chip according to claim 3 wherein each of the plurality of first row flow channel connection segments is fluidically bifurcated into a first inlet channel and a first outlet channel and each of the plurality of last row flow channel connection segments is fluidically bifurcated into a second inlet channel and a second outlet channel.

5. A microfluidic chip according to claim 4 wherein each first inlet channel, each first outlet channel, each second inlet channel, and each second outlet channel further comprises an addressable valve for stopping fluidic communication through each first inlet channel, each first outlet channel, each second inlet channel, and each second outlet channel.

6. A microfluidic chip according to claim 1 wherein each reaction chamber defined in the matrix comprises a first flush inlet and a second flush inlet.

7. A microfluidic chip according to claim 6 wherein each reaction chamber is comprised of a flow channel with a first end opening and a second end opening that define a length of the reaction chamber wherein one half of the length of the reaction chamber defines a reaction chamber midpoint demarking a first zone of the reaction chamber and a second zone of the reaction chamber,
   wherein the first flush inlet fluidically communicates with the first zone of the reaction chamber and the second flush inlet fluidically communicates with the second zone of the reaction chamber.

8. A microfluidic chip according to claim 6 wherein the communication of the first flush inlet with the reaction chamber and the communication of the second flush inlet with the reaction chamber is spaced a distance that is about one quarter or greater of the length of the reaction chamber.

9. A microfluidic chip according to claim 1 that is configured for performing immunoassays, wherein the chip comprises:
   a plurality of reaction chambers configured to reduce antibody crosstalk, the chambers having a volume of less than 5 nL per chamber,
   wherein the plurality of reaction chambers comprise a plurality of alternating serpentine flow channels in successive fluidic communication.

10. A microfluidic chip according to claim 9 wherein each of the plurality of reaction chambers has a volume of less than 1 nL.

11. A microfluidic chip according to claim 9 wherein each of the plurality of reaction chambers has a plurality of flow channel inlets comprising a first inlet connected to a source of primary antibody and a second inlet connected to a source of secondary antibody.

12. A microfluidic chip according to claim 9 further comprising a binding protein.

13. A microfluidic chip according to claim 12 further comprising a primary antibody bound to the binding protein.

14. A microfluidic chip according to claim 9 further comprising a linker molecule and a reagent wherein the linker covalently attaches the reagent to the reaction chamber.

15. A microfluidic chip according to claim 9, configured for performing 432 or more simultaneous immunoassays.

* * * * *